United States Patent
Krishnan et al.

(10) Patent No.: US 10,722,551 B2
(45) Date of Patent: Jul. 28, 2020

(54) POLYPEPTIDES COMPRISING A MODIFIED BACTERIOPHAGE G3P AMINO ACID SEQUENCE LACKING A GLYCOSYLATION SIGNAL

(71) Applicant: Proclara Biosciences, Inc., Cambridge, MA (US)

(72) Inventors: Rajaraman Krishnan, Ashland, MA (US); Eva Asp, Newton, MA (US); Ming Proschitsky, Winchester, MA (US); Richard Fisher, Cambridge, MA (US); Francis J. Carr, Balmedie (GB); Robert G. E. Holgate, Royston (GB); Timothy D. Jones, Babraham (GB)

(73) Assignee: Proclara Biosciences, Inc., Cambridge, MA (US)

( * ) Notice: Subject to any disclaimer, the term of this patent is extended or adjusted under 35 U.S.C. 154(b) by 37 days.

(21) Appl. No.: 15/532,820

(22) PCT Filed: Dec. 2, 2015

(86) PCT No.: PCT/US2015/063476
§ 371 (c)(1),
(2) Date: Jun. 2, 2017

(87) PCT Pub. No.: WO2016/090022
PCT Pub. Date: Jun. 9, 2016

(65) Prior Publication Data
US 2018/0207231 A1    Jul. 26, 2018

Related U.S. Application Data

(60) Provisional application No. 62/087,052, filed on Dec. 3, 2014.

(51) Int. Cl.
| | | |
|---|---|---|
| *A61K 38/16* | (2006.01) | |
| *C07K 14/005* | (2006.01) | |
| *A61K 9/00* | (2006.01) | |
| *A61K 38/17* | (2006.01) | |
| *A61K 38/00* | (2006.01) | |

(52) U.S. Cl.
CPC .......... *A61K 38/162* (2013.01); *A61K 9/0019* (2013.01); *A61K 38/1716* (2013.01); *C07K 14/005* (2013.01); *A61K 38/00* (2013.01); *C07K 2319/02* (2013.01); *C07K 2319/30* (2013.01); *C12N 2795/14022* (2013.01)

(58) Field of Classification Search
CPC .. C07K 14/01; C07K 14/005; C07K 2319/30; C07K 2317/52; C07K 2317/76; C07K 2319/00; C07K 16/005; C07K 16/46; C07K 14/4711; C07K 2316/52; A61K 38/162; A61K 48/00; A61K 2039/505; A61K 47/48376; A61K 47/48384; A61K 47/48661; C12N 2750/00033; C12N 2750/00022
See application file for complete search history.

(56) References Cited

U.S. PATENT DOCUMENTS

| | | | |
|---|---|---|---|
| 3,941,763 A | 3/1976 | Sarantakis | |
| 4,215,051 A | 7/1980 | Schroeder et al. | |
| 5,252,714 A | 10/1993 | Harris et al. | |
| 5,480,981 A | 1/1996 | Goodwin et al. | |
| 5,808,029 A | 9/1998 | Brockhaus et al. | |
| 6,686,179 B2 | 2/2004 | Fleer et al. | |
| 7,208,147 B2 | 4/2007 | Carr et al. | |
| 7,867,487 B2 | 1/2011 | Solomon et al. | |
| 8,022,270 B2 | 9/2011 | Dickey et al. | |
| 9,493,515 B2* | 11/2016 | Krishnan | A61K 38/162 |
| 9,688,728 B2* | 6/2017 | Krishnan | A61K 38/162 |
| 9,988,444 B2* | 6/2018 | Fisher | C07K 14/4711 |
| 2002/0052311 A1 | 5/2002 | Solomon et al. | |
| 2007/0269435 A1 | 11/2007 | Gillies et al. | |
| 2009/0105090 A1 | 4/2009 | Uchiyama | |
| 2009/0180991 A1 | 7/2009 | Solomon et al. | |
| 2009/0304726 A1 | 12/2009 | Solomon et al. | |
| 2009/0317324 A1 | 12/2009 | Solomon et al. | |
| 2009/0324554 A1 | 12/2009 | Solomon et al. | |
| 2010/0137420 A1 | 6/2010 | Nath | |
| 2011/0142803 A1 | 6/2011 | Solomon et al. | |
| 2011/0182948 A1 | 7/2011 | Solomon et al. | |
| 2014/0335016 A1 | 11/2014 | Krishnan | |
| 2015/0376239 A1 | 12/2015 | Krishnan et al. | |
| 2016/0009766 A1 | 1/2016 | Krishnan et al. | |

FOREIGN PATENT DOCUMENTS

| | | |
|---|---|---|
| EP | 0 154 316 B1 | 9/1989 |
| EP | 0 401 384 B1 | 3/1996 |

(Continued)

OTHER PUBLICATIONS

Muir et al. Modification of N-glycosylation sites allows secretion of bacterial chondroitinase ABC from mammalian cells. J Biotechnol . Jan. 15, 2010;145(2):103-10. doi: 10.1016/j.jbiotec.2009.11.002. Epub Nov. 10, 2009.*

(Continued)

*Primary Examiner* — Gregory S Emch
(74) *Attorney, Agent, or Firm* — Finnegan, Henderson, Farabow, Garrett & Dunner, LLP

(57) ABSTRACT

The invention relates to polypeptides that comprise a portion of filamentous bacteriophage gene 3 protein (g3p) sufficient to bind to and/or disaggregate amyloid, e.g., the N1-N2 portion of g3p and mutants and fragments thereof, wherein that g3p amino acid sequence has been modified through amino acid deletion, insertion or substitution to remove a putative glycosylation signal. The invention further relates to such polypeptides that are also modified through additional amino acid substitution to be substantially less immunogenic than the corresponding wild-type g3p amino acid sequence when used in vivo. The polypeptides of the invention retain their ability to bind and/or disaggregate amyloid. The invention further relates to the use of these g3p-modified polypeptides in the treatment and/or prevention of diseases associated with misfolding or aggregation of amyloid.

11 Claims, 11 Drawing Sheets
Specification includes a Sequence Listing.

(56) References Cited

FOREIGN PATENT DOCUMENTS

| WO | WO 92/16221 A1 | 10/1992 | | |
|----|----|----|----|----|
| WO | WO 95/34326 A1 | 12/1995 | | |
| WO | WO 98/52976 A1 | 11/1998 | | |
| WO | WO 00/34317 A2 | 6/2000 | | |
| WO | WO 02/074243 A2 | 9/2002 | | |
| WO | WO 2004/018685 A2 | 3/2004 | | |
| WO | WO 2006/083795 A1 | 8/2006 | | |
| WO | WO 2007/094003 A2 | 8/2007 | | |
| WO | WO 2008/011503 A2 | 1/2008 | | |
| WO | WO 2008/044032 A2 | 4/2008 | | |
| WO | WO 2009/143465 A1 | 11/2009 | | |
| WO | WO 2009/143470 A1 | 11/2009 | | |
| WO | WO 2010/060073 A2 | 5/2010 | | |
| WO | WO 2011/084714 A2 | 7/2011 | | |
| WO | WO 2012/125555 A1 | 9/2012 | | |
| WO | WO 2013/082114 A1 | 6/2013 | | |
| WO | WO 2014/055515 A1 | 4/2014 | | |
| WO | WO-2014055515 A1 * | 4/2014 | ........... | A61K 38/162 |
| WO | WO 2014/193935 A1 | 12/2014 | | |
| WO | WO 2016/090022 A1 | 6/2016 | | |

OTHER PUBLICATIONS

Aguib et al. (2009) "Autophagy induction by trehalose counteracts cellular prion infection" *Autophagy*, 5(3):361-369.

Aguzzi & O-Connor (2010) "Protein aggregation diseases: pathogenicity and therapeutic perspectives" *Nature Reviews: Drug Discovery*, 9:237-48.

Aruffo et al. (1990) "CD44 Is the Principal Cell Surface Receptor for Hyaluronate" *Cell*, 61:1303-13.

Ashkenazi et al. (1991) "Protection against endotoxic shock by a tumor necrosis factor receptor immunoadhesin" *Proc. Natl. Acad. Sci. USA*, 88:10535-39.

Beck et al. (1978) "Nucleotide sequence of bacteriophage fd DNA" *Nucleic Acids Research*, 5(12):4495-503.

Bennett et al. (1991) "Extracellular Domain-IgG Fusion Proteins for the Three Human Natriuretic Peptide Receptors" *J. Biol. Chem.* 266(34):23060-67.

Byrn et al. (Apr. 1990) "Biological properties of a CD4 immunoadhesin" *Nature*, 344:667-70.

Capon et al. (Feb. 1989) "Designing CD4 immunoadhesins for AIDS therapy" *Nature*, 337:525-31.

Cascales et al., (2007) "Colicin Biology" *Microbiol. Mol. Biol. Rev.*, 71(1):158-229.

Chalupny et al. (1992) "T-cell activation molecule 4-1BB binds to extracellular matrix proteins" *Proc. Natl. Acad. Sci. USA*, 89:10360-64.

Chang and Kuret (2008) "Detection and Quantification of Tau Aggregation Using a Membrane Filter Assay" *Anal. Biochem.*, 373(2):330-6. NIH Public Access Author Manuscript; available in PMC Feb. 15, 2009 (13 pages).

Chiti & Dobson (2006) "Protein Misfolding, Functional Amyloid, and Human Disease" *Annu. Rev. Biochem.*, 75:333-66.

Coruzzi et al. (1984) "Tissue-specific and light-regulated expression of a pea nuclear gene encoding the small subunit of ribulose-1,5-bisphosphate carboxylase" *EMBO J.*, 3:1671-79.

Darocha-Souto et al. (2011) "Brain Oligomeric β-Amyloid but Not Total Amyloid Plaque Burden Correlates With Neuronal Loss and Astrocyte Inflammatory Response in Amyloid Precursor Protein/Tau Transgenic Mice" *J. Neuropathol. Exp. Neurol.*, 70(5):360-76. NIH Public Access Author Manuscript; available in PMC Jul. 29, 2013 (26 pages).

Dehay et al. (2015) "Targeting α-synuclein for treatment of Parkinson's disease: mechanistic and therapeutic considerations" *Lancet Neurol.*, 14:855-866.

Deng and Perham (2002) "Delineating the Site of Interaction on the pill Protein of Filamentous Bacteriophage fd with the F-pilus of *Escherichia coli*" *J. Mol. Biol.*, 319:603-14.

Devlin et al. (1990) "Random Peptide Libraries: A Source of Specific Protein Binding Molecules" *Science*, 249:404-06.

Dimant et al. (2009) "Modulation effect of filamentous phage on alpha-synuclein aggregation" *Biochem. Biophys. Res. Commun.*, 383(4):491-496.

Duyckaerts et al. (2008) "Alzheimer disease models and human neuropathology: similarities and differences" *Acta Neuropathol.*, 115:5-38.

Eckert et al. (2007) "A Conformational Unfolding Reaction Activates Phage fd for the Infections of *Escherichia coli*" *J. Mol. Biol.*, 373(2):452-461.

Eichner and Radford (2011) "A Diversity of Assembly Mechanisms of a Generic Amyloid Fold" *Mol. Cell*, 43:8-18.

Fisher et al. (2011) "NPT001: A Novel Therapeutic Approach for Reducing Levels of Both B-Amyloid Plagues and Neurofibrillary Tangles in Alzheimer's Disease" *Journal of Nutrition, Health & Aging*,15:S26.

Gascoigne et al. (1987) "Secretion of a chimeric T-cell receptor-immunoglobulin protein" *Proc. Natl. Acad. Sci. USA*, 84:2936-40.

Gentz et al. (1989) "Bioassay for trans-activation using purified human immunodeficiency virus tat-encoded protein: Trans-activation requires mRNA synthesis" *Proc. Natl. Acad. Sci. USA*, 86:821-24.

Gurley et al. (1986) "Upstream Sequences Required for Efficient Expression of a Soybean Heat Shock Gene" *Mol. Cell. Biol.*, 6:559-65.

Heiseke et al. (2009) "Lithium induces clearance of protease resistant prion protein in prion-infected cells by induction of autophagy" *J. Neurochem.*, 109:25-34.

Hill and Petersen (1982) "Nucleotide sequence of bacteriophage f1 DNA" *J. Virol.*, 44(1):32-46.

Hoffmann-Thoms et al. (May 2013) "Initiation of Phage Infection by Partial Unfolding and Prolyl Isomerization" *J. Biol. Chem.*, 288(18):12979-91.

Holliger et al. (1999) "Crystal Structure of the Two N-terminal Domains of g3p from Filamentous Phage fd at 1.9 Å Evidence for Conformational Lability" *J. Mol. Biol.*, 288(4):649-57.

Hsiao et al. (1996) "Correlative Memory Deficits, Aβ Elevation, and Amyloid Plaques in Transgenic Mice" *Science*, 274:99-102.

Hughes (2004) "The value of spontaneous alternation behavior (SAB) as a test of retention in pharmacological investigations of memory" *Neurosci. Biobehav. Rev.*, 28:497-505.

International Patent Application No. PCT/US2012/066793, filed Nov. 28, 2012, by Neurophage Pharmaceuticals, Inc.: International Preliminary Report on Patentability, dated Feb. 6, 2014.

International Patent Application No. PCT/US2012/066793, filed Nov. 28, 2012, by Neurophage Pharmaceuticals, Inc.: International Search Report and Written Opinion, dated Apr. 19, 2013.

International Patent Application No. PCT/US2013/062862, filed Oct. 1, 2013, by Neurophage Pharmaceuticals, Inc.: International Search Report and Written Opinion, dated Feb. 24, 2014.

International Patent Application No. PCT/US2014/039760, filed May 28, 2014, by Neurophage Pharmaceuticals, Inc.: International Search Report and Written Opinion, dated Nov. 3, 2014.

International Patent Application No. PCT/US2014/039760, filed May 28, 2014, by Neurophage Pharmaceuticals, Inc.: Written Opinion of the International Preliminary Examining Authority, dated May 15, 2015.

International Patent Application No. PCT/US2014/039760, filed May 28, 2014, by Neurophage Pharmaceuticals, Inc.: International Preliminary Report on Patenability, dated Aug. 14, 2015.

International Patent Application No. PCT/US2015/063476, filed Dec. 2, 2015, by Neurophage Pharmaceuticals, Inc.: International Search Report and Written Opinion, dated Oct. 26, 2016.

International Patent Application No. PCT/US2015/063476, filed Dec. 2, 2015, by Neurophage Pharmaceuticals, Inc.: Written Opinion of the International Preliminary Examining Authority, dated Oct. 26, 2016.

Josephs et al. (2011) "Neuropathological background of phenotypical variability in frontotemporal dementia" *Acta Neuropathol.*, 122:137-53.

(56) References Cited

OTHER PUBLICATIONS

Kather et al. (2005) "A Stable Disulfide-free Gene-3-protein of Phage fd Generated by In vitro Evolution" *J. Mol. Biol.*, 354(3):666-678.
Kerr et al (2001) "Lysostaphin expression in mammary glands confers protection against staphylococcal infection in transgenic mice" *Nature Biotechnol.*, 19(1):66-70.
King et al. (1999) "Progressive and gender-dependent cognitive impairment in the APP$_{sw}$ transgenic mouse model for Alzheimer's disease" *Brain Res.*, 103:145-62.
Kingstedt and Nilsson (2012) "Luminescent conjugated poly- and oligo-thiophenes: optical ligands for spectral assignment of a plethora of protein aggregates" *Biochem. Soc. Trans.*, 40(4):704-710.
Kosik et al. (1986) "Microtubule-associated protein tau (tau) is a major antigenic component of paired helical filaments in Alzheimer disease" *Proc. Natl. Acad. Sci. USA*, 83(11):4044-48.
Krishnan et al. (2014) "A Bacteriophage Capsid Protein Provides a General Amyloid Interaction Motif (GAIM) That Binds and Remodels Misfolded Protein Assemblies" *J. Mol. Biol.*, 426:2500-19.
Kurschner et al. (1992) "Construction, Purification, and Characterization of New Interferon γ (IFNγ) Inhibitor Proteins" *J. Biol. Chem.*, 267:9354-60.
Lalonde et al. (2012) "Neurologic and motor dysfunctions in APP transgenic mice" *Rev. Neurosci.*, 23(4):363-79. NIH Public Access Author Manuscript; available in PmMC Jan. 1, 2013 (25 pages).
Lalonde & Strazielle (2012) "Brain regions and genes affecting myoclonus in animals" *Neurosci. Res.*, 74(2):69-79.
Lee et al. (2001) "Neurodegenerative Tauopathies" *Annu. Rev. Neurosci.*, 24:1121-59.
Lesslauer et al. (1991) "Recombinant soluble tumor necrosis factor receptor proteins protect mice from lipopolysaccharide-induced lethality" *Eur. J. Immunol.*, 21(11):2883-86.
Lewis et al. (2000) "Neurofibrillary tangles, amyotrophy and progressive motor disturbance in mice expressing mutant (P301L) tau protein" *Nat. Genet.*, 25:402-5.
Li et al. (2015) "Trehalose Decreases Mutant SOD1 Expression and Alleviates Motor Deficiency in Early But Not End-Stage Amyotrophic Lateral Sclerosis in a SOD1-G93A Mouse Model" *Neurosci.*, 298:12-25.
Lin et al. (2011) "Inhibition of Bacterial Conjugation by Phage M13 and Its Protein g3p: Quantitative Analysis and Model" *PLoS ONE*,6(5):e19991. doi:10.1371/journal.pone.0019991 (11 pages).
Linsley et al. (1991) "Binding of the B cell activation antigen B7 to CD28 costimulates T cell proliferation and interleukin 2 mRNA accumulation" *J. Exp. Med.*, 173:721-30.
Linsley et al. (1991) "CTLA-4 Is a Second Receptor for the B Cell Activation Antigen B7" *J. Exp. Med.*, 174:561-69.
Liu et al. (2005) "Trehalose differentially inhibits aggregation and neurotoxicity of beta-amyloid 40 and 42" *Neurobiol. Dis.*, 20:74-81.
Lo et al. (1998) "High level expression and secretion of Fc-X fusion proteins in mammalian cells" *Protein Engineering*, 11(6):495-500.
Logan and Shenk (1984) "Adenovirus tripartite leader sequence enhances translation of mRNAs late after infection" *Proc. Natl. Acad. Sci. USA*, 81:3655-59.
Lorenz et al. (2011) "The Filamentous Phages fd and IF1 Use Different Mechanisms to Infect *Escherichia coli*" *J. Mol. Biol.*, 405:989-1003.
Lou et al. (2012) "Probing of C-terminal lysine variation in a recombinant monoclonal antibody production using Chinese hamster ovary cells with chemically defined media" *Biotechnol. Bioeng.*, 109(9):2306-15.
Lubkowski et al. (1998) "Filamentous phage infection: crystal structure of g3p in complex with its coreceptor, the C-terminal domain of ToIA" *Structure*, 7(6):711-22.
Mackett et al. (1982) "Vaccinia virus: A selectable eukaryotic cloning and expression vector" *Proc. Natl. Acad. Sci. USA*, 79:7415-19.
Mackett et al. (1984) "General Method for Production and Selection of Infectious Vaccinia Virus Recombinants Expressing Foreign Genes" *J. Virol.*, 49:857-64.

Martin and Schmid (2003) "Evolutionary Stabilization of the Gene-3-protein of Phage fd Reveals the Principles that Govern the Thermodynamic Stability of Two-domain Proteins" *J. Mol. Biol.*, 328:863-75.
Marvin (1998) "Filamentous phage structure, infection and assembly" *Curr. Opin. in Struct. Biol.*, 8:150-8.
Masliah et al. (2000) "Dopaminergic Loss and Inclusion Body Formation in α-Synuclein Mice: Implications for Neurodegenerative Disorders" *Science*, 287:1265-69.
Mckhann et al. (2011) "The diagnosis of dementia due to Alzheimer's disease: Recommendations from the National Institute on Aging and the Alzheimer's Association workgroup" [Article in Press] *Alzheimer's & Dementia*, doi:10.1016/j.jalz.2011.03.005, 7 pages; final publication in 7(3):263-9.
Mega et al. (1996) "The spectrum of behavioral changes in Alzheimer's disease" *Neurology*, 46:130-5.
Messing (2016) "Phage M13 for the treatment of Alzheimer and Parkinson disease" *Gene*, 583:85-89.
Messing and Ayer, "Enterobacteria phage M13 isolate WT variety Rutgers, complete genome" GenBank Database Accession No. JX412914, Version GI:401823911; submitted Jul. 20, 2012.
Muir, E.M. et al. (2010) "Modification of N-glycosylation sites allows secretion of bacterial chondroitinase ABC from mammalian cells" J. Biotechnol., 145(2):103-110.
Olofsson et al. (2006) "The Solvent Protection of Alzheimer Amyloid-β-(1-42) Fibrils as Determined by Solution NMR Spectroscopy" *J. Biol. Chem.*, 281(1):477-83.
Panicali et al. (1982) "Construction of poxviruses as cloning vectors: Insertion of the thymidine kinase gene from herpes simplex virus into the DNA of infectious vaccinia virus" *Proc. Natl. Acad. Sci. USA*, 79:4927-31.
Pankiewicz et al. (2006) "Clearance and prevention of prion infection in cell culture by anti-PrP antibodies" NIH Public Access Author Manuscript, available in PMC Jan. 22, 2007. Final publication in: *Eur. J. Neurosci.*, 23:2635-47.
Peppel et al. (1991) "A tumor necrosis factor (TNF) receptor-IgG heavy chain chimeric protein as a bivalent antagonist of TNF activity" *J. Exp. Med.*, 174:1483-89.
Perrier et al. (2004) "Anti-Prp antibodies block PrP$^{sc}$ replication in prion-infected cell cultures by accelerating PrP$^c$ degradation" *J. Neurochem.*, 84:454-63.
Petkova et al. (2005) "Self-propagating, molecular-level polymorphism in Alzheimer's β-amyloid fibrils" *Science*, 307:262-65.
Rasched and Oberer (1986) "Ff Coliphages: Structural and Functional Relationships" *Microbiol. Rev.*, 50:401-27.
REFSEQ database Accession No. NC_003287.2, version GI:56718463, "Enterobacteria phage M13, complete genome" circular PHG Apr. 17, 2009 (7 pages).
Resnick and Sojkova (2011) "Amyloid imaging and memory change for prediction of cognitive impairment" *Alzheimer's Res Ther.*, 3:3, doi:10.1186/alzrt62 [online]. Retrieved from: http://alzres.com/content/3/1/3.
Robinson et al. (2015) "Drugs and drug delivery systems targeting amyloid-β in Alzheimer's disease" *Mol. Sci.*, 2(3):332-358.
Sadowski et al. (2009) "Anti-PrP Mab 6D11 suppresses PrP$^{sc}$ replication in prion infected myeloid precursor line FDC-P1/22L and in the lymphoreticular system in vivo" NIH Public Access Author Manuscript, available Jul. 20, 2009. Final publication in: *Neurobiol Dis.*, 34(2): 267-78.
Sánchez et al. (2011) "Aβ40 and Aβ42 Amyloid Fibrils Exhibit Distinct Molecular Recycling Properties" *J. Am. Chem. Soc.*, 133:6505-08.
Sarkar et al. (2005) "Lithium induces autophagy by inhibiting inositol monophosphatase" *J. Cell Biol.*, 170(7):1101-11.
Sarkar et al. (2007) "Trehalose, a Novel mTOR-independent Autophagy Enhancer, Accelerates the Clearance of Mutant Huntingtin and -α-Synuclein" *J. Biol. Chem.*, 282(8):5641-52.
Sato et al. (2006) "Inhibitors of Amyloid Toxicity Based on β-sheet Packing of Aβ40 and Aβ42" *Biochemistry*, 45:5503-16.
Sciarretta et al. (2006) "Peptide-Based Inhibitors of Amyloid Assembly" *Meth. Enzymol.*, 413:273-312.
Scott and Smith (1990) "Searching for Peptide Ligands with an Epitope Library" *Science*, 249:386-90.

(56) References Cited

OTHER PUBLICATIONS

Simonsen and Levinson (1983) "Isolation and expression of an altered mouse dihydrofolate reductase cDNA" *Proc. Natl. Acad. Sci. USA*, 80:2495-99.
Smith et al. (1983) "Molecular Engineering of the *Autographa californica* Nuclear Polyhedrosis Virus Genome: Deletion Mutations Within the Polyhedrin Gene" *J. Virol.*, 46:584-93.
Smith et al. (1997) "Phage display" *Chem. Rev.*, 97:391-410.
Stamenkovic et al. (1991) "The B Lymphocyte Adhesion Molecule CD22 Interacts with Leukocyte Common Antigen CD45RO on T Cells and α2-6 Sialyltransferase, CD75, on B Cells" *Cell*, 66:1133-44.
Stassen et al. (1992) "Nucleotide Sequence of the Genome of the Filamentous Bacteriophage I2-2: Module Evolution of the Filamentous Phage Genome" *J. Mol. Evol.*, 34:141-52.
Sterniczuk et al. (2010) "Characterization of the 3xTg-AD mouse model of Alzheimer's disease: Part 1. Circadian changes" *Brain Res.*, 1348:139-48.
Sterniczuk et al. (2010) "Characterization of the 3xTg-AD mouse model of Alzheimer's disease: Part 2. Behavioral and cognitive changes" *Brain Res.*, 1348:149-55.
Stine et al. (2003) "In Vitro Characterization of Conditions for Amyloid-β Peptide Oligomerization and Fibrillogenesis" *J. Biol. Chem.*, 278(13):11612-22.
Stine et al. (2011) "Preparing synthetic Aβ in different aggregation states" HHS Public Access Author Manuscript, available Aug. 26, 2013, PMCID: PMC3752843. Final publication in: *Methods Mol. Biol.*, 670: 13-32.
Sunde et al. (1997) "Common Core Structure of Amyloid Fibrils by Synchrotron X-ray Diffraction" *J. Mol. Biol.*, 273:729-39.
Takamatsu et al. (1987) "Expression of bacterial chloramphenicol acetyltransferase gene in tobacco plants mediated by TMV-RNA" *EMBO J.*, 6:307-11.
Terpe (2003) "Overview of tagg protein fusions: from molecular and biochemical fundamentals to commercial systems" *Appl. Microbiol. Biotechnol.*, 60:523-33.
Tjernberg et al. (1996) "Arrest of β-Amyloid Fibril Formation by a Pentapeptide Ligand" *J. Biol. Chem.*, 271(12):8545-48.
Traunecker et al. (May 1989) "Highly efficient neutralization of HIV with recombinant CD4-immunoglobulin molecules" *Nature*, 339:68-70.
UNIPROT Accession No. O80297 (Entry date: Jul. 15, 1999) "Protein: Attachment protein G3P. Organism: Enterobacteria phage If1 (Bacteriophage If1)." [online]. Retrieved from the Internet: http://www.uniprot.org/uniprot/O80297.
UNIPROT Accession No. P03661 (Entry date: Jul. 21, 1986) "Protein: Attachment protein G3P. Organism: Enterobacteria phage fd (Bacteriophage fd)." [online]. Retrieved from the Internet: http://www.uniprot.org/uniprot/P03661.
UNIPROT Accession No. P03663 (Entry date: Jul. 21, 1986) "Protein: Attachment protein G3P. Organism: Enterobacteria phage IKe (Bacteriophage IKe)." [online]. Retrieved from the Internet: http://www.uniprot.org/uniprot/P03663.
UNIPROT Accession No. P15415 (Entry date: Apr. 1, 1990) "Protein: Attachment protein G3P. Organism: Enterobacteria phage I2-2 (Bacteriophage I2-2)." [online]. Retrieved from the Internet: http://www.uniprot.org/uniprot/P15415.
UNIPROT Accession No. P69168 (Entry date: Jul. 21, 1986) "Protein: Attachment protein G3P. Organism: Enterobacteria phage M13 (Bacteriophage M13)." [online]. Retrieved from the Internet: . http://www.uniprot.org/uniprot/P69168.
UNIPROT Accession No. P69169 (Entry date: Jul. 21, 1986) "Protein: Attachment protein G3P. Organism: Enterobacteria phage f1 (Bacteriophage f1)." [online]. Retrieved from the Internet: http://www.uniprot.org/uniprot/P69169.
Van Wezenbeek et al. (1980) "Nucleotide sequence of the filamentous bacteriophage M13 DNA genome: comparison with phage fd" *Gene*, 11:129-48.
Van Wezenbeek et al., "Structural protein [Enterobacteria phage M13]" NCBI Protein Sequence Database Accession No. NP_510891. 1, Version GI:17426224; submitted Dec. 8, 2001.
Wang et al. (2010) "Generating a Prion with Bacterially Expressed Recombinant Prion Protein" *Science*, 327:1132-35.
Wang et al. (2010) "Degradation of TDP-43 and its pathogenic form by autophagy and the ubiquitin-proteasome system" *Neurosci. Lett.*, 469:112-116.
Wanker et al. (1999) "Membrane Filter Assay for Detection of Amyloid-like Polyglutamine-Containing Protein Aggregates" *Methods Enzymol.*, 309:375-86.
Watson et al. (1990) "A homing receptor-IgG chimera as a probe for adhesive ligands of lymph node high endothelial venules" *J. Cell. Biol.*, 110:2221-29.
Watson et al. (Jan. 1991) "Neutrophil influx into an inflammatory site inhibited by a soluble homing receptor-IgG chimaera" *Nature*, 349:164-67.
Whittemore et al. (2005) "Hydrogen-Deuterium (H/D) Exchange Mapping of $A\beta_{1-40}$ Amyloid Fibril Secondary Structure Using Nuclear Magnetic Resonance Spectroscopy" *Biochemistry*, 44:4434-41.
Wilcock et al. (2004) "Passive Amyloid Immunotherapy Clears Amyloid and Transiently Activates Microglia in a Transgenic Mouse Model of Amyloid Deposition" *J. Neurosci.*, 24(27):6144-51.
Yamaguchi et al. (2004) "Core and Heterogeneity of β2-Microglobulin Amyloid Fibrils as Revealed by H/D Exchange" *J. Mol. Biol.*, 338:559-71.
Zettmeissl et al. (1990) "Expression and characterization of human CD4: Immunoglobulin fusion proteins" *DNA Cell Biol.*, 9(5):347-53.
Zhao et al. (2012) "Tagged and untagged TRAIL show different activity against tumor cells" *Oncol. Lett.*, 4:1301-4.
Zheng et al. (1995) "Administration of noncytolytic IL-10/Fc in murine models of lipopolysaccharide-induced septic shock and allogeneic islet transplantation" *J. Immunol.*, 154:5590-5600.

\* cited by examiner

FIG. 1 (SEQ ID NO:1)

```
  1                                                                    22
  A   E   T   V   E   S   C   L   A   K   P   H   T   E   N   S   F   T   N   V   W   K
 23                                                                    44
  D   D   K   T   L   D   R   Y   A   N   Y   E   G   C   L   W   N   A   T   G   V   V
 45                                                                    66
  V   C   T   G   D   E   T   Q   C   Y   G   T   W   V   P   I   G   L   A   I   P   E
 67                                                                    88
  N   E   G   G   G   S   E   G   G   G   S   E   G   G   G   S   E   G   G   G   T   K
 89                                                                   110
  P   P   E   Y   G   D   T   P   I   P   G   Y   T   Y   I   N   P   L   D   G   T   Y
111                                                                   132
  P   P   G   T   E   Q   N   P   A   N   P   N   P   S   L   E   E   S   Q   P   L   N
133                                                                   154
  T   F   M   F   Q   N   N   R   F   R   N   R   Q   G   A   L   T   V   Y   T   G   T
155                                                                   176
  F   T   Q   G   T   D   P   V   K   T   Y   Y   Q   Y   T   P   V   S   S   K   A   M
177                                                                   198
  Y   D   A   Y   W   N   G   K   F   R   D   C   A   F   H   S   G   F   N   E   D   P
199                                                                   220
  F   V   C   E   Y   Q   G   Q   S   S   D   L   P   Q   P   P   P   V   N   A   G   G
221                                                                   242
  S   G   G   G   S   G   G   G   S   E   G   G   G   S   E   G   G   G   S   E   G   G
243                                                                   264
  G   S   E   G   G   G   S   G   G   G   S   G   G   G   S   G   S   S   A   M   V   R   S   D   K   T
265                                                                   286
  H   T   C   P   P   C   P   A   P   E   L   L   G   G   P   S   V   F   L   F   P   P
287                                                                   308
  K   P   K   D   T   L   M   I   S   R   T   P   E   V   T   C   V   V   V   D   V   S
309                                                                   330
  H   E   D   P   E   V   K   F   N   W   Y   V   D   G   V   E   V   H   N   A   K   T
331                                                                   352
  K   P   R   E   E   Q   Y   N   S   T   Y   R   V   V   S   V   L   T   V   L   H   Q
353                                                                   374
  D   W   L   N   G   K   E   Y   K   C   K   V   S   N   K   A   L   P   A   P   I   E
375                                                                   396
  K   T   I   S   K   A   K   G   Q   P   R   E   P   Q   V   Y   T   L   P   P   S   R
397                                                                   418
  E   E   M   T   K   N   Q   V   S   L   T   C   L   V   K   G   F   Y   P   S   D   I
419                                                                   440
  A   V   E   W   E   S   N   G   Q   P   E   N   N   Y   K   T   T   P   P   V   L   D
441                                                                   462
  S   D   G   S   F   F   L   Y   S   K   L   T   V   D   K   S   R   W   Q   Q   G   N
463                                                                   484
  V   F   S   C   S   V   M   H   E   A   L   H   N   H   Y   T   Q   K   S   L   S   L
485
  S   P   G   K
```

FIG. 2 (SEQ ID NO:2)

```
  1                                                                              22
  A  E  T  V  E  S  C  L  A  K  P  H  T  E  N  S  F  T  N  V  W  K
 23                                                                              44
  D  D  K  T  L  D  R  Y  A  N  Y  E  G  C  L  W  N  A  T  G  V  V
 45                                                                              66
  V  C  T  G  D  E  T  Q  C  Y  G  T  W  V  P  I  G  L  A  I  P  E
 67                                                                              88
  N  E  G  G  G  S  E  G  G  G  S  E  G  G  G  S  E  G  G  G  T  K
 89                                                                             110
  P  P  E  Y  G  D  T  P  I  P  G  Y  T  Y  I  N  P  L  D  G  T  Y
111                                                                             132
  P  P  G  T  E  Q  N  P  A  N  P  N  P  S  L  E  E  S  Q  P  L  N
133                                                                             154
  T  F  M  F  Q  N  N  R  F  R  N  R  Q  G  A  L  T  V  Y  T  G  T
155                                                                             176
  F  T  Q  G  T  D  P  V  K  T  Y  Y  Q  Y  T  P  V  S  S  K  A  M
177                                                                             198
  Y  D  A  Y  W  N  G  K  F  R  D  C  A  F  H  S  G  F  N  E  D  P
199                                                                             220
  F  V  C  E  Y  Q  G  Q  S  S  D  L  P  Q  P  P  A  N  A  G  G  E
221                                                                             242
  S  G  G  G  S  G  G  G  S  E  G  G  G  S  E  G  G  G  S  E  G  G
243                                                                             262
  G  S  E  G  G  G  S  G  G  G  S  G  S  G  A        R  S  D  K  T
263                                                                             284
  H  T  C  P  P  C  P  A  P  E  L  L  G  G  P  S  V  F  L  F  P  P
285                                                                             306
  K  P  K  D  T  L  M  I  S  R  T  P  E  V  T  C  V  V  V  D  V  S
307                                                                             328
  H  E  D  P  E  V  K  F  N  W  Y  V  D  G  V  E  V  H  N  A  K  T
329                                                                             350
  K  P  R  E  E  Q  Y  N  S  T  Y  R  V  V  S  V  L  T  V  L  H  Q
351                                                                             372
  D  W  L  N  G  K  E  Y  K  C  K  V  S  N  K  A  L  P  A  P  I  E
373                                                                             394
  K  T  I  S  K  A  K  G  Q  P  R  E  P  Q  V  Y  T  L  P  P  S  R
395                                                                             416
  E  E  M  T  K  N  Q  V  S  L  T  C  L  V  K  G  F  Y  P  S  D  I
417                                                                             438
  A  V  E  W  E  S  N  G  Q  P  E  N  N  Y  K  T  T  P  P  V  L  D
439                                                                             460
  S  D  G  S  F  F  L  Y  S  K  L  T  V  D  K  S  R  W  Q  Q  G  N
461                                                                             482
  V  F  S  C  S  V  M  H  E  A  L  H  N  H  Y  T  Q  K  S  L  S  L
483
  S  P  G  K
```

SEQ ID NO: 3

ATGTACAGGATGCAACTCCTGTCTCTTGCATTGCACTAAGTCTTGCACTTGTCAGAATTCGATGGCTGAAACTGTTGAAAG
TTGTTTAGCAAAACCCCATACAGAAAATTCATTTACTAACGTCTGGAAAGACGACAAAACTTTAGATCGTTACGCTAACT
ATGAGGGCTGTCTGTGGAATGCTACAGGCGGTTGTAGTTTGTTACGGTTTGACGAAACTCAGTGTTACGGTACATGGTTCCT
ATTGGGCTTGCTATCCCTGAAAATGAGGGTGGCGGTTCTGAGGGTGGCGGTTCTGAGGGTGGCGGTTATCCGCCTG
TACTAAACCTCCTGAGTACGGTGATACACCTATTCCGGGCTATACTTATATCAACCCTCTCGACGGCACTTATCCGCCTG
GTACTGAGCAAAACCCCGCTAATCCTAATCCTTGTTTTATACGGAGTCTCAGCCTTCTTAATACTTTCATGTTTCAGAATAAT
AGGTTCCGAAATAGGCAGGGGCATTAACTGTTTATACGGGCACTGTTACTCAAGGCACTGACCCCGTTAAAACTTATTA
CCAGTACACTCCTGTATCATCAAAAGCCATGTATGAATTCAGAGACTGCGCTTTCCATTCTG
GCTTTAATGAGGATCCATTCGTTTGTGAATATCAAGGCCAATCCTGTCTGACCGTCGACCCTCCTGTCAATGCTGGCGGC
GGCTCTGGTGGTGGTTCTGGCGGTCTCTGGTTCCGGTGCCATGGGTGGCGGTTAGATCTGACAAAACTCACACATCCAGCAC
AGGCGGTTCCGGTGGTGGGGGACCGTCAGTCTTCCCTCTTCCCCCCAAGGACACCCCTCATGATCTCCCGGACCCCTGAGC
CTGAACTCGCGGTGGTGGTGGACGTGAGCCACGAAGACCCTGAGGTCAAGTTCAACTGGTACGTGGACGGCGTGGAGGTGCA
TAATGCCAAGACAAAGCCGCGGGAGGAGCAGTACAACAGCACGTACCGTGTGGTCAGCGTCCTCACCGTCCTGCACCAGG
ACTGGCTGAATGGCAAGGAGTACAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCGCCGGGAGGAGATGACCAAGAACCAGGTCAGCCT
GACCTGCCTGGTCAAAGGCTTCTATCCCAGCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACGCAGAAGAGCCTCTCCCTGTCTCC
GGGTAAATGA

FIG. 3

SEQ ID NO: 4

ATGTACAGGATGCAACTCCTGTCTTGCATTGCACTAAGTCTTGCACTTGTCACGAATTCGATGGCTGAAACTGTTGAAAG
TTGTTTAGCAAAACCCCATACAGAAAATTCATTTACTAACGTCTGGAAAGACGACAAAACTTTAGATCGTTACGCTAACT
ATGAGGGCTGTCTGTGGAATGCTACAGGCGGTTGTAGTTTGTACTGGTGACGAAACTCAGTGTTACGGTACATGGGTTCCT
ATTGGGCTTGCTATCCCTGAAAATGAGGGTGGCTCTGAGGGTGGCGGTTCTGAGGGTGGCGGTTCTGAGGGTGGCGG
TACTAAACCCTCCTGAGTACGGTGATACACCTATTCCGGGCTATATACTTTATCAACCCTCTCGACGGCACTTATCCGCCTG
GTACTGAGCAAAACCCCGCTAATCCTAATCCTTCTCTTGAGGAGTCTCAGCCTCTTAATACTTTCATGTTTCAGAATAAT
AGGTTCCGAAATAGGCAGGGGCATTAACTGTTTATACGGGCACTGTTACTCAAGGCACTGACCCCGTTAAAACTTATTA
CCAGTACACTCCTGTATCATCAAAAGCCATGTATACGTTACTGGAAACGGTAAATTCAGAGACTGCGCTTTCCATTCTG
GCTTTAATGAGGATCCATTCGTTTGTGAATATCGTTGATGCGCTTACTGAGGGTGCTGCTGAGGGCGGTGGCGGCTCTGAGG
GaGTCTGGTGGTTCCGGCTTCTGGTGGGCTCTGGTTCCCTCTGGTGCCAGATCTGACAAAACTCACACATGCCCAGCACCTGAAC
AGGCGGTTCCGGGGACCCGTCAGTCTTCCCTCTTCCCCCCAAAAGGACACCCTCATGATCTCCCGGACCCCTGAGGTCACA
TCCCTGGGGGTGGTGGACGTGAGCCACGAAGACCCTGAGGTCAAGTTCAACTGGTACGTGGACGGCGTGGAGGTGCATAATGC
CAAGACAAAGCCGCGGAGGAGCAGTACAACAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGACAAGAGCAGGTGGCAGCAGGGG
AACGTCTTCTCATGCTCCGTGATGCACGAGGCTCTGCACAACCACTACACGCAGAAGAGCCTCTCCCTGTCTCCGGGTAA
ATGA

FIG. 4

FIG. 6 (SEQ ID NO:5)

```
  1                                                                    22
  A  E  T  V  E  S  C  L  A  K  P  H  T  E  N  S  F  T  N  V  W  K
 23                                                                    44
  D  D  K  T  L  D  R  Y  A  N  Y  E  G  C  L  W  N  A  C  G  V  V
 45                                                                    66
  V  C  T  G  D  E  T  Q  C  Y  G  X  W  V  P  I  G  L  A  I  P  E
 67                                                                    88
  N  E  G  G  S  E  G  G  G  S  E  G  G  G  S  E  G  G  T  K
 89                                                                   110
  P  P  E  Y  G  D  T  P  I  P  G  Y  T  Y  I  N  P  L  D  G  T  Y
111                                                                   132
  P  P  G  T  E  Q  N  P  A  N  P  N  P  S  L  E  E  S  Q  P  L  N
133                                                                   154
  T  F  M  F  Q  N  N  R  F  R  N  R  Q  G  A  L  T  V  Y  T  G  T
155                                                                   176
  F  T  Q  G  T  D  P  V  K  T  Y  Y  Q  Y  T  P  V  S  S  X  A  M
177                                                                   198
  Y  D  A  Y  W  N  G  K  F  R  D  C  A  F  H  S  G  F  N  E  D  P
199                                                                   220
  F  V  C  E  Y  Q  G  Q  S  S  D  L  P  Q  P  P  A  N  A  G  G  E
221                                                                   242
  S  G  G  S  G  G  G  S  E  G  G  G  S  E  G  G  G  S  E  G  G
243                                                                   262
  G  S  E  G  G  G  S  G  G  G  S  G  S  G  A        R  S  D  K  T
263                                                                   284
  H  T  C  P  P  C  P  A  P  E  L  L  G  G  P  S  V  F  L  F  P  P
285                                                                   306
  K  P  K  D  T  L  M  I  S  R  T  P  E  V  T  C  V  V  V  D  V  S
307                                                                   328
  H  E  D  P  E  V  K  F  N  W  Y  V  D  G  V  E  V  H  N  A  K  T
329                                                                   350
  K  P  R  E  E  Q  Y  N  S  T  Y  R  V  V  S  V  L  T  V  L  H  Q
351                                                                   372
  D  W  L  N  G  K  E  Y  K  C  K  V  S  N  K  A  L  P  A  P  I  E
373                                                                   394
  K  T  I  S  K  A  K  G  Q  P  R  E  P  Q  V  Y  T  L  P  P  S  R
395                                                                   416
  E  E  M  T  K  N  Q  V  S  L  T  C  L  V  K  G  F  Y  P  S  D  I
417                                                                   438
  A  V  E  W  E  S  N  G  Q  P  E  N  N  Y  K  T  T  P  P  V  L  D
439                                                                   460
  S  D  G  S  F  F  L  Y  S  K  L  T  V  D  K  S  R  W  Q  Q  G  N
461                                                                   482
  V  F  S  C  S  V  M  H  E  A  L  H  N  H  Y  T  Q  K  S  L  S  L
483
  S  P  G  K
```

SEQ ID NO:6

```
GGATCTGCGATCGCTCCGGTGCCCGTCAGTGGGCAGAGCGCACATCGCCCACAGTCCCCGAGAAGTTGGGGGGAGGGGTCGGCAATTGAACGGGT
GCCTAGAGAAGGTGGCGCGGGGTAAACTGGGAAAGTGATGTCGTGTACTGGCTCCGCCTTTTTCCCGAGGGTGGGGGAGAACCGTATATAAGTGC
AGTAGTCGCCGTGAACGTTCTTTTTCGCAACGGGTTTGCCGCCAGAACACAGCTGAAGCTTCGAGGGGCTCGCATCTCTCCTTCACGCGCCCGCC
GCCCTACCTGAGGCCGCCATCCACGCCGGTTGAGTCGCGTTCTGCCGCCTCCCGCCTGTGGTGCCTCCTGAACTGCGTCCGCCGTCTAGGTAAGT
TTAAAGCTCAGGTCGAGACCGGGCCTTTGTCCGGCGCTCCCTTGGAGCCTACCTAGACTCAGCCGGCTCTCCACGCTTTGCCTGACCCTGCTTGC
TCAACTCTACGTCTTTGTTTCGTTTTCTGTTCTGCGCCGTTACAGATCCAAGCTGTGACCGGCGCCTACCTGAGATCACCGGcGAAGGAGGGCCA
CCATGTACAGGATGCAACTCCTGTCTTGCATTGCACTAAGTCTTGCACTTGTCACGAATTCGATGGCTGAAACTGTTGAAAGTTGTTTAGCAAAA
CCCCATACAGAAAATTCATTTACTAACGTCTGGAAAGACGACAAAACTTTAGATCGTTACGCTAACTATGAGGGCTGTCTGTGGAATGCTACAGG
CGTTGTAGTTTGTACTGGTGACGAAACTCAGTGTTACGGTCATTGGGTTCCTATTGGGCTTGCTATCCCTGAAAATGAGGGTGGTGGCTCTGAGG
GTGGCGGTTCTGAGGGTGGCGGTTCTGAGGGTGGCGGTACTAAACCTCCTGAGTACGGTGATACACCTATTCCGGGCTATACTTATATCAACCCT
CTCGACGGCACTTATCCGCCTGGTACTGAGCAAAACCCCGCTAATCCTAATCCTTCTCTTGAGGAGTCTCAGCCTCTTAATACTTTCATGTTTCA
GAATAATAGGTTCCGAAATAGGCAGGGGGCATTAACTGTTTATACGGGCACTTTTACTCAAGGCACTGACCCCGTTAAAACTTATTACCAGTACA
CTCCTGTATCATCAAGAGCCATGTATGACGCTTACTGGAACGGTAAATTCAGAGACTGCGCTTTCCATTCTGGCTTTAATGAGGATCCATTCGTT
TGTGAATATCAAGGCCAATCGTCTGACCTGCCTCAACCTCCTGCCAATGCTGGCGGCGAGTCTGGTGGTGGTTCTGGTGGCGGCTCTGAGGGTGG
TGGCTCTGAGGGTGGCGGTTCTGAGGGTGGCGGCTCTGAGGGAGGCGGTTCCGGTGGTGGCTCTGGTTCCGGTGCCAGATCTGACAAAACTCACA
CATGCCCACCGTGCCCAGCACCTGAACTCCTGGGGGGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAACTGGTACGTGGACGGCGTGGAGGTGCATAATGCCAA
GACAAAGCCGCGGGAGGAGCAGTACAACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCTTCCTCTACAGCAAGCTCACCGTGGACAAGA
GCAGGTGGCAGCAGGGGAACGTCTTCTCATGCTCCGTGATGCACGAGGCTCTGCACAACCACTACACGCAGAAGAGCCTCTCCCTGTCTCCGGGT
AAATGAGTGCTAGCTGGCCAGACATGATAAGATACATTGATGAGTTTGGACAAACCACAACTAGAATGCAGTGAAAAAAATGCTTTATTTGTGAA
ATTTGTGATGCTATTGCTTTATTTGTAACCATTATAAGCTGCAATAAACAAGTTAACAACAACAATTGCATTCATTTTATGTTTCAGGTTCAGGG
GGAGGTGTGGGAGGTTTTTTAAAGCAAGTAAAACCTCTACAAATGTGGTATGGAATTAATTCTAAAATACAGCATAGCAAAACTTTAACCTCCAA
ATCAAGCCTCTACTTGAATCCTTTTCTGAGGGATGAATAAGGCATAGGCATCAGGGGCTGTTGCCAATGTGCATTAGCTGTTTGCAGCCTCACCT
TCTTTCATGGAGTTTAAGATATAGTGTATTTTCCCAAGGTTTGAACTAGCTCTTCATTTCTTTATGTTTTAAATGCACTGACCTCCCACATTCCC
TTTTTAGTAAAATATTCAGAAATAATTTAAATACATCATTGCAATGAAAATAAATGTTTTTTATTAGGCAGAATCCAGATGCTCAAGGCCCTTCA
TAATATCCCCCAGTTTAGTAGTTGGACTTAGGGAACAAAGGAACCTTTAATAGAAATTGGACAGCAAGAAAGCGAGCTTCTAGCTTATCCTCAGT
CCTGCTCCTCTGCCACAAAGTGCACGCAGTTGCCGGCCGGGTCGCGCAGGGCGAACTCCCGCCCCACGGCTGCTCGCCGATCTCGGTCATGGCC
GGCCCGGAGGCGTCCCGGAAGTTCGTGGACACGACCTCCGACCACTCGGCGTACAGCTCGTCCAGGCCGCGCACCCACACCCAGGCCAGGGTGTT
GTCCGGCACCACCTGGTCCTGGACCGCGCTGATGAACAGGGTCACGTCGTCCCGGACCACACCGGCGAAGTCGTCCTCACGAAGTCCCGGGAGA
ACCCGAGCCGGTCGGTCCAGAACTCGACCGCTCCGGCGACGTCGCGCGCGGTGAGCACCGGAACGGCACTGGTCAACTTGGCCATGATGGCTCCT
CctgtcaggagaggaaagagaagaaggttagtacaattgCTATAGTGAGTTGTATTATACTATGCAGATATACTATGCCAATGATTAATTGTCAA
ACTAGGGCTGCAgggttcatagtgccactttttcctgcactgccccatctcctgcccacccttccccaggcatagacagtcagtgacttacCAAAC
TCACAGGAGGGAGAAAGGCAGAAGCTTGAGACAGACCCGCGGGACCGCCGAACTGCGAGGGGACGTGGCTAGGGCGGCTTCTTTTATGGTGCGCCG
GCCCTCGGAGGCAGGGCGCTCGGGGAGGCCTAGCGGCCAATCTGCGGTGGCAGGAGGCGGGGCCGAAGGCCGTGCCTGACCAATCCGGAGCACAT
AGGAGTCTCAGCCCCCCGCCCAAAGCAAGGGGAAGTCACGCGCCTGTAGCGCCAGCGTGTTGTGAAATGGGGGCTTGGGGGGGTTGGGGCCCTG
ACTAGTCAAAACAAACTCCCATTGACGTCAATGGGGTGGAGACTTGGAAATCCCCGTGAGTCAAACCGCTATCCACGCCCATTGATGTACTGCCA
AAACCGCATCATCATGGTAATAGCGATGACTAATACGTAGATGTACTGCCAAGTAGGAAAGTCCCATAAGGTCATGTACTGGGCATAATGCCAGG
CGGGCCATTTACCGTCATTGACGTCAATAGGGGGCGTACTTGGCATATGATACACTTGATGTACTGCCAAGTGGGCAGTTTACCGTAAATACTCC
ACCCATTGACGTCAATGGAAAGTCCCTATTGGCGTTACTATGGGAACATACGTCATTATTGACGTCAATGGGCGGGGGTCGTTGGGCGGTCAGCC
AGGCGGGCCATTTACCGTAAGTTATGTAACGCCTGCAGGTTAATTAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGAACAGTATTTGGTATCTGC
GCTCTGCTGAAGCCAGTTACCTTCGGAAAAAGAGTTGGTAGCTCTTGATCCGGCAAACAAACCACCGCTGGTAGCGGTGGTTTTTTTGTTTGCAA
GCAGCAGATTACGCGCAGAAAAAAAGGATCTCAAGAAGATCCTTTGATCTTTTCTACGGGGTCTGACGCTCAGTGGAACGAAAACTCACGTTAAG
GGATTTTGGTCATGGCTAGTTAATTAACATTTAAATCAGCGGCCGCAATAAAATATCTTTATTTTCATTACATCTGTGTGTTGGTTTTTTGTGTG
AATCGTAACTAACATACGCTCTCCATCAAAACAAAACGAAACAAAACAAACTAGCAAAATAGGCTGTCCCCAGTGCAAGTGCAGGTGCCAGAACA
TTTCTCTATCGAA
```

*FIG. 7*

SEQ ID NO:7
GGATCTGCGATCGCTCCGGTGCCCGTCAGTGGGCAGAGCGCACATCGCCCACAGTCCCCGAGAAGTTGGGGGGAGGGGTCGGCAATTGAACGGGT
GCCTAGAGAAGGTGGCGCGGGGTAAACTGGGAAAGTGATGTCGTGTACTGGCTCCGCCTTTTTCCCGAGGGTGGGGGAGAACCGTATATAAGTGC
AGTAGTCGCCGTGAACGTTCTTTTTCGCAACGGGTTTGCCGCCAGAACACAGCTGAAGCTTCGAGGGGCTCGCATCTCTCCTTCACGCGCCCGCC
GCCCTACCTGAGGCCGCCATCCACGCCGGTTGAGTCGCGTTCTGCCGCCTCCCGCCTGTGGTGCCTCCTGAACTGCGTCCGCCGTCTAGGTAAGT
TTAAAGCTCAGGTCGAGACCGGGCCTTTGTCCGGCGCTCCCTTGGAGCCTACCTAGACTCAGCCGGCTCTCCACGCTTTGCCTGACCCTGCTTGC
TCAACTCTACGTCTTTGTTTCGTTTTCTGTTCTGCGCCGTTACAGATCCAAGCTGTGACCGGCGCCTACCTGAGATCACCGGcGAAGGAGGGCCA
CCATGTACAGGATGCAACTCCTGTCTTGCATTGCACTAAGTCTTGCACTTGTCACGAATTCGATGGCTGAAACTGTTGAAAGTTGTTTAGCAAAA
CCCCATACAGAAAATTCATTTACTAACGTCTGGAAAGACGACAAAACTTTAGATCGTTACGCTAACTATGAGGGCTGTCTGTGGAATGCTGGAGG
CGTTGTAGTTTGTACTGGTGACGAAACTCAGTGTTACGGTCATTGGGTTCCTATTGGGCTTGCTATCCCTGAAAATGAGGGTGGTGGCTCTGAGG
GTGGCGGTTCTGAGGGTGGCGGTTCTGAGGGTGGCGGTACTAAAACCTCCTGAGTACGGTGATACACCTATTCCGGGCTATACTTATATCAACCCT
CTCGACGGCACTTATCCGCCTGGTACTGAGCAAAACCCCGCTAATCCTAATCCTTCTCTTGAGGAGTCTCAGCCTCTTAATACTTTCATGTTTCA
GAATAATAGGTTCCGAAATAGGCAGGGGGCATTAACTGTTTATACGGGCACTTTTACTCAAGGCACTGACCCCGTTAAAACTTATTACCAGTACA
CTCCTGTATCATCAAGGCCATGTATGACGCTTACTGGAACGGTAAATTCAGAGACTGCGCTTTCCATTCTGGCTTTAATGAGGATCCATTCGTT
TGTGAATATCAAGGCCAATCGTCTGACCTGCCTCAACCTCCTGCCAATGCTGGCGGCGAGTCTGGTGGTGGTTCTGGTGGCGGCTCTGAGGGTGG
TGGCTCTGAGGGTGGCGGTTCTGAGGGTGGCGGCTCTGAGGGAGGCGGTTCCGGTGGTGGCTCTGGTTCCGGTGCCAGATCTGACAAAACTCACA
CATGCCCACCGTGCCCAGCACCTGAACTCCTGGGGGGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAACTGGTACGTGGACGGCGTGGAGGTGCATAATGCCAA
GACAAAGCCGCGGGAGGAGCAGTACAACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCTTCCTCTACAGCAAGCTCACCGTGGACAAGA
GCAGGTGGCAGCAGGGGAACGTCTTCTCATGCTCCGTGATGCACGAGGCTCTGCACAACCACTACACGCAGAAGAGCCTCTCCCTGTCTCCGGGT
AAATGAGTGCTAGCTGGCCAGACATGATAAGATACATTGATGAGTTTGGACAAACCACAACTAGAATGCAGTGAAAAAAATGCTTTATTTGTGAA
ATTTGTGATGCTATTGCTTTATTTGTAACCATTATAAGCTGCAATAAACAAGTTAACAACAACAATTGCATTCATTTTATGTTTCAGGTTCAGGG
GGAGGTGTGGGAGGTTTTTTAAAGCAAGTAAAACCTCTACAAATGTGGTATGGAATTAATTCTAAAATACAGCATAGCAAAACTTTAACCTCCAA
ATCAAGCCTCTACTTGAATCCTTTTCTGAGGGATGAATAAGGCATAGGCATCAGGGGCTGTTGCCAATGTGCATTAGCTGTTTGCAGCCTCACCT
TCTTTCATGGAGTTTAAGATATAGTGTATTTTCCCAAGGTTTGAACTAGCTCTTCATTTCTTTATGTTTTAAATGCACTGACCTCCCACATTCCC
TTTTTAGTAAAATATTCAGAAATAATTTAAATACATCATTGCAATGAAAATAAATGTTTTTTATTAGGCAGAATCCAGATGCTCAAGGCCCTTCA
TAATATCCCCCAGTTTAGTAGTTGGACTTAGGGAACAAAGGAACCTTTAATAGAAATTGGACAGCAAGAAAGCGAGCTTCTAGCTTATCCTCAGT
CCTGCTCCTCTGCCACAAAGTGCACGCAGTTGCCGGCCGGGTCGCGCAGGGCGAACTCCCGCCCCCACGGCTGCTCGCCGATCTCGGTCATGGCC
GGCCCGGAGGCGTCCCGGAAGTTCGTGGACACGACCTCCGACCACTCGGCGTACAGCTCGTCCAGGCCGCGCACCCACACCCAGGCCAGGGTGTT
GTCCGGCACCACCTGGTCCTGGACCGCGCTGATGAACAGGGTCACGTCGTCCCGGACCACACCGGCGAAGTCGTCCTCCACGAAGTCCCGGGAGA
ACCCGAGCCGGTCGGTCCAGAACTCGACCGCTCCGGCGACGTCGCGCGCGGTGAGCACCGGAACGGCACTGGTCAACTTGGCCATGATGGCTCCT
CctgtcaggagaggaaagagaagaaggttagtacaattgCTATAGTGAGTTGTATTATACTATGCAGATATACTATGCCAATGATTAATTGTCAA
ACTAGGGCTGCAgggttcatagtgccacttttcctgcactgccccatctcctgcccacccttttccaggcatagacagtcagtgacttacCAAAC
TCACAGGAGGGAGAAGGCAGAAGCTTGAGACAGACCCGCGGGACCGCCGAACTGCGAGGGGACGTGGCTAGGGCGGCTTCTTTTATGGTGCGCCG
GCCCTCGGAGGCAGGGCGCTCGGGGAGGCCTAGCGGCCAATCTGCGGTGGCAGGAGGCGGGGCCGAAGGCCGTGCCTGACCAATCCGGAGCACAT
AGGAGTCTCAGCCCCCCGCCCCAAAGCAAGGGGAAGTCACGCGCCTGTAGCGCCAGCGTGTTGTGAAATGGGGGCTTGGGGGGGTTGGGGCCCTG
ACTAGTCAAAACAAACTCCCATTGACGTCAATGGGGTGGAGACTTGGAAATCCCCGTGAGTCAAACCGCTATCCACGCCCATTGATGTACTGCCA
AAACCGCATCATCATGGTAATAGCGATGACTAATACGTAGATGTACTGCCAAGTAGGAAAGTCCCATAAGGTCATGTACTGGGCATAATGCCAGG
CGGGCCATTTACCGTCATTGACGTCAATAGGGGGCGTACTTGGCATATGATACACTTGATGTACTGCCAAGTGGGCAGTTTACCGTAAATACTCC
ACCCATTGACGTCAATGGAAAGTCCCTATTGGCGTTACTATGGGAACATACGTCATTATTGACGTCAATGGGCGGGGGTCGTTGGGCGGTCAGCC
AGGCGGGCCATTTACCGTAAGTTATGTAACGCCTGCAGGTTAATTAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGAACAGTATTTGGTATCTGC
GCTCTGCTGAAGCCAGTTACCTTCGGAAAAAGAGTTGGTAGCTCTTGATCCGGCAAACAAACCACCGCTGGTAGCGGTGGTTTTTTTGTTTGCAA
GCAGCAGATTACGCGCAGAAAAAAAGGATCTCAAGAAGATCCTTTGATCTTTTCTACGGGGTCTGACGCTCAGTGGAACGAAAACTCACGTTAAG
GGATTTTGGTCATGCTAGTTAATTAACATTTAAATCAGCGGCCGCAATAAAATATCTTTATTTTCATTACATCTGTGTGTTGGTTTTTTGTGTG
AATCGTAACTAACATACGCTCTCCATCAAAACAAAACGAAACAAACAAACTAGCAAAATAGGCTGTCCCCAGTGCAAGTGCAGGTGCCAGAACA
TTTCTCTATCGAA

*FIG. 8*

SEQUENCE LISTING

```
<160> NUMBER OF SEQ ID NOS: 9

<210> SEQ ID NO 1
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Gly Ser Glu Gly Gly Gly Ser Glu Gly Gly
65                  70                  75                  80
```

```
Gly Ser Glu Gly Gly Gly Thr Lys Pro Pro Glu Tyr Gly Asp Thr Pro
                85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
            115                 120                 125

Gln Pro Leu Asn Thr Phe Met Phe Gln Asn Asn Arg Phe Arg Asn Arg
130                 135                 140

Gln Gly Ala Leu Thr Val Tyr Thr Gly Thr Phe Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Pro Phe Val Cys Glu Tyr Gln Gly Gln Ser Ser
            195                 200                 205

Asp Leu Pro Gln Pro Pro Val Asn Ala Gly Gly Ser Gly Gly Gly
210                 215                 220

Ser Gly Gly Gly Ser Glu Gly Gly Ser Glu Gly Gly Ser Glu
225                 230                 235                 240

Gly Gly Gly Ser Glu Gly Gly Ser Gly Gly Ser Gly Ser Gly
                245                 250                 255

Ala Met Val Arg Ser Asp Lys Thr His Thr Cys Pro Pro Cys Pro Ala
                260                 265                 270

Pro Glu Leu Leu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
            290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
                485
```

```
<210> SEQ ID NO 2
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2
```

Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
        115                 120                 125

Gln Pro Leu Asn Thr Phe Met Phe Gln Asn Asn Arg Phe Arg Asn Arg
130                 135                 140

Gln Gly Ala Leu Thr Val Tyr Thr Gly Thr Phe Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Pro Phe Val Cys Glu Tyr Gln Gly Gln Ser Ser
        195                 200                 205

Asp Leu Pro Gln Pro Pro Ala Asn Ala Gly Gly Glu Ser Gly Gly Gly
    210                 215                 220

Ser Gly Gly Gly Ser Glu Gly Gly Ser Glu Gly Gly Ser Glu
225                 230                 235                 240

Gly Gly Gly Ser Glu Gly Gly Ser Gly Gly Ser Gly Ser Gly
                245                 250                 255

Ala Arg Ser Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

```
Ala Pro Ile Glu Lys Thr Ile Ser Lys Ala Lys Gly Gln Pro Arg Glu
370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 3
<211> LENGTH: 1530
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atgtacagga tgcaactcct gtcttgcatt gcactaagtc ttgcacttgt cacgaattcg      60
atggctgaaa ctgttgaaag ttgtttagca aaaccccata cagaaaattc atttactaac    120
gtctggaaag acgacaaaac tttagatcgt tacgctaact atgagggctg tctgtggaat    180
gctacaggcg ttgtagtttg tactggtgac gaaactcagt gttacggtac atgggttcct    240
attgggcttg ctatccctga aaatgagggt ggtggtctg agggtggcgg ttctgagggt     300
ggcggttctg agggtggcgg tactaaacct cctgagtacg gtgatacacc tattccgggc    360
tatacttata tcaaccctct cgacggcact tatccgcctg gtactgagca aaaccccgct    420
aatcctaatc cttctcttga ggagtctcag cctcttaata ctttcatgtt tcagaataat    480
aggttccgaa ataggcaggg ggcattaact gtttatacgg gcactttta tcaaggcact    540 gaccccgtta aaacttatta ccagtacact cctgtatcat caaaagccat gtatgacgct    600
tactggaacg gtaaattcag agactgcgct ttccattctg gctttaatga ggatccattc    660
gtttgtgaat atcaaggcca atcgtctgac ctgcctcaac tcctgtcaa tgctggcggc     720 ggctctggtg gtggttctgg tggcggctct gagggtggtg ctctgagggt ggcggttct    780 gagggtggcg gctctgaggg aggcggttcc ggtggtggct ctggttccgg tgccatggtt    840
agatctgaca aaactcacac atgcccaccg tgcccagcac ctgaactcct ggggggaccg    900
tcagtcttcc tcttcccccc aaaacccaag gacaccctca tgatctcccg gacccctgag    960
gtcacatgcg tggtggtgga cgtgagccac gaagaccctg aggtcaagtt caactggtac   1020
gtggacggcg tggaggtgca taatgccaag acaaagccgc gggaggagca gtacaacagc   1080
acgtaccgtg tggtcagcgt cctcaccgtc ctgcaccagg actggctgaa tggcaaggag   1140
tacaagtgca aggtctccaa caaagccctc ccagccccca tcgagaaaac catctccaaa   1200
gccaaagggc agccccgaga accacaggtg tacaccctgc ccccatcccg ggaggagatg   1260
accaagaacc aggtcagcct gacctgcctg gtcaaaggct tctatccag cgacatcgcc    1320
```

```
gtggagtggg agagcaatgg gcagccgag  aacaactaca agaccacgcc tcccgtgctg    1380
gactccgacg gctccttctt cctctacagc aagctcaccg tggacaagag caggtggcag    1440
caggggaacg tcttctcatg ctccgtgatg cacgaggctc tgcacaacca ctacacgcag    1500
aagagcctct ccctgtctcc gggtaaatga                                    1530
```

<210> SEQ ID NO 4
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

```
atgtacagga tgcaactcct gtcttgcatt gcactaagtc ttgcacttgt cacgaattcg      60
atggctgaaa ctgttgaaag ttgtttagca aaaccccata cagaaaattc atttactaac     120
gtctggaaag acgacaaaac tttagatcgt tacgctaact atgagggctg tctgtggaat     180
gctacaggcg ttgtagtttg tactggtgac gaaactcagt gttacggtac atgggttcct     240
attgggcttg ctatccctga aaatgagggt ggtggctctg agggtggcgg ttctgagggt     300
ggcggttctg agggtggcgg tactaaacct cctgagtacg tgataccc tattccgggc      360 tatacttata tcaaccctct cgacggcact tatccgcctg gtactgagca aaaccccgct     420
aatcctaatc cttctcttga ggagtctcag cctcttaata ctttcatgtt tcagaataat     480
aggttccgaa ataggcaggg ggcattaact gtttatacgg gcacttttac tcaaggcact     540
gaccccgtta aaacttatta ccagtacact cctgtatcat caaaagccat gtatgacgct     600
tactggaacg gtaaattcag agactgcgct ttccattctg gctttaatga ggatccattc     660
gtttgtgaat atcaaggcca atcgtctgac ctgcctcaac ctcctgccaa tgctggcggc     720
gagtctggtg gtggttctgg tggcggctct gagggtggtg gctctgaggg tggcggttct     780
gagggtggcg gctctgaggg aggcggttcc ggtggtggct ctggttccgg tgccagatct     840
gacaaaactc acacatgccc accgtgccca gcacctgaac tcctgggggg accgtcagtc     900
ttcctcttcc ccccaaaacc caaggacacc ctcatgatct cccggacccc tgaggtcaca     960
tgcgtggtgg tggacgtgag ccacgaagac cctgaggtca agttcaactg gtacgtggac    1020
ggcgtggagg tgcataatgc caagacaaag ccgcgggagg agcagtacaa cagcacgtac    1080
cgtgtggtca gcgtcctcac cgtcctgcac caggactggc tgaatggcaa ggagtacaag    1140
tgcaaggtct ccaacaaagc cctcccagcc cccatcgaga aaaccatctc caaagccaaa    1200
gggcagcccc gagaaccaca ggtgtacacc ctgcccccat cccgggagga gatgaccaag    1260
aaccaggtca gcctgacctg cctggtcaaa ggcttctatc cagcgacat cgccgtggag    1320 tgggagagca atgggcagcc ggagaacaac tacaagacca cgcctcccgt gctggactcc    1380
gacggctcct tcttcctcta cagcaagctc accgtggaca gagcaggtg gcagcagggg    1440 aacgtcttct catgctccgt gatgcacgag gctctgcaca accactacac gcagaagagc    1500
ctctccctgt ctccgggtaa atga                                           1524
```

<210> SEQ ID NO 5
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Ala Glu Thr Val Glu Ser Cys Leu Ala Lys Pro His Thr Glu Asn Ser
1               5                   10                  15
Phe Thr Asn Val Trp Lys Asp Asp Lys Thr Leu Asp Arg Tyr Ala Asn
            20                  25                  30
Tyr Glu Gly Cys Leu Trp Asn Ala Gly Val Val Cys Thr Gly
        35                  40                  45
Asp Glu Thr Gln Cys Tyr Gly His Trp Val Pro Ile Gly Leu Ala Ile
50                  55                  60
Pro Glu Asn Glu Gly Gly Ser Glu Gly Gly Ser Glu Gly Gly
65                  70                  75                  80
Gly Ser Glu Gly Gly Gly Thr Lys Pro Pro Glu Tyr Gly Asp Thr Pro
                85                  90                  95
Ile Pro Gly Tyr Thr Tyr Ile Asn Pro Leu Asp Gly Thr Tyr Pro Pro
            100                 105                 110
Gly Thr Glu Gln Asn Pro Ala Asn Pro Asn Pro Ser Leu Glu Glu Ser
        115                 120                 125
Gln Pro Leu Asn Thr Phe Met Phe Gln Asn Asn Arg Phe Arg Asn Arg
130                 135                 140
Gln Gly Ala Leu Thr Val Tyr Thr Gly Thr Phe Thr Gln Gly Thr Asp
145                 150                 155                 160
Pro Val Lys Thr Tyr Tyr Gln Tyr Thr Pro Val Ser Ser Arg Ala Met
                165                 170                 175
Tyr Asp Ala Tyr Trp Asn Gly Lys Phe Arg Asp Cys Ala Phe His Ser
            180                 185                 190
Gly Phe Asn Glu Asp Pro Phe Val Cys Glu Tyr Gln Gly Gln Ser Ser
        195                 200                 205
Asp Leu Pro Gln Pro Pro Ala Asn Ala Gly Gly Glu Ser Gly Gly Gly
210                 215                 220
Ser Gly Gly Gly Ser Glu Gly Gly Ser Glu Gly Gly Ser Glu
225                 230                 235                 240
Gly Gly Gly Ser Glu Gly Gly Ser Gly Gly Ser Gly Ser Gly
                245                 250                 255
Ala Arg Ser Asp Lys Thr His Thr Cys Pro Pro Cys Pro Ala Pro Glu
            260                 265                 270
Leu Leu Gly Gly Pro Ser Val Phe Leu Phe Pro Pro Lys Pro Lys Asp
        275                 280                 285
Thr Leu Met Ile Ser Arg Thr Pro Glu Val Thr Cys Val Val Val Asp
    290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
            340                 345                 350
Leu Asn Gly Lys Glu Tyr Lys Cys Lys Val Ser Asn Lys Ala Leu Pro
        355                 360                 365
Ala Pro Ile Glu Lys Thr Ile Ser Lys Ala Lys Gly Gln Pro Arg Glu
    370                 375                 380
```

```
Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
        420                 425                 430

Thr Pro Pro Val Leu Asp Ser Asp Gly Ser Phe Phe Leu Tyr Ser Lys
    435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 6
<211> LENGTH: 4953
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc      540 ctacctgaga tcaccggcga aggagggcca ccatgtacag gatgcaactc ctgtcttgca     600
ttgcactaag tcttgcactt gtcacgaatt cgatggctga aactgttgaa agttgtttag     660
caaaacccca tacagaaaat tcatttacta acgtctggaa agacgacaaa actttagatc     720
gttacgctaa ctatgagggc tgtctgtgga atgctacagg cgttgtagtt tgtactggtg     780
acgaaactca gtgttacggt cattgggttc ctattgggct tgctatccct gaaaatgagg     840
gtggtggctc tgagggtggc ggttctgagg gtggcggttc tgagggtggc ggtactaaac     900
ctcctgagta cggtgataca cctattccgg gctatactta tatcaaccct ctcgacggca     960
cttatccgcc tggtactgag caaaaccccg ctaatcctaa tccttctctt gaggagtctc    1020
agcctcttaa tactttcatg tttcagaata ataggttccg aaataggcag gggcattaa     1080 ctgtttatac gggcactttt actcaaggca ctgaccccgt taaaacttat taccagtaca    1140
ctcctgtatc atcaagagcc atgtatgacg cttactggaa cggtaaattc agagactgcg    1200
ctttccattc tggctttaat gaggatccat tcgtttgtga atatcaaggc caatcgtctg    1260
acctgcctca acctcctgcc aatgctgcgc gcgagtctgg tggtggttct ggtggcggct    1320
ctgagggtgg tggctctgag ggtggcggtt ctgagggtgg cggctctgag ggaggcggtt    1380
```

```
ccggtggtgg ctctggttcc ggtgccagat ctgacaaaac tcacacatgc ccaccgtgcc    1440
cagcacctga actcctgggg ggaccgtcag tcttcctctt cccccaaaa cccaaggaca      1500 ccctcatgat ctcccggacc cctgaggtca catgcgtggt ggtggacgtg agccacgaag    1560
accctgaggt caagttcaac tggtacgtgg acggcgtgga ggtgcataat gccaagacaa    1620
agccgcggga ggagcagtac aacagcacgt accgtgtggt cagcgtcctc accgtcctgc    1680
accaggactg gctgaatggc aaggagtaca agtgcaaggt ctccaacaaa gccctcccag    1740
cccccatcga aaaaccatc tccaaagcca aagggcagcc ccgagaacca caggtgtaca    1800
ccctgccccc atcccgggag gagatgacca agaaccaggt cagcctgacc tgcctggtca    1860
aaggcttcta tcccagcgac atcgccgtgg agtgggagag caatgggcag ccggagaaca    1920
actacaagac cacgcctccc gtgctggact ccgacggctc cttcttcctc tacagcaagc    1980
tcaccgtgga caagagcagg tggcagcagg ggaacgtctt ctcatgctcc gtgatgcacg    2040
aggctctgca caaccactac acgcagaaga gcctctccct gtctccgggt aaatgagtgc    2100
tagctggcca gacatgataa gatacattga tgagtttgga caaaccacaa ctagaatgca    2160
gtgaaaaaaa tgctttattt gtgaaatttg tgatgctatt gctttatttg taaccattat    2220
aagctgcaat aaacaagtta acaacaacaa ttgcattcat tttatgtttc aggttcaggg    2280
ggaggtgtgg gaggtttttt aaagcaagta aaacctctac aaatgtggta tggaattaat    2340
tctaaaatac agcatagcaa aactttaacc tccaaatcaa gcctctactt gaatcctttt    2400
ctgagggatg aataaggcat aggcatcagg ggctgttgcc aatgtgcatt agctgtttgc    2460
agcctcacct tctttcatgg agtttaagat atagtgtatt ttcccaaggt ttgaactagc    2520
tcttcatttc tttatgtttt aaatgcactg acctcccaca ttccttttt agtaaaatat    2580 tcagaaataa tttaaataca tcattgcaat gaaaataaat gttttttatt aggcagaatc    2640
cagatgctca aggcccttca taatatcccc cagtttagta gttggactta gggaacaaag    2700
gaacctttaa tagaaattgg acagcaagaa agcgagcttc tagcttatcc tcagtcctgc    2760
tcctctgcca caaagtgcac gcagttgccg gccgggtcgc gcagggcgaa ctcccgcccc    2820
cacggctgct cgccgatctc ggtcatggcc ggcccggagg cgtcccggaa gttcgtggac    2880
acgacctccg accactcggc gtacagctcg tccaggccgc gcacccacac ccaggccagg    2940
gtgttgtccg gcaccacctg gtcctggacc gcgctgatga acagggtcac gtcgtcccgg    3000
accacaccgg cgaagtcgtc ctccacgaag tcccgggaga cccgagccg tcggtccag     3060 aactcgaccg ctccggcgac gtcgcgcgcg gtgagcaccg gaacggcact ggtcaacttg    3120
gccatgatgg ctcctcctgt caggagagga aagagaagaa ggttagtaca attgctatag    3180
tgagttgtat tatactatgc agatatacta tgccaatgat taattgtcaa actagggctg    3240
cagggttcat agtgccactt ttcctgcact gccccatctc ctgcccaccc tttcccaggc    3300
atagacagtc agtgacttac caaactcaca ggagggagaa ggcagaagct tgagacagac    3360
ccgcgggacc gccgaactgc gagggacgt ggctagggcg gcttcttta tggtgcgccg    3420 gccctcggag gcagggcgct cggggaggcc tagcggccaa tctgcggtgg caggaggcgg    3480
ggccgaaggc cgtgcctgac caatccggag cacataggag tctcagcccc cgcccccaaa    3540
gcaaggggaa gtcacgcgcc tgtagcgcca gcgtgttgtg aaatgggggc ttggggggt    3600 tggggccctg actagtcaaa acaaactccc attgacgtca atggggtgga gacttggaaa    3660
tccccgtgag tcaaaccgct atccacgccc attgatgtac tgccaaaacc gcatcatcat    3720
ggtaatagcg atgactaata cgtagatgta ctgccaagta ggaaagtccc ataaggtcat    3780
```

| | |
|---|---|
| gtactgggca taatgccagg cgggccattt accgtcattg acgtcaatag ggggcgtact | 3840 |
| tggcatatga tacacttgat gtactgccaa gtgggcagtt taccgtaaat actccaccca | 3900 |
| ttgacgtcaa tggaaagtcc ctattggcgt tactatggga acatacgtca ttattgacgt | 3960 |
| caatgggcgg gggtcgttgg gcggtcagcc aggcgggcca tttaccgtaa gttatgtaac | 4020 |
| gcctgcaggt taattaagaa catgtgagca aaaggccagc aaaaggccag gaaccgtaaa | 4080 |
| aaggccgcgt tgctggcgtt tttccatagg ctccgccccc ctgacgagca tcacaaaaat | 4140 |
| cgacgctcaa gtcagaggtg gcgaaacccg acaggactat aaagatacca ggcgtttccc | 4200 |
| cctggaagct ccctcgtgcg ctctcctgtt ccgaccctgc cgcttaccgg atacctgtcc | 4260 |
| gcctttctcc cttcgggaag cgtggcgctt tctcatagct cacgctgtag gtatctcagt | 4320 |
| tcggtgtagg tcgttcgctc caagctgggc tgtgtgcacg aacccccegt tcagcccgac | 4380 |
| cgctgcgcct tatccggtaa ctatcgtctt gagtccaacc cggtaagaca cgacttatcg | 4440 |
| ccactggcag cagccactgg taacaggatt agcagagcga gtatgtagg cggtgctaca | 4500 |
| gagttcttga agtggtggcc taactacggc tacactagaa gaacagtatt tggtatctgc | 4560 |
| gctctgctga agccagttac cttcggaaaa agagttggta gctcttgatc cggcaaacaa | 4620 |
| accaccgctg gtagcggtgg tttttttgtt tgcaagcagc agattacgcg cagaaaaaaa | 4680 |
| ggatctcaag aagatccttt gatcttttct acggggtctg acgctcagtg gaacgaaaac | 4740 |
| tcacgttaag ggattttggt catggctagt taattaacat ttaaatcagc ggccgcaata | 4800 |
| aaatatcttt attttcatta catctgtgtg ttggtttttt gtgtgaatcg taactaacat | 4860 |
| acgctctcca tcaaaacaaa acgaaacaaa acaaactagc aaaataggct gtccccagtg | 4920 |
| caagtgcagg tgccagaaca tttctctatc gaa | 4953 |

<210> SEQ ID NO 7
<211> LENGTH: 4953
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

| | |
|---|---|
| ggatctgcga tcgctccggt gcccgtcagt gggcagagcg cacatcgccc acagtccccg | 60 |
| agaagttggg gggagggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cgatggctga aactgttgaa agttgtttag | 660 |
| caaaacccca tacagaaaat tcatttacta acgtctggaa agacgacaaa actttagatc | 720 |
| gttacgctaa ctatgagggc tgtctgtgga atgctggagg cgttgtagtt tgtactggtg | 780 |
| acgaaactca gtgttacggt cattgggttc ctattgggct tgctatccct gaaaatgagg | 840 |

```
gtggtggctc tgagggtggc ggttctgagg gtggcggttc tgagggtggc ggtactaaac    900
ctcctgagta cggtgataca cctattccgg gctatactta tatcaaccct ctcgacggca    960
cttatccgcc tggtactgag caaaacccg ctaatcctaa tccttctctt gaggagtctc    1020
agcctcttaa tactttcatg tttcagaata ataggttccg aaataggcag ggggcattaa    1080
ctgtttatac gggcactttt actcaaggca ctgaccccgt taaaacttat taccagtaca    1140
ctcctgtatc atcaagagcc atgtatgacg cttactggaa cggtaaattc agagactgcg    1200
ctttccattc tggctttaat gaggatccat tcgtttgtga atatcaaggc caatcgtctg    1260
acctgcctca acctcctgcc aatgctggcg gcgagtctgg tggtggttct ggtggcggct    1320
ctgagggtgg tggctctgag ggtggcggtt ctgagggtgg cggctctgag ggaggcggtt    1380
ccggtggtgg ctctggttcc ggtgccagat ctgacaaaac tcacacatgc ccaccgtgcc    1440
cagcacctga actcctgggg ggaccgtcag tcttcctctt ccccccaaaa cccaaggaca    1500
ccctcatgat ctcccggacc cctgaggtca catgcgtggt ggtggacgtg agccacgaag    1560
accctgaggt caagttcaac tggtacgtgg acggcgtgga ggtgcataat gccaagacaa    1620
agccgcggga ggagcagtac aacagcacgt accgtgtggt cagcgtcctc accgtcctgc    1680
accaggactg gctgaatggc aaggagtaca agtgcaaggt ctccaacaaa gccctcccag    1740
cccccatcga gaaaaccatc tccaaagcca agggcagcc cgagaaccca caggtgtaca    1800
ccctgccccc atcccgggag gagatgacca agaaccaggt cagcctgacc tgcctggtca    1860
aaggcttcta tcccagcgac atcgccgtgg agtgggagag caatgggcag ccggagaaca    1920
actacaagac cacgcctccc gtgctggact ccgacggctc cttcttcctc tacagcaagc    1980
tcaccgtgga caagagcagg tggcagcagg ggaacgtctt ctcatgctcc gtgatgcacg    2040
aggctctgca caaccactac acgcagaaga gcctctccct gtctccgggt aaatgagtgc    2100
tagctggcca gacatgataa gatacattga tgagtttgga caaaccacaa ctagaatgca    2160
gtgaaaaaaa tgctttattt gtgaaatttg tgatgctatt gctttatttg taaccattat    2220
aagctgcaat aaacaagtta acaacaacaa ttgcattcat tttatgtttc aggttcaggg    2280
ggaggtgtgg gaggtttttt aaagcaagta aaacctctac aaatgtggta tggaattaat    2340
tctaaaatac agcatagcaa aactttaacc tccaaatcaa gcctctactt gaatcctttt    2400
ctgagggatg aataaggcat aggcatcagg ggctgttgcc aatgtgcatt agctgtttgc    2460
agcctcacct tctttcatgg agtttaagat atagtgtatt ttcccaaggt ttgaactagc    2520
tcttcatttc tttatgtttt aaatgcactg acctcccaca ttccctttt agtaaaatat    2580
tcagaaataa tttaaataca tcattgcaat gaaaataaat gtttttattt aggcagaatc    2640
cagatgctca aggcccttca taatatcccc cagtttagta gttggactta gggaacaaag    2700
gaacctttaa tagaaattgg acagcaagaa agcgagcttc tagcttatcc tcagtcctgc    2760
tcctctgcca caaagtgcac gcagttgccg gccgggtcgc gcagggcgaa ctcccgcccc    2820
cacggctgct cgccgatctc ggtcatgcc ggcccggagg cgtcccggaa gttcgtggac    2880
acgacctccg accactcggc gtacagctcg tccaggccgc gcacccacac ccaggccagg    2940
gtgttgtccg gcaccacctg gtcctggacc gcgctgatga acagggtcac gtcgtcccgg    3000
accacaccgg cgaagtcgtc ctccacgaag tcccgggaga acccgagccg tcggtccag    3060
aactcgaccg ctccggcgac gtcgcgcgcg gtgagcaccg gaacggcact ggtcaacttg    3120
gccatgatgg ctcctcctgt caggagagga aagagaagaa ggttagtaca attgctatag    3180
tgagttgtat tatactatgc agatatacta tgccaatgat taattgtcaa actagggctg    3240
```

```
caggggttcat agtgccactt ttcctgcact gccccatctc ctgcccaccc tttcccaggc    3300
atagacagtc agtgacttac caaactcaca ggagggagaa ggcagaagct tgagacagac    3360
ccgcgggacc gccgaactgc gaggggacgt ggctagggcg gcttctttta tggtgcgccg    3420
gccctcggag gcagggcgct cggggaggcc tagcggccaa tctgcggtgg caggaggcgg    3480
ggccgaaggc cgtgcctgac caatccggag cacataggag tctcagcccc ccgccccaaa    3540
gcaaggggaa gtcacgcgcc tgtagcgcca gcgtgttgtg aaatgggggc ttgggggggt    3600
tggggccctg actagtcaaa acaaactccc attgacgtca atggggtgga gacttggaaa    3660
tccccgtgag tcaaaccgct atccacgccc attgatgtac tgccaaaacc gcatcatcat    3720
ggtaatagcg atgactaata cgtagatgta ctgccaagta ggaaagtccc ataaggtcat    3780
gtactgggca taatgccagg cgggccattt accgtcattg acgtcaatag ggggcgtact    3840
tggcatatga tacacttgat gtactgccaa gtgggcagtt taccgtaaat actccaccca    3900
ttgacgtcaa tggaaagtcc ctattggcgt tactatggga acatacgtca ttattgacgt    3960
caatgggcgg gggtcgttgg gcggtcagcc aggcgggcca tttaccgtaa gttatgtaac    4020
gcctgcaggt taattaagaa catgtgagca aaaggccagc aaaaggccag gaaccgtaaa    4080
aaggccgcgt tgctggcgtt tttccatagg ctccgccccc ctgacgagca tcacaaaaat    4140
cgacgctcaa gtcagaggtg gcgaaacccg acaggactat aaagatacca ggcgtttccc    4200
cctggaagct ccctcgtgcg ctctcctgtt ccgaccctgc cgcttaccgg atacctgtcc    4260
gcctttctcc cttcgggaag cgtggcgctt tctcatagct cacgctgtag gtatctcagt    4320
tcggtgtagg tcgttcgctc caagctgggc tgtgtgcacg aaccccccgt tcagcccgac    4380
cgctgcgcct tatccggtaa ctatcgtctt gagtccaacc cggtaagaca cgacttatcg    4440
ccactggcag cagccactgg taacaggatt agcagagcga ggtatgtagg cggtgctaca    4500
gagttcttga agtggtggcc taactacggc tacactagaa gaacagtatt tggtatctgc    4560
gctctgctga agccagttac cttcggaaaa agagttggta gctcttgatc cggcaaacaa    4620
accaccgctg gtagcggtgg tttttttgtt tgcaagcagc agattacgcg cagaaaaaaa    4680
ggatctcaag aagatccttt gatcttttct acggggtctg acgctcagtg gaacgaaaac    4740
tcacgttaag ggattttggt catggctagt taattaacat ttaaatcagc ggccgcaata    4800
aaatatcttt attttcatta catctgtgtg ttggttttt gtgtgaatcg taactaacat    4860
acgctctcca tcaaaacaaa acgaaacaaa acaaactagc aaaataggct gtccccagtg    4920
caagtgcagg tgccagaaca tttctctatc gaa    4953
```

<210> SEQ ID NO 8
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 8
gctgtctgtg gaatgctgga ggcgttgtag tttg                                34

<210> SEQ ID NO 9
<211> LENGTH: 34
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 9
caaactacaa cgcctccagc attccacaga cagc                                 34
```

POLYPEPTIDES COMPRISING A MODIFIED BACTERIOPHAGE G3P AMINO ACID SEQUENCE LACKING A GLYCOSYLATION SIGNAL

This application is a U.S. national stage entry under 35 USC § 371 of International Application No. PCT/US2015/063476, filed Dec. 2, 2015, which claims the benefit of U.S. Provisional Patent Application No. 62/087,052, filed Dec. 3, 2014, all of which are hereby incorporated by reference in their entirety to provide continuity of disclosure.

The instant application contains a Sequence Listing which has been submitted electronically in ASCII format and is hereby incorporated by reference in its entirety. Said ASCII copy, created on Nov. 24, 2015, is named 12236.0007-00304_SL.txt and is 31,489 bytes in size.

The invention relates to polypeptides that comprise a portion of filamentous bacteriophage gene 3 protein (g3p) sufficient to bind to and/or disaggregate amyloid, i.e., the N1-N2 portion of g3p and mutants and fragments thereof, wherein that g3p amino acid sequence has been modified through amino acid deletion, insertion or substitution to remove a putative glycosylation signal. The invention further relates to such polypeptides that are also modified through additional amino acid substitution to be substantially less immunogenic than the corresponding wild-type g3p amino acid sequence when used in vivo. The polypeptides of the invention retain their ability to bind and/or disaggregate amyloid. The invention further relates to the use of these g3p-modified polypeptides in the treatment and/or prevention of diseases associated with misfolding or aggregation of amyloid.

Filamentous bacteriophage g3p protein, and in particular the polypeptide portion thereof comprising the N1-N2 region of g3p, has been demonstrated to bind to and disaggregate various amyloids, such as β-amyloid, tau protein, and prion proteins. See co-pending PCT application PCT/US2012/066793, and U.S. provisional applications 61/801,349, and 61/801,849, the disclosure of each of which is incorporated herein by reference. See also, R. Krishnan et al., *J. Mol. Biol.* (2014). Despite that efficacy, it is expected that production of such polypeptides in recombinant mammalian cell systems could be deleteriously affected by glycosylation at a putative asparagine-linked glycosylation signal in the g3p sequence. In addition, systemic administration of polypeptides comprising g3p or the N1-N2 region thereof to humans could cause a deleterious immune response. None of these prior art teachings identify any potential problems relating to putative glycosylation.

The efficacy of many recombinant or otherwise non-native therapeutic proteins or polypeptides may be limited by unwanted immune reactions of patients to the therapeutic protein or polypeptide. A principal factor in the induction of an immune response by a protein is the presence of T-cell epitopes within the protein, i.e., amino acid sequences that can stimulate the activity of T-cells via presentation on major histocompatibility complex (MHC) class II molecules. T-cell epitopes are commonly defined as any amino acid sequences with the ability to bind to MHC class II molecules. When bound to MHC molecules, T-cell epitopes can be recognized by a T-cell receptor (TCR), and can cause the activation of T-cells by engaging, a T-cell receptor to promote a T-cell response. It is, however, generally understood that certain T-cell epitopes which bind to MI-IC class II molecules do not stimulate T-cell response, because these peptides are recognized as "self" within the organism to which the protein is administered.

Some T-cell epitopes may be released as peptides during the degradation of the therapeutic protein or polypeptide within cells and then presented by molecules of the MHC to trigger the activation of T-cells. For peptides presented by MHC class II molecules, such activation of T-cells can then give rise, for example, to an antibody response by direct stimulation of B-cells to produce such antibodies.

MHC class II molecules are a group of highly polymorphic proteins which play a central role in helper T-cell selection and activation. The human leukocyte antigen group DR (HLA-DR) are the predominant isotype of this group of proteins. However, isotypes HLA-DQ and HA-DP perform similar functions. In humans approximately 70 different allotypes of the DR isotype are known, for DQ there are 30 different allotypes and for DP 47 different allotypes are known. Each individual bears two to four DR alleles, two DQ and two DP alleles.

The immune response to a protein or polypeptide in an individual is heavily influenced by T-cell epitope recognition which is a function of the peptide binding specificity of that individual's HLA-DR allotype. In order to identity T-cell epitopes within a protein or polypeptide in the context of a Global population, it is desirable to consider the binding properties of as diverse a set of HLA-DR allotypes as possible, thus covering as high a percentage of the world population as possible.

T-cell epitope identification is the first step to epitope elimination. Methods enabling the detection of T-cell epitopes are known in the art and are disclosed in WO 98/52976, WO 00/34317, US2007/0269435; U.S. Pat. No. 7,208,147, Kern et al., *Nature Medicine* 4:975-978 (1998); and Kwok et al, *Trends in Immunology* 22:583-588 (2001). In these approaches, predicted or identified T-cell epitopes are removed by the use of judicious amino acid substitutions within the primary sequence of the therapeutic protein or polypeptide. Although these references enable putative identification of T-cell epitopes, the selection of amino acid substitutions that avoid negative impact on biological activity cannot be reasonably predicted. That can only be determined by testing each of the modified polypeptides for such activity.

Thus, it would be desirable to examine and reduce the glycosylation, either alone or together with reducing the immunogenicity of the N1-N2 portion of g3p without destroying its amyloid-binding/disaggregation properties. This would allow the polypeptide comprising the N1-N2 portion of g3p to be made in mammalian cells without the manufacturing difficulties associated with glycosylation. In addition, reduced immunogenicity will allow a polypeptide comprising that N1-N2 portion to be chronically administered systemically for therapeutic and/or diagnostic purposes. The present invention meets this need, by identifying the putative glycosylation signal in the N1-N2 portion of g3p and providing modifications thereof that prevent glycosylation while preserving activity of g3p polypeptides, as described in PCT/US13/62862 (WO 2014/055515) or of g3p polypeptides that have been modified to reduce or eliminate immunogenicity as described in PCT/US2014/039760, both of which are incorporated herein by reference. Thus, certain g3p polypeptides of the invention are not only modified to prevent glycosylation, but also comprise specific amino acids substitutions within these potential T-cell epitopes to produce a variant N1-N2 sequence that will reduce or eliminate the immunogenicity of that T-cell epitope without destroying the ability of the variant N1-N2 to bind to amyloid, prevent amyloid aggregation, and/or effect disaggregation of an amyloid plaques.

In certain embodiments of the invention, the polypeptides comprise g3p or an amyloid binding fragment thereof that has been modified to remove a glycosylation signal. In one embodiment, the invention also provides polypeptides comprising a variant of an N1-N2 amino acid sequence, or a mutant or fragment thereof, having reduced immunogenicity due to one or more amino acid substitutions within one or more of the identified T-cell epitopes and lacking a glycosylation signal. In one aspect, the invention provides fusion proteins comprising the variant N1-N2 sequence fused to a human immunoglobulin Fc region.

In another embodiment, the invention provides pharmaceutical compositions comprising the polypeptides of the invention and methods of treating or preventing diseases associated with misfolded and/or aggregated amyloid proteins by administering such pharmaceutical compositions to a subject suffering from or susceptible to such disease.

In a further embodiment, the invention provides nucleic acid molecules which code for the polypeptides of the invention, as well as vectors comprising those nucleic acid molecules and cells harboring such vectors.

In another embodiment, the invention provides methods for producing, the polypeptides of the invention. In particular, such methods employ the nucleic acid molecules and/or cells harboring a vector that comprises such nucleic acid molecules.

BRIEF DESCRIPTION OF THE FIGURES

FIG. 1 presents the amino acid sequence of an N1-N2-hIgG1-Fc fusion protein (SEQ ID NO:1) with five T-cell epitopes identified by bold and underline and the putative glycosylation signal italicized, bolded and underlined. Amino acids 1-217 constitute the N1-N12 portion of the wild-type g3p sequence. Amino acids 218-256 represent a linker region consisting of the wild-type g3p glycine-rich N2-C-terminal linker present in M13 bacteriophage. This region is identified by shading. Amino acids 257-261 represent amino acids encoded by the multiple cloning site used to construct a nucleic acid molecule encoding the fusion protein. The IgG-Fc portion of the protein begins at amino acid 262.

FIG. 2 presents the amino acid sequence of another g3p-hIgG1-Fc fusion protein (SEQ ID NO:2) with three T-cell epitopes identified by bold and underline and the putative glycosylation signal italicized, bolded and underlined. The fourth T-cell epitope has been eliminated by substitution of V215A and G220E as compared to SEQ ID NO:1 and the fifth T-cell epitope has been eliminated by deletion of amino acids corresponding to amino acids 258 and 259 of SEQ ID NO:1.

FIG. 3 presents a DNA sequence (SEQ ID NO:3) encoding the g3p-hIgG1-Fc fusion protein of SEQ ID NO:1 with a N-terminal mammalian signal sequence.

FIG. 4 presents a DNA sequence (SEQ ID NO:4) encoding the g3p-hIgG1-Fc fusion protein of SEQ ID NO:2 with a N-terminal mammalian signal sequence.

FIG. 5 provides a comparison of the frequency of donor allotypes expressed in the study described in Example 1.

FIG. 6 presents the amino acid sequence (SEQ ID NO:5) of a polypeptide of the invention that is a g3p-hIgG1-Fc fusion protein with amino acid changes in the putative glycosylation signal (T41G), epitope 1 (T561H), and epitope 3 (K174R), as compared to SEQ ID NO:2. The substituted amino acids are bolded, italicized, underlined and by gray highlighting.

FIG. 7 presents a DNA sequence (SEQ ID NO:6) of a plasmid encoding Polypeptide 86 with a N-terminal mammalian signal sequence. The coding sequence, including the signal sequence is indicated by bolding. The codon changes as compared to the DNA encoding SEQ ID NO:1 are indicated by underlining.

FIG. 8 presents a DNA sequence (SEQ ID NO:7) of a plasmid encoding Polypeptide 86 T41G with a N-terminal mammalian signal sequence. The coding sequence, including the signal sequence is indicated by bolding. The codon changes as compared to the DNA encoding SEQ ID NO:1 are indicated by underlining.

FIG. 9 depicts a SDS-PAGE analysis comparing, the polypeptide of SEQ ID NO:1 with Polypeptide 86 and Polypeptide 86 T41G.

FIG. 10 depicts the results a filter retardation assay comparing the polypeptide of SEQ ID NO:1 with Polypeptide 86 and Polypeptide 86 T41G.

FIG. 11 depicts comparative binding of a polypeptide of SEQ ID NO:1 with Polypeptide 86 T41G for three different types of fibers as measured by ELISA.

DETAILED DESCRIPTION OF THE INVENTION

In the present application the term "variant" (and its cognates) with respect to a reference (unmodified) amino acid or nucleic acid sequence refers to a sequence that contains one or more amino acids substitutions, deletions or insertions, or corresponding, substitution, deletion or insertion of codons. The reference sequence is also referred to as a "starting amino acid sequence" or "starting sequence." A variant does not necessarily require physical manipulation of the reference sequence. As long as a sequence contains a different amino acid as compared to a reference sequence it will be considered a "variant" regardless of how it was synthesized.

As used herein, the term "mutant" (and its cognates) refers to a starting sequence that has been modified as compared to a specific sequence set forth in the application (e.g., SEQ ID NO:1, SEQ ID NO:2, etc).

As used herein, the term "modified" (and its cognates) refers to change in a reference amino acid sequence or nucleic acid sequence. When a starting sequence is modified the resulting sequence is a variant. A modification includes one or more amino acids substitutions, deletions or insertions, or corresponding substitution, deletion or insertion of codons.

The term "corresponding substitution" as used herein means a substitution in a mutant or fragment of amino acids 1-217 of SEQ ID NO:1 that corresponds to the equivalent amino acid substitution in Table 1, Table 2, Table 6 or Table 7 when such mutant or fragment is aligned with amino acids 1-217 of SEQ ID NO:1.

An example of a fragment of amino acids 1-217 of SEQ ID NO:1 that binds to and/or disaggregates amyloid includes, but is not limited to, any fragment that comprises amino acids 1-67 of SEQ ID NO:1. Example of mutants of amino acids 1-217 of SEQ ID NO:1 that bind to and/or disaggregate amyloid include, but are not limited to: (1) amino acids 1-217 of SEQ ID NO:2; (2) amino acids 1-217 of SEQ ID NO:1, amino acids 1-217 of SEQ ID NO:2, or amino acids 1-217 of SEQ ID NO:5 bearing substitution of VVV at amino acids 43-45 with AAA; (3) amino acids 1-217 of SEQ ID NO:1, amino acids 1-217 of SEQ ID NO:2, or amino acids 1-217 of SEQ ID NO:5 having the substitution C53W; (4) amino acids 1-217 of SEQ ID NO:1, amino acids

Figure 5:
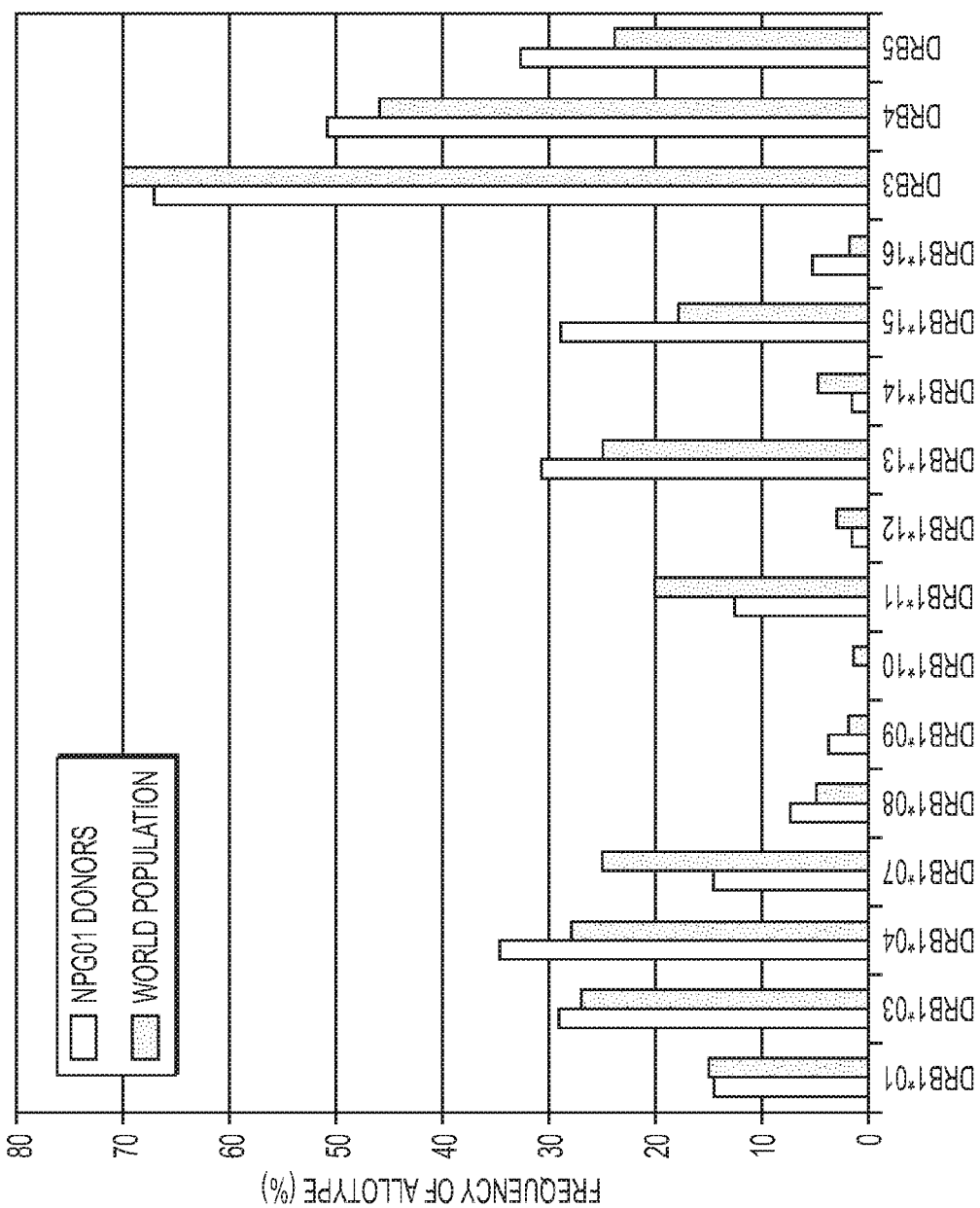

1-217 of SEQ ID NO:2, or amino acids 1-217 of SEQ ID NO:5 having a deletion of amino acids 96-103; (5) amino acids 1-217 of SEQ ID NO:1, amino acids 1-217 of SEQ ID NO:2, or amino acids 1-217 of SEQ ID NO:5 bearing the substitution of QPP at amino acids 212-214 with AGA; (6) amino acids 1-217 of SEQ ID NO:1, amino acids 1-217 of SEQ ID NO:2, or amino acids 1-217 of SEQ NO:5 having the substitutions W181A, F190A and F194A; (7) other active mutants and fragments disclosed in PCT/US2012/066793; (8) amino acids 1-217 of SEQ ID NO:5; (9) amino acids 2-217 of SEQ ID NO:1, amino acids 2-217 of SEQ ID NO:2, or amino acids 2-217 of SEQ ID NO:5; (10) amino acids 3-217 of SEQ ID NO:1, amino acids 3-217 of SEQ NO:2, or amino acids 3-217 of SEQ ID NO:5; (11) any one of amino acids 1-217 of SEQ ID NO:1, amino acids 1-217 of SEQ ID NO:2, or amino acids 1-217 of SEQ ID NO:5 containing an additional N-terminal methionine residue.

The N1-N2 portion of filamentous bacteriophage g3p protein has previously been shown to possess amyloid binding and disaggregation properties (see PCT/US2012/066793). The N1-N2 portion of native M13 phage is represented by amino acids 1-217 of SEQ ID NO:1. The same N1-N2 amino acid sequence is also present in fd and fl filamentous bacteriophage. It should be understood that amino acids 218-256 of SEQ ID NO:1 are also part of the native g3p sequence and are typically referred to as the glycine-rich linker connecting the N2 region of g3p to the C-terminal domain of g3p (CT), also known as the N3 domain. Amino acids 257-261 of SEQ ID NO:1 represent amino acids encoded by the multiple cloning site used to construct a nucleic acid molecule encoding the fusion protein of SEQ ID NO:1.

Polypeptides

Thus, in one embodiment, the invention provides a polypeptide comprising a variant of a starting amino acid sequence, wherein the starting amino acid sequence is selected from: amino acids 1-217 of SEQ ID NO:1 or amino acids 1-217 of SEQ ID NO:2 and mutants of any of the foregoing having one or more of the following modifications: substitution of VVV at amino acids 43-45 with AAA; substitution C53W; deletion of amino acids 96-103; substitution of QPP at amino acids 212-214 with AGA; substitutions W181A, F190A and F194A; deletion of amino acid 1; deletion of amino acids 1 and 2; and addition of a N-terminal methionine residue, wherein:

(a) the starting amino acid sequence is modified to remove the putative glycosylation signal at amino acids 39-41; and
(b) the polypeptide binds to and/or disaggregates amyloid.

In one aspect of this embodiment, the starting amino acid sequence is selected from: amino acids 1-217 of SEQ ID NO:1, and amino acids 1-217 of SEQ ID NO:2.

Elimination of the putative glycosylation signal is achieved by amino acid substitution of one or more of N39, A40 and/or T41; deletion of one or more of N39, A40 and/or T41; insertion of one or more amino acids between N39 and A40; and insertion of one or more amino acids between A40 and T41 insofar as such substitution, deletion or insertion does not regenerate a glycosylation signal. The putative glycosylation sequence is Asn-X-Thr/Ser, wherein X is any amino acid other than Pro or Cys. Thus, only certain substitutions for A40 will eliminate the glycosylation sequence. In one aspect of these embodiments elimination of the putative glycosylation signal is achieved by amino acid substitution of one or more of N39, A40 and/or T41. In a more specific aspect of these embodiments elimination of the putative glycosylation signal is achieved by amino acid substitution of T41. In an even more specific aspect of these embodiments elimination of the putative glycosylation signal is achieved by any of the following substitutions: T41G, T41W, T41H, T41V, T41I, T41L, T41R, T41K, T41Y, T41F, T41D, T41E, T41Q, T41N, or T41A. In the most specific aspect of these embodiments, elimination of the putative glycosylation signal is achieved by a T41G substitution.

In another embodiment of the invention the polypeptide that has been modified to remove the putative glycosylation signal at amino acids 39-41 additionally has reduced immunogenicity as compared to a corresponding polypeptide comprising the starting amino acid sequence; and the variant has from 1 to 9 amino acid substitutions (in addition to any substitutions that have eliminated the glycosylation signal) as compared to the starting amino acid sequence, wherein each amino acid substitution is selected from the group of amino acid substitutions set forth in Table 1 and Table 2. The term "corresponding polypeptide comprising the starting amino acid sequence" as used herein means a polypeptide which, except for the modification of the glycosylation signal and the additional substitution(s), has the same amino acid sequence as the polypeptide comprising the starting amino acid sequence.

TABLE 1

Deimmunizing Amino Acid Substitutions to Amino Acids 1-217 of SEQ ID NO: 1 or SEQ ID NO: 3.

| Epitope | Amino Acid # | Amino Acid present at the indicated Amino Acid # of SEQ ID NO: 1* | Substitution |
|---|---|---|---|
| 1 | 48 | G | H, K, R, S, T |
| 1 | 51 | T | G, H, K, R, P, Q, N |
| 1 | 54 | Y | G, H, K, R, P |
| 1 | 56 | T | G, H, K, R, P |
| 2 | 135 | M | A, D, G, K, N, T, H, R |
| 2 | 140 | R | D, E, H, Q, A, G |
| 2 | 141 | F | D, E |
| 2 | 143 | N | A, G |
| 3 | 173 | S | G, P, K |
| 3 | 174 | K | R |
| 3 | 176 | M | G, H, K, N, R |
| 3 | 178 | D | G, N, Q, S, T |
| 3 | 181 | W | G, H, K, R |

TABLE 2

Alternate or Additional De-Immunizing Amino Acid Substitutions to Amino Acids 1-217 of SEQ ID NO: 1, or SEQ ID NO: 3.

| Epitope | Amino Acid # | Amino Acid present at the indicated Amino Acid # of SEQ ID NO: 1* | Substitution |
|---|---|---|---|
| 1 | 48 | G | D, P |
| 1 | 50 | E | G, H, K, P, R |
| 1 | 51 | T | W |
| 1 | 53 | C | F, H, K, N, Q, R, W, Y |
| 2 | 135 | M | C, E, P, Q, S |
| 2 | 137 | Q | D, E |
| 2 | 138 | N | D, E, G, H, P, Q, S, T |
| 2 | 140 | R | M, N, P, S, Y |
| 2 | 141 | F | G, N, P, Q, Y |
| 3 | 173 | S | D, H, R, T |
| 3 | 175 | A | G, H, K, P, R |
| 3 | 176 | M | P, Q, W |
| 3 | 178 | D | F, H, K, R, W, Y |
| 3 | 179 | A | H, K, P, R |
| 3 | 181 | W | P |

*In Tables 1 and 2, each of the indicated amino acids is the same in SEQ ID NOS: 1 and 3.

The amino acid substitutions set forth in Tables 1 and 2 were derived by identifying the T-cell epitopes present completely within the N1-N2 amino acid sequence. This was done by incubating different overlapping peptide portions of the N1-N2 sequence against the peripheral blood mononuclear cells (PBMC) from a cohort of community blood donors best representing the world population of HLA-DR allotypes to identify the potential T-cell epitopes. This information was then subjected to software analysis against a database of known T-cell epitopes to identify optimal amino acid substitutions within those potential epitopes. These procedures are described in detail in the Examples.

In one aspect of these embodiments, the 1-9 additional amino acid substitutions (in addition to any substitutions that have eliminated the glycosylation signal) are selected from those set forth in Table 1. In a more specific aspect of the embodiment set forth above, the polypeptide comprises a variant of amino acids 1-217 SEQ ID NO:1 or a variant of amino acids 1-217 of SEQ ID NO:2 having only a specific single amino acid substitution, wherein the substitution is selected from one of the substitutions set forth in Table 3:

TABLE 3

Specific De-Immunizing Single Amino Acid Substitutions in Amino Acids 1-217 of SEQ ID NO: 1, or Amino Acids 1-217 of SEQ ID NO: 2

| | | | |
|---|---|---|---|
| G48H | G48K | G48R | G48S |
| G48T | T51G | T51H | T51K |
| T51P | T51R | T51Q | T51N |
| Y54G | Y54H | Y54K | Y54P |
| Y54R | T56G | T56H | T56K |
| T56P | T56R | M135A | M135D |
| M135G | M135H | M135K | M135N |
| M135R | M135T | R140A | R140D |
| R140E | R140G | R140H | R140Q |
| F141D | F141E | N143A | N143G |
| S173G | S173P | M176G | M176H |
| M176K | M176N | D178G | D178N |
| D178Q | D178S | W181G | W181H |
| W181K | W181R | S173K | K174R |
| M176R | D178T | | |

In an even more specific aspect of these embodiments, the specific single amino acid substitution is not in epitope 2. (amino acids 135-143 of SEQ ID NO:1).

In some embodiments, the polypeptide comprises a variant of amino acids 1-217 SEQ ID NO:1 or a variant of amino acids 1-217 of SEQ ID NO:2 having 2-9 amino acid substitutions (in addition to any substitutions that have eliminated the glycosylation signal), wherein the substitutions are in at least two of epitopes 1, 2 and 3, and wherein the substitutions are selected from those set forth in Tables 1 and 2. In a more specific aspect, at least two substitutions in the variant of amino acids 1-217 SEQ ID NO:1 or the variant of amino acids 1-217 of SEQ ID NO:2 are selected from those set forth in Table 1. In an even more specific aspect the polypeptide comprises a variant of SEQ ID NO:1 or SEQ ID NO:2 that has only two amino acid substitutions, wherein the substitutions are selected from any of the specific two amino acid substitutions set forth in Table 4:

TABLE 4

Specific De-Immunizing Two Amino Acid Substitutions in Amino Acids 1-217 of SEQ ID NO: 1, or Amino Acids 1-217 of SEQ ID NO: 2:

| | | | |
|---|---|---|---|
| Y54K and M135K | Y54K and M135T | Y54K and R140Q | Y54R and M135K |

TABLE 4-continued

Specific De-Immunizing Two Amino Acid Substitutions in Amino Acids 1-217 of SEQ ID NO: 1, or Amino Acids 1-217 of SEQ ID NO: 2:

| | | | |
|---|---|---|---|
| Y54R and M135T | Y54R and R140Q | T56H and M135K | T56H and M135T |
| T56H and R140Q | T56K and M135K | T56K and M135T | T56K and R140Q |
| Y54K and D178N | Y54K and W181H | Y54K and W181R | Y54K and K174R |
| Y54R and D178N | Y54R and W181H | Y54R and W181R | Y54R and K174R |
| T56H and D178N | T56H and W181H | T56H and W181R | T56H and K174R |
| T56K and D178N | T56K and W181H | T56K and W181R | T56K and K174R |
| M135K and D178N | M135K and W181H | M135K and W181R | M135K and K174R |
| M135T and D178N | M135T and W181H | M135T and W181R | M135T and K174R |
| R140Q and D178N | R140Q and W181H | R140Q and W181R | R140Q and K174R |

In a more specific aspect of these embodiments, neither of the two amino acid substitutions are in epitope 2 (amino acids 135-143 of SEQ ID NO:1). In an even more specific aspect of these embodiments, the two amino acid substitutions are T56H and K174R.

In another embodiment, the polypeptide comprises a variant of amino acids 1-217 SEQ ID NO:1 or a variant of amino acids 1-217 of SEQ ID NO:2, having 3-9 amino acid substitutions (in addition to any substitutions that have eliminated the glycosylation signal), wherein at least one amino acid substitution is in each of epitopes 1, 2 and 3, and wherein the substitutions are selected from substitutions set forth in Table 1 and Table 2. In a more specific aspect, at least three amino acids substitution in the variant of amino acids 1-217 SEQ ID NO:1 or the variant of amino acids 1-217 of SEQ ID NO:2 are selected from substitutions set forth in Table 2. In an even more specific aspect, the polypeptide comprising the variant of amino acids 1-217 SEQ ID NO:1 or the variant of amino acids 1-217 of SEQ ID NO:2 has only three amino acid substitutions, wherein the substitutions are selected from any of the specific three amino acid substitutions set forth in Table 5.

TABLE 5

Specific De-Immunizing Three Amino Acid Substitutions in Amino Acids 1-215 of SEQ ID NO: 1, Amino Acids 1-217 of SEQ ID NO: 2:

| | | | |
|---|---|---|---|
| Y54K, M135K and D178N | Y54K, M135T and D178N | Y54K, R140Q and D178N | Y54R, M135K and D178N |
| Y54R, M135T and D178N | Y54R, R140Q and D178N | T56H, M135K and D178N | T56H, M135T and D178N |
| T56H, R140Q and D178N | T56K, M135K and D178N | T56K, M135T and D178N | T56K, R140Q and D178N |
| Y54K, M135K and W181H | Y54K, M135T and W181H | Y54K, R140Q and W181H | Y54R, M135K and W181H |
| Y54R, M135T and W181H | Y54R, R140Q and W181H | T56H, M135K and W181H | T56H, M135T and W181H |
| T56H, R140Q and W181H | T56K, M135K and W181H | T56K, M135T and W181H | T56K, R140Q and W181H |
| Y54K, M135K and W181R | Y54K, M135T and W181R | Y54K, R140Q and W181R | Y54R, M135K and W181R |
| Y54R, M135T and W181R | Y54R, R140Q and W181R | T56H, M135K and W181R | T56H, M135T and W181R |
| T56H, R140Q and W181R | T56K, M135K and W181R | T56K, M135T and W181R | T56K, R140Q and W181R |
| Y54K, M135K and K174R | Y54K, M135T and K174R | Y54K, R140Q and K174R | Y54R, M135K and K174R |

TABLE 5-continued

Specific De-Immunizing Three Amino Acid Substitutions
in Amino Acids 1-215 of SEQ ID NO: 1, Amino
Acids 1-217 of SEQ ID NO: 2:

| Y54R, M135T and K174R | Y54R, R140Q and K174R | T56H, M135K and K174R | T56H, M135T and K174R |
| T56H, R140Q and K174R | T56K, M135K and K174R | T56K, M135T and K174R | T56K, R140Q and K174R |

In another embodiment, the invention provides a polypeptide comprising a g3p variant wherein one of the 1 to 9 substitution is a substitution in epitope 4 selected from V215A, V215S, V215G or V215T, V215C, V215D, V215E, V215F, V215H, V215K, V215N, V215P, V215Q, or V215R. In still another embodiment, the invention provides a polypeptide comprising a variant of amino acids 1-217 of SEQ ID NO:1, wherein one of the 1 to 9 substitutions is a substitution in epitope 4 selected from V215A, V215S, V215G, V215T, V215C, V215D, V215E, V215F, V215H, V215K, V215N, V215P, V215Q, or V215R. Through testing, of overlapping, potential T-cell epitope peptide portions of the N1-N2 sequence, applicants have determined that V215 in SEQ ID NO:1 is part of a potential T-cell epitope (epitope 4 in FIG. 1) spanning amino acids 215-223 of SEQ ID (the end of N2 through a portion of the glycine-rich linker). In a more specific aspect of this embodiments, epitope 4 has a V215A and G220E substitution (as in SEQ ID NO:2). In addition, a single V215G substitution in epitope 4 as compared to SEQ ID NO:1 did not affect the ability of the polypeptide to bind to or disaggregate amyloid. Each of the other substitutions for V215 set forth above are similarly predicted by software and database analysis to eliminate the T-cell epitope, while having little or no effect on amyloid binding.

In a more specific aspect, the polypeptide comprising a variant of amino acids 1-217 SEQ ID NO:1 has a modification that removes the putative glycosylation site at amino acids 39-41; any one of the V215 substitutions set forth above; as well as 1-8 of the amino acid substitutions set forth in Table 1 or Table 2. In an even more specific embodiment, the 1-8 amino acid substitutions are selected from those set forth in Table 1. In an even more specific aspect, the polypeptide has a T41 substitution selected from T41G, T41W, T41H, T41V, T41I, T41L, T41R, T41K, T41Y, T41F, T41D, T41E, T41Q, T41N, and T41A; a V215 substitution selected from V215A, V215S, V215G or V215T, V215C, V215D, V215E, V215F, V215H, V215K, V215N, V215P, V215Q, and V215R; and one additional single amino acid substitution selected from those set forth in Table 3, wherein the single amino acid substitution is not in epitope 2. In a more specific aspect, the polypeptide comprising a variant of amino acids 1-217 SEQ ID NO:1 has a modification that removes the putative glycosylation site at amino acids 39-41; any one of the V215 substitutions set forth above; and 2-8 additional amino acid substitutions, wherein the additional substitutions are in at least two of epitopes 1, 2 and 3, and wherein the substitutions are selected from those set forth in Table 1 or Table 2. In an even more specific embodiment, the at least one substitution in at least two of epitopes 1, 2 and 3, is selected from the substitutions set forth in Table 1. In a still more specific embodiment, the polypeptide has a T41 substitution selected from T41G, T41W, T41H, T41V, T41I, T41L, T41R, T41K, T41Y, T41F, T41D, T41E, T41Q, T41N, and T41A; V215 substitution selected from V215A, V215S, V215G or V215T, V215C, V215D, V215E, V215F, V215H, V215K, V215N, V215P, V215Q, and V215R; and one of the specific two amino acid substitutions set forth in Table 4, wherein the neither of the amino acid substitutions are in epitope 2.

In a more specific aspect, the polypeptide comprising a variant of amino acids 1-217 of SEQ ID NO:1 has a modification that removes the putative glycosylation site at amino acids 39-41; any one the V215 substitutions set forth above; and 3-8 additional amino acid substitutions selected from those set forth in Table 1 or Table 2, wherein each of epitopes 1, 2 and 3, comprise one of the additional substitutions. In an even more specific embodiment, the substitution in each of epitopes 1, 2 and 3, is selected from those set forth in Table 1. In a still more specific embodiment, the polypeptide has a 141 substitution selected from T41G, T41W, T41H, T41V, T41I, T41L, T41R, T41K, T41Y, T41F, T41D, T41E, T41Q, T41N, and T41 A; a V215 substitution selected from V215A, V215S, V215G or V215T, V215C, V215D, V215E, V215F, V215H, V215K, V215N, V215P, V215Q, and V215R; an optional G220E substitution; and one of the specific three amino acid substitutions set forth in Table 5.

In an even more specific embodiment, the polypeptide comprises a variant of amino acids 1-217 of SEQ ID NO:2 having a T41 substitution selected from T41G, T41W, T41H, T41V, T41I, T41L, T41R, T41K, T41Y, T41F, T41D, T41E, T41Q, T41N, and T41A; and a pair of substitutions selected from those set forth in Table 4, wherein one of the substitutions is in epitope 1 and the other is in epitope 3. In one aspect of this embodiment, the T41 substitution is T4G. In an alternate aspect of this embodiment, the pair of substitutions, wherein one of the substitutions is in epitope 1 and the other is in epitope 3 is T56H and K174R. In an even more specific aspect of this embodiment, the polypeptide comprises amino acids 1-215 SEQ ID NO:5. In another embodiment, the polypeptide of the invention is a fusion protein consisting essentially of a human or humanized immunoglobulin Fc polypeptide sequence fused via a peptide linker or directly to the C-terminus of the variant g3p amino acid sequence. The term "peptide linker" as used herein refers to a series of consecutive amino acids that will not interfere with the function of the polypeptide. As set forth above, in SEQ ID NOs: 1 and 3, amino acids 218-256 represent the glycine-rich linker that is normally present in the M13 g3p protein. That linker may be used or a different linker may be substituted therefor in the polypeptides of the invention. Alternatively, the Fc polypeptide sequence may be linked directly to the last amino acid encoding N2 (e.g., amino acid 217 of SEQ ID NOs 1 and 3). The choice of linker sequence and/or its absence may be made by those of skill in the art taking into account vectors available for the recombinant expression of the polypeptide of the invention, and any secondary or tertiary structure such a linker may impart to the polypeptide. In one aspect of this embodiment, the Fc polypeptide is the Fc portion of a human IgG. In a more specific aspect the polypeptide, is a variant of SEQ ID NO: 1 or SEQ ID NO:3 having a modification that removes the putative glycosylation site at amino acids 39-41. In an even more specific aspect, the polypeptide is a variant of SEQ ID NO:1 or SEQ ID NO:2 having a modification that removes the putative glycosylation site at amino acids 39-41; and 1 to 9 additional amino acid residue substitutions therein selected from the group of amino acid substitutions set forth in Table 1, Table 2, or Table 6, or Table 7, below:

TABLE 6

Deimmunizing Amino Acid Substitutions
to Amino Acids 215-223 of SEQ ID NO: 1.

| Epitope | Amino Acid # | Amino Acid present in Amino Acids 1-215 of SEQ ID NO: 1 | Substitution |
|---|---|---|---|
| 4 | 215 | V* | A*, S, G, T |
| 4 | 218 | G | C, E, N, P, Q, S, T |
| 4 | 220 | G* | E*, D, F, W |
| 4 | 221 | S | D, E, G |
| 4 | 223 | G | D, P |

TABLE 7

Alternate and Additional Deimmunizing Amino Acid Substitutions
to Amino Acids 215-223 of SEQ ID NO: 1.

| Epitope | Amino Acid # | Amino Acid present in Amino Acids 1-215 of SEQ ID NOs 1-3 | Substitution |
|---|---|---|---|
| 4 | 215 | V* | C, D, E, F, H, K, N, P, Q, R |
| 4 | 218 | G | A, H, W |
| 4 | 220 | G* | M, Y |
| 4 | 223 | G | E, K, N, R, T |

*V215A and G220E are already substituted in SEQ ID NO: 2 so that a variant of SEQ ID NO: 2 would not contain a further substitution at these amino acid residues.

In one embodiment, the polypeptide is a variant of SEQ ID NO:1 having a modification that removes the putative glycosylation site at amino acids 39-41; and 2-9 additional amino acid substitutions, wherein one of the additional substitutions is a substitution set forth in Table 6 and Table 7; and at least one other of the substitutions is a substitution set forth in Table 1 and Table 2. In a more specific aspect of this embodiment, one of the additional substitutions is a substitution set forth in Table 6; and at least one other of the substitutions is a substitution set forth in Table 1. In an even more specific aspect of this embodiment, the polypeptide does not have a substitution in epitope 2. In another even more specific aspect of this embodiment, the polypeptide has a T41 substitution selected from T41G, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution.

In another embodiment, the polypeptide is a variant of SEQ ID NO:1 having a modification that removes the putative glycosylation site at amino acids 39-41; and has 3-9 additional amino acid substitutions, wherein at least one of the additional substitutions is selected from substitutions set forth in Table 6 and Table 7, and wherein at least two of epitopes 1, 2, and 3 contain at least one substitution selected from the substitutions set forth in Table 1 and Table 2. In a more specific aspect, the polypeptide has at least one of the substitutions set forth in Table 6 and at least one substitution in at least two of epitopes 1, 2 and 3 selected from the substitutions set forth in Table 1. In an even more specific aspect of this embodiment, the polypeptide does not have a substitution in epitope 2. In another even more specific aspect of this embodiment, the polypeptide has a T41 substitution selected from T41G, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution. In an alternate aspect of this embodiment, the polypeptide has only two additional substitutions, wherein on is in epitope 1 and the other is in epitope 3. In an even more specific aspect of this embodiment, the polypeptide has only two additional substitutions, wherein one is T56H and the other is K174R.

In another embodiment, the polypeptide is a variant of SEQ ID NO:1 having a modification that removes the putative glycosylation site at amino acids 39-41; and has 4-9 amino acid substitutions; at least one of substitutions set forth in Table 6 and Table 7; and at least one substitution in each of epitopes 1, 2 and 3 selected from the substitutions set forth in Table 1 and Table 2. In a specific aspect of this embodiment, the polypeptide has at least one of the substitutions set forth in Table 6 and at least one substitution in each of epitopes 1, 2 and 3 selected from those set forth in Table 1. In another more specific aspect, the polypeptide has at least one of substitutions set forth in Table 6; and at least one of the specific substitutions one, two or three amino acid substitutions set forth in Table 3, Table 4 or Table 5, respectively. In still another more specific aspect of this embodiment, the polypeptide is a variant of SEQ ID NO:1 and has only one of the amino acid substitutions set forth in Table 6 and only one, two or three additional amino acid substitutions selected from one of the specific one, two or three amino acid substitutions set forth in Table 3. Table 4 or Table 5, respectively. In another even more specific aspect of this embodiment, the polypeptide has a T41 substitution selected from T41G, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution.

In an alternate embodiment, the polypeptide is a variant of SEQ ID NO:2 having a modification that removes the putative glycosylation site at amino acids 39-41; and 1 to 9 additional amino acid residue substitutions selected from the group of amino acid substitutions set forth in Table 1, and Table 2. In a more specific aspect, at least one additional substitution is set forth in Table 1. In an even more specific aspect of this embodiment, the polypeptide does not have a substitution in epitope 2. In another even more specific aspect of this embodiment, the polypeptide has a T41 substitution selected from T41G, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution.

In another embodiment, the polypeptide is a variant of SEQ ID NO:2 having a modification that removes the putative glycosylation site at amino acids 39-41; and 2-9 additional amino acid substitutions and at least one substitution in at least two of epitopes 1, 2 and 3 selected from any of the substitutions set forth in Table 1 and 2. In a more specific aspect, at least one substitution in at least two of epitopes 1, 2 and 3 is selected from those set forth in Table 1. In an even more specific aspect of this embodiment, the polypeptide does not have a substitution in epitope 2. In another even more specific aspect of this embodiment, the polypeptide has a T41 substitution selected from T41G, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution. In an alternate aspect of this embodiment, the polypeptide comprises at least one amino acid substitution in epitope 1 and at least one amino acid substitution in epitope 3. In an even more specific aspect of this embodiment, the polypeptide comprises a T56H and a K174R substitution.

In another more specific aspect, the polypeptide is a variant of SEQ ID NO:2 or SEQ ID NO:5 and has 3-9 amino acid substitutions, wherein at least one substitution is in each of epitopes 1, 2 and 3 and is selected from any of the substitutions set forth in Table 1 and 2. In a more specific aspect, the at least one substitution in each of epitopes 1, 2 and 3 is selected from those set forth in Table 1. In an even more specific embodiment, the polypeptide is a variant of SEQ ID NO:2 or SEQ ID NO:5 and has only one, two or three amino acid substitutions selected from one of the specific one, two or three amino acid substitutions set forth in Table 3, Table 4 or Table 5, respectively. In another even more specific aspect of this embodiment, the polypeptide has a T41 substitution selected from T41F, T41W, T41H, T41V, T41I, T41L, T41R, T41K, T41Y, T41F, T41D, T41E, T41Q, T41N, and T41A. In a still more specific aspect of this embodiment, the polypeptide has a T41G substitution.

In another embodiment, the polypeptide of the invention is a variant of SEQ ID NO:2 having a T41 substitution selected from T41G, T41W, T41H, T41V, T41I, T41L, T41R, T41K, T41Y, T41F, T41D, T41E, T41Q, T41N, and T41A; and only 2 additional amino acid substitutions selected from any of the specific two amino acid substitutions set forth in Table 4. In a specific aspect of this embodiment, the polypeptide has a T41G substitution. In a more specific aspect of this embodiment, the polypeptide has a T41G substitution. In another more specific aspect of this embodiment, one additional amino acid substitution is in epitope 1 and the other additional amino acid substitution is in epitope 3. In a still more specific aspect of this embodiment, one additional amino acid substitution is T56H and the other additional amino acid substitution is K174R. In an even more specific aspect of this embodiment, the polypeptide has the amino acid sequence set forth in SEQ ID NO:5

In another embodiment, the polypeptide of the invention is a variant of SEQ NO:2 having, a T41 substitution selected from T41G, T41W, T41H, T41V, T41I, T41L, T41R, T41K, T41Y, T41F, T41D, T41E, T41Q, T41N, and T41A; and only 3 additional amino acid substitutions selected from any of the specific three amino acid substitutions set forth in Table 5. In a specific aspect of this embodiment, the polypeptide has a T41G substitution.

Nucleic Acid Molecules, Sequences, Vectors and Host Cells

In other embodiments, the invention provides an isolated nucleic acid molecule that comprises a nucleic acid sequence coding for any of the polypeptides or fusion proteins comprising a g3p variant described above. In one aspect of this embodiment, the isolated nucleic acid molecule comprises a variant of nucleotides 64-714 of SEQ ID NO:3 or nucleotides 64-708 of SEQ ID NO:5, that is modified by a codon substitution, an in-frame codon insertion or an in-frame codon deletion that destroys the putative glycosylation site encoded by nucleotides 181-189 of SEQ ID NOS:3 or 4 (corresponding to the amino acids NAT at amino acids 39-41 of SEQ ID NOS:1 or 3). In a more specific aspect of these embodiments, the variant of nucleotides 64-714 of SEQ ID NOS:3 or 4 is modified by a codon substitution that destroys the putative glycosylation site encoded by nucleotides 181-189 of SEQ ID NOS:3 or 4. In an even more specific aspect of these embodiments, the variant of nucleotides 64-714 of SEQ ID NOS:3 or 4 is modified by a codon substitution at nucleotides 187-189 (which encodes T41 of SEQ ID NOS:1 and 2) that encodes an amino acid substitution selected from T41G, T41W, T41H, T41V, T41I, T41L, T41R, T41K, T41Y, T41F, T41D, T41E, T41Q, T41N, and T41A. In an even more specific aspect of these embodiments, the substituted codon substitution is selected from gga, tgg, cat, gtt, att, ctt, agg, aaa, tat, ttc, gac, gag, cag, aat, and gct. In an even more specific aspect of these embodiments, the variant of nucleotides 64-714 of SEQ ID NOS:3 or 4 is modified by a codon substitution at nucleotides 187-189 that encodes the amino acid substitution T41G. In an even more specific aspect of these embodiments, the substituted codon substitution is gga.

In another embodiment, in addition to the modification that destroys the putative glycosylation site encoded by nucleotides 181-189 of SEQ ID NOS:3 or 4, the variant of nucleotides 64-714 of SEQ ID NOS:3 or 4 further consists of 1-9 codon substitutions, wherein each codon substitution corresponds to an amino acid substitution selected from the substitutions set forth in Table 1, and Table 2, and any one of the following V215 amino acid substitutions: V215A, V215S, V215G or V215T, V215C, V215D, V215E, V215F, V215H, V215K, V215N, V215P, V215Q, and V215R. In an even more specific aspect of these embodiments the variant nucleic acid sequence is modified by one codon substitution selected to code for any one of the V215 amino acid substitutions set forth above; and from 1-8 additional codon substitutions, wherein each of the additional codon substitutions is selected to code for an amino acid substitution set forth in Table 1. In a still more specific aspect of these embodiments the variant nucleic acid sequence is modified by one codon substitution selected to code for any one of the V215 amino acid substitutions set forth above; and from 2-8 additional codon substitutions, wherein each additional codon substitutions encodes an amino acid substitution set forth in Table 1, and a codon substitution is present in each of at least two of epitopes 1, 2 and 3. In a still more specific embodiment, the variant nucleic acid sequence is modified by one codon substitution selected to code for any one of the V215 amino acid substitutions set forth above; and from 3-8 additional codon substitutions, wherein each additional codon substitution encodes an amino acid substitution set forth in Table 1, and a codon substitution is present in each of epitopes 1, 2 and 3. In a still more specific embodiment, the variant nucleic acid sequence is modified by one codon substitution selected to code for a V215A amino acid substitution; and one additional codon substitution selected to code for one of the single amino acid substitutions set forth in Table 3. In a more specific aspect of this embodiment, the one additional codon substitution selected to code for one of the single amino acid substitutions set forth in Table 3 does not code for an amino acid substitution in epitope 2, In another specific embodiment, the variant nucleic acid sequence is modified by one codon substitution selected to code for a V215A amino acid substitution set forth above; and two additional codon substitutions selected to code for one of the specific two amino acid substitutions set forth in Table 4. In a more specific aspect of this embodiment, the two additional codon substitutions selected to code for one of the specific two amino acid substitutions set forth in Table 4 does not code for an amino acid substitution in epitope 2. In a still more specific embodiment, the variant nucleic acid sequence is modified by one codon substitution selected to code for a V215 amino acid substitution set forth above; and three additional codon substitutions selected to code for one of the specific three amino acid substitutions set forth in Table 5.

In still other embodiments, the isolated nucleic acid molecule comprises a variant of nucleotides 64-1530 of SEQ ID NO:3 or nucleotides 64-1524 of SEQ ID NO:6, wherein the sequence is modified by a codon substitution, an in-frame codon insertion or an in-frame codon deletion that destroys the putative glycosylation site encoded by nucleotides 181-189 of SEQ ID NOS:3 or 4 (corresponding to the amino acids NAT at amino acids 39-41 of SEQ ID NOS:1 or 3). In a more specific aspect of these embodiments, the variant of nucleotides 64-1530 of SEQ ID NO:3 or nucleotides 64-1524 of SEQ ID NO:4 is modified by a codon substitution that destroys the putative glycosylation site encoded by nucleotides 181-189 of SEQ ID NOS:3 or 4. In an even more specific aspect of these embodiments, the variant of nucleotides 64-1530 of SEQ ID NO:3 or nucleotides 64-1524 of SEQ ID NO:4 is modified by a codon substitution at nucleotides 187-189 (aca, which encodes T41 of SEQ ID NOS:1 and 2) that encodes an amino acid substitution selected from T41G, T41W, T41H, T41V, T41I, T41L, T41R, T41K, T41Y, T41F, T41D, T41E, T41Q, T41N, and T41A. In an even more specific aspect of these embodiments, the substituted codon substitution is selected from gga, tgg, cat, gtt, att, ctt, agg, aaa, tat, ttc, gac, gag, cag, aat, and gct. In an even more specific aspect of these embodiments, the variant of nucleotides 64-714 of SEQ ID NOS:3 or 4 is modified by a codon substitution at nucleotides 187-189 that encodes the amino acid substitution T41G. In an even more specific aspect of these embodiments, the substituted codon substitution is gga In another embodiment, in addition to the modification that destroys the putative glycosylation site encoded by nucleotides 181-189 of SEQ ID NOS:3 or 4, the variant of nucleotides 64-1530 of SEQ ID NO:3 or nucleotides 64-1524 of SEQ ID NO:4 further consists of 1-9 codon substitutions, wherein each codon substitution corresponds to an amino acid substitution selected from the substitutions set forth in Table 1, Table 2, and any one of the following V215 amino acid substitutions: V215S, V215G or V215T, V215C, V215D, V215E, V215F, V215H, V215K, V215N, V215P, V215Q, and V215R. In a more specific aspect of this embodiment, each codon substitution corresponds to an amino acid substitution selected from the substitutions set forth in Table 1, and any one of the V215 substitutions set forth above. In an even more specific embodiment, the variant nucleic acid sequence is modified by one codon substitution selected to code for any one of the V215 amino acid substitutions set forth above and from 1-8 additional codon substitutions, wherein each of the additional codon substitutions corresponds to an amino acid substitution selected from the substitutions set forth in Table 1. In a more specific aspect, the variant has one additional codon substitution corresponding to one of the specific one amino acid substitutions set forth in Table 3. In a more specific aspect of this embodiment, the one additional codon substitution selected to code for one of the single amino acid substitutions set forth in Table 3 does not code for an amino acid substitution in epitope 2.

In another embodiment, in addition to the modification that destroys the putative glycosylation site encoded by nucleotides 181-189 of SEQ ID NOS:3 or 4, the variant of nucleotides 64-1530 of SEQ ID NO:3, or nucleotides 64-1524 of SEQ ID NO:6 has a modification that consists of one codon substitution selected to code for any one of the V215 amino acid substitution set forth above; and from 2-8 additional codon substitutions, wherein each additional codon substitution corresponds to an amino acid substitution set forth in Table 1, and a codon substitution is present in each of at least two of epitopes 1, 2 and 3. In a more specific aspect, the variant has two additional codon substitutions corresponding to one of the specific two amino acid substitutions set forth in Table 4. In a more specific aspect of this embodiment, the two additional codon substitutions selected to code for one of the specific two amino acid substitutions set forth in Table 4 does not code for an amino acid substitution in epitope 2. In an even more specific aspect of this embodiment, the specific two amino acid substitutions from Table 4 is T56H and K74I. In an even more specific aspect of this embodiment, the variant nucleotide sequence is SEQ ID NO:8.

In another embodiment, in addition to the modification that destroys the putative glycosylation site encoded by nucleotides 181-189 of SEQ ID NOS:3 or 4, the variant of any one of nucleotides 64-1530 of SEQ ID NO:3, or nucleotides 64-1524 of SEQ ID NO:6, has a modification that consists of one codon substitution selected to code for any one of the V215 amino acid substitution set forth above; and from 3-8 additional codon substitutions, wherein each additional codon substitution corresponds to an amino acid substitution set forth in Table 1, and a codon substitution is present in each of epitopes 1, 2 and 3. In a more specific aspect, the variant has three additional codon substitutions corresponding to one of the specific three amino acid substitutions set forth in Table 5.

In still other embodiments of the nucleic acid molecules of the invention, the nucleic acid molecule further comprises nucleic acid sequences encoding a signal sequence fused in phase and directly to the 5' end of the nucleic acid sequence encoding the variant g3p. In one aspect of these embodiments, the nucleic acid sequence encoding the signal sequence is nucleotides 1-63 of SEQ ID NO:3.

The nucleic acid molecules of the invention encompass nucleic acid sequences that are degenerative to, but encode the same amino acid sequence as encoded by any of the nucleic acid nucleic acid molecules described above.

For recombinant production, any of the nucleic acid molecules of the invention may be inserted into an appropriate expression vector which contains the necessary elements for the transcription and translation of the inserted coding sequence, or in the case of an RNA viral vector, the necessary elements for replication and translation. The encoding nucleic acid is inserted into the vector in proper reading frame. Accordingly, the invention provides vectors comprising nucleic acid molecule and sequences of the invention. Such vectors include, but are not limited to, DNA vectors, phage vectors, viral vectors, retroviral vectors, etc. The choice of appropriate vector in which to clone the nucleic acid molecules and sequences of the invention may be made by those of skill in the art using well-known knowledge of the compatibility of the vector with the chosen host cell in which to carry out expression. This may be done in any of mammalian cells, plant cells, insect cells, bacterial cells, yeast cells, etc. Appropriate vectors for each of these cell types are well-known in the art and are generally commercially available.

In another embodiment, the invention provides a host cell harboring the vector containing a nucleic acid molecule or nucleic acid sequence of the invention. Methods of transfecting or transforming or otherwise getting a vector of the invention into a host cell are known in the art. A cell harboring the vector, when cultured tinder appropriate conditions, will produce the polypeptides of the invention. Specific examples of vectors and cells used for the recombinant production of the polypeptides of the invention are set forth in the example section below.

Pharmaceutical Compositions

In some embodiments, the invention provides a pharmaceutical composition comprising any polypeptide or fusion protein comprising a variant g3p, optionally together with a pharmaceutically acceptable carrier, diluent or excipient. A "pharmaceutical composition" refers to a therapeutically effective amount of a composition as described herein with a physiologically suitable carrier and/or excipient. A pharmaceutical composition does not cause significant irritation to an organism. The phrases "physiologically suitable carrier" and "pharmaceutically acceptable carrier" which may be used interchangeably refer to a carrier or a diluent that does not cause significant irritation to an organism and does not abrogate the biological activity and properties of the administered composition. The term "excipient" refers to an inert substance added to a pharmaceutical composition to further facilitate administration of an active ingredient. Examples, without limitation, include, few example, saline, calcium carbonate, calcium phosphate, various sugars and types of starch, cellulose derivatives, gelatin, vegetable oils, polyethylene glycols, and surfactants, including, for example, polysorbate 20.

Pharmaceutical compositions for use in accordance with the present invention may be formulated in a conventional manner using one or more physiologically acceptable carriers comprising excipients and auxiliaries, which facilitate processing of the active ingredients into compositions which can be used pharmaceutically. Proper formulation is dependent upon the route of administration chosen and upon the nature of the composition delivered (e.g., size and solubility of the polypeptide). In one aspect of these embodiments, the pharmaceutical composition is formulated for injection or infusion into the bloodstream of a patient. In another aspect of these embodiments, the pharmaceutical composition is formulated for direct administration to the brain or central nervous system of the patient, for example, by direct intramedullary, intrathecal, or intraventricular injection.

The compositions described herein may be formulated for parenteral administration, e.g., by bolus injection or continuous infusion. Pharmaceutical compositions for parenteral administration include aqueous solutions of the composition in water-soluble form. Additionally, suspensions of the active ingredients may be prepared as oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents (e.g., surfactants such as polysorbate (Tween 20)) which increase the solubility of the active ingredients to allow for the preparation of highly concentrated solutions. A protein based agent such as, for example, albumin may be used to prevent adsorption of polypeptide of the invention to the delivery surface (i.e., bag, catheter, needle, etc.).

For oral administration, the compositions can be formulated readily b combining the active compounds with pharmaceutically acceptable carriers well known in the art.

Formulations may be presented in unit dosage form, e.g., in vials, ampoules or in multidose containers with optionally, an added preservative. The compositions may be suspensions, solutions or emulsions in oily or aqueous vehicles, and may contain formulatory agents such as suspending, stabilizing and/or dispersing agents. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, such as by infusion, or via an implanted pump, such as an ICV pump. In the latter embodiment, the single dosage form may be an infusion bag or pump reservoir pre-filled with the appropriate amount of a polypeptide or fusion protein comprising a variant g3p. Alternatively, the infusion bag or pump reservoir may be prepared just prior to administration to a patient by mixing an appropriate dose of the variant g3p with the infusion bag or pump reservoir solution.

Another aspect of the invention includes methods for preparing a pharmaceutical composition of the invention. Techniques for formulation of drugs may be found, for example, in "Remington's Pharmaceutical Sciences," Mack Publishing Co., Easton, Pa., latest edition, which is incorporated herein by reference in its entirety.

Pharmaceutical compositions suitable for use in the context of the present invention include compositions wherein the active ingredients are contained in an amount effective to achieve the intended purpose.

Determination of a therapeutically or diagnostically effective amount is well within the capability of those skilled in the art, especially in light of the detailed disclosure provided herein.

Dosage amount and interval may be adjusted individually to provide brain levels of the phage display vehicle which are sufficient to treat or diagnose a particular brain disease, disorder, or condition (minimal effective concentration, MEC). The MEC will vary for each preparation, but can be estimated from in vitro data. Dosages necessary to achieve the MEC will depend on individual characteristics.

Dosage intervals can also be determined using the MEC value. Preparations should be administered using a regimen, which maintains brain levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated or diagnosed, the severity of the affliction, the judgment of the prescribing physician, etc. In certain embodiments, the amount of polypeptide to be administered is selected from 0:1-100 mg/kg, subject body weight; 0.5-50 mg/kg; 1-30 mg/kg; 1-10 mg/kg; 3-30 mg/kg; 1-3 mkg/kg; 3-10 mg/kg; and 10-30 mg/kg. In some embodiments, the peptide is administered to the subject once a week, once every two weeks, once every three weeks, once every four weeks, or once a month.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is to be understood that both the foregoing and following description are exemplary and explanatory only and are not restrictive of the invention, as claimed.

Therapeutic Uses

Another aspect of the invention relates to the use of any of the polypeptides, nucleic acid molecules, or compositions of the invention, in the treatment of protein misfolding diseases, including, but not limited to, those diseases involving any of: fAβ42, fαsym or ftau.

In the context of treatments, the terms "patient", "subject" and "recipient" are used interchangeably and include humans as well as other mammals. In some embodiments, a patient is a human who is positive for a biomarker associated with a protein misfolding disease. In one embodiment, the patient exhibits β-amyloid deposits as detected by PET imaging, with florbetapir.

The term "treating" and its cognates are intended to mean reducing, slowing, or reversing the progression of a disease in a patient exhibiting one or more clinical symptoms of a disease. "Treating" is also intended to mean reducing, slowing, or reversing the symptoms of a disease in a patient exhibiting one more clinical symptoms of a disease. In one embodiment, the patient exhibits β-amyloid deposits as detected by PET imaging with florbetapir and the number of β-amyloid deposits is reduced by the treatment. In one embodiment, the patient exhibits β-amyloid deposits as detected by the polypeptide or polypeptide compositions of the present invention and the number of β-amyloid deposits are reduced or maintained by the treatment. In another embodiment, the patient exhibits any type of amyloid deposits as detected by PET imaging and the cognitive function of the patient is improved by the treatment. Improvement in cognitive function may be assayed by the methods and tests of McKharm et al., *Alzheimer's & Dementia* 7(3):263-9 (2011).

"Prophylaxis" is distinct from treating, and refers to administration of a composition to an individual before the onset of any clinical symptoms. Prophylaxis using any of the polypeptides or compositions thereof of the present invention is encompassed. Prophylaxis may be implicated in individuals who are known to be at increased risk for a disease, or whom are certain to develop a disease, solely on the basis of one or more genetic markers. Many genetic markers have been identified for the various protein misfolding diseases. For examples, individuals with one or more of the Swedish mutation, the Indiana mutation, or the London mutation in human amyloid precursor protein (hAPP) are at increased risk for developing early-onset Alzheimer's Disease and so are candidates for prophylaxis. Likewise, individuals with the trinucleotide CAG repeats in the huntingtin gene, particularly those with 36 or more repeats, will eventually develop Huntington's Disease and so are candidates for prophylaxis.

The term "protein misfolding" refers to diseases characterized by formation of amyloid protein by an aggregating protein (amyloid forming peptide), such as, but not limited to, β-amyloid, serum amyloid A, cystatin C, IgG kappa light chain, or a prion protein. Diseases known to be associated with misfolded and/or aggregated amyloid protein include Alzheimer's disease, which includes early onset Alzheimer's disease, late onset Alzheimer's disease, and presymptomatic Alzheimer's disease, Parkinson's disease, SAA amyloidosis, cystatin C, hereditary Icelandic syndrome, senility, multiple myeloma, prion diseases including but not limited to kuru, Creutzfeldt-Jakob disease (CCD), Gerstmarm-Straussler-Scheinker disease (GSS), fatal familial insomnia (FFI), scrapie, and bovine spongiform encephalitis (BSE); amyotrophic lateral sclerosis (ALS), spinocerebellar ataxia (SCA1), (SCA3), (SCA6), (SCA7), Huntington disease, entatorubral-pallidoluysian atrophy, spinal and bulbar muscular atrophy, hereditary cerebral amyloid angiopathy, familial amyloidosis, frontotemporal lobe dementia, British/Danish dementia, Progressive Supranuclear Palsy (PSP), and familial encephalopathy. The polypeptides and compositions of the invention may be used to treat "protein misfolding" diseases.

Many of these misfolded and/or aggregated amyloid protein diseases occur in the central nervous system (CNS), Some examples of diseases occurring in the CNS are Parkinson's Disease; Alzheimer's Disease; frontotemporal dementia (FTD) including those patients having the following clinical syndromes: behavioral variant FTD (bvFTD), progressive non-fluent aphasia (PNFA) and semantic dementia (SD); frontotemporal lobar degenerations (FTLDs); and Huntington's Disease. The polypeptides and compositions of the invention may be used to treat diseases characterized by misfolded and/or aggregated amyloid protein that occur in the central nervous system (CNS).

Misfolding and/or aggregation of proteins may also occur outside the CNS. Amyloidosis A (AA) (for which the precursor protein is serum acute phase apolipoprotein, SAA) and multiple myeloma (precursor proteins immunoglobulin light and/or heavy chain) are two widely known protein misfolding and/or aggregated protein diseases that occur outside the CNS. Other examples include disease involving amyloid formed by α2-microglobulin, transthyretin Amyloidotic Polyneuropathy [FAP], Familial Amyloidotic Cardiomyopathy [FAC], and Senile Systemic Amyloidosis [SSA], (apo)serum. AA, apolipoproteins AI, AII, and AIV, gelsolin (Finnish form of Familial Amyloidotic Polyneuropathy), lysozyme, fibrinogen, cystatin C (Cerebral Amyloid Angiopathy, Hereditary Cerebral Hemorrhage with Amyloidosis, Icelandic Type), (pro)calcitonin, islet amyloid polypeptide (IAPP amyloidosis), atrial natriuretic factor, prolactin, lactahedrin, kerato-epithelin, lactoferrin, odontogenic ameloblast-associated protein, and semenogelin I. The polypeptides and compositions of the invention may be used to treat diseases involving misfolding and/or aggregation of proteins that occur outside the CNS.

Neurodegenerative diseases may also involve tau lesions. Reviewed in Lee et al., *Annu. Rev. Neurosci.* 24:1121-159 (2001). Tau proteins are microtubule-associated proteins expressed in axons of both central and peripheral nervous system neurons. Neurodegenerative tauopathies (sometimes referred to as tauopathies) are encompassed. Examples of tauopathies include Alzheimer's Disease, Amyotrophic lateral sclerosis/parkinsonism-dementia complex, Argyophilic grain dementia, Corticobasal degeneration, Creutzfeldt-Jakob disease, Dementia pugilistica, diffuse neurofibriliary tangles with calcification, Down's syndrome, Frontotemporal dementias including frontotemporal dementia with parkinsonism linked to chromosome 17, Gerstmann-Sträussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, and Tangle only dementia. Some of these diseases may also include deposits of fibrillar amyloid β peptides. For example, Alzheimer's disease exhibits both amyloid β deposits and tau lesions. Similarly, prion-mediated diseases such as Creutzfeldt-Jakob disease, prion protein cerebral amyloid angiopathy, and Gerstmann-Sträussler-Scheinker syndrome may have also have tau lesions. Thus an indication that a disease is a "taupathy" should not be interpreted as excluding the disease from other neurodegenerative disease classifications or groupings, which are provided merely as a convenience. The polypeptides and compositions of the invention may be used to treat neurodegenerative diseases as well as diseases involving tau lesions.

In one embodiment, a pharmaceutical composition or formulation is for use in a method of reducing amyloid in a patient exhibiting symptoms related to the presence of amyloid or that is positive for a biomarker associated with a protein misfolding disease, such as florbetapir (AV-45, Eli Lilly), comprising administering to the patient an effective amount of a pharmaceutical composition or formulation as described herein. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation is for use in a method of maintaining the level of amyloid in a patient exhibiting symptoms related to the presence of amyloid or that is positive for a biomarker associated with a protein misfolding disease, such as florbetapir (AV-45, Eli Lilly), comprising administering to the patient an effective amount of a pharmaceutical composition or formulation as described herein. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation is for use in a method of disaggregating amyloid in a patient comprising administering to a patient having amyloid an effective amount of a pharmaceutical composition or formulation as described herein. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method of causing the disaggregation of β-amyloid deposits in the brain, comprising injecting directly into the brain of a patient in need thereof an effective amount of pharmaceutical composition as described herein, thereby causing a reduction in β-amyloid deposits in the brain. In an alternate embodiment, a pharmaceutical composition or formulation of the invention is for use in a method of causing the disaggregation of β-amyloid deposits in the brain, comprising injecting intravenous delivery into a patient in need thereof an effective amount of pharmaceutical composition as described herein, thereby causing a reduction in β-amyloid deposits in the brain.

I one embodiment, a pharmaceutical composition or formulation is for use in a method of reducing amyloid formation in the brain. Reducing amyloid formation in the brain may prevent, treat or reduce the symptoms or severity of a protein-misfolding or neurodegenerative disease. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method for promoting amyloid clearance in the brain. Promoting amyloid clearance may prevent, treat or reduce the symptoms or severity of a protein-misfolding or neurodegenerative disease. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method for inhibiting amyloid aggregation in the brain. Inhibiting amyloid aggregation in the brain may prevent, treat or reduce the symptoms or severity of a protein-misfolding or neurodegenerative disease, in one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method for clearing toxic amyloid oligomers in the brain. Clearing, toxic amyloid oligomers in the brain may prevent, treat or reduce the symptoms or severity of a protein-misfolding or neurodegenerative disease. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method for preventing the formation of toxic amyloid oligomers in the brain. Preventing the formation of toxic oligomers in the brain may prevent, treat or reduce the symptoms or severity of a protein-misfolding or neurodegenerative disease. In one embodiment, the route of administration is selected from intrathecal injection or infusion, direct intraventricular injection or infusion, intraparenchymal injection or infusion, or intravenous injection or infusion.

In one embodiment, a pharmaceutical composition or formulation of the invention is for use in a method for protecting neurons from amyloid damage. Protecting neurons from amyloid damage may prevent, treat or reduce the symptoms or severity of a protein-misfolding or neurodegenerative disease. In one embodiment, the route of administration is selected from intrathecal injection or infusion, direct intraventricular injection or infusion, intraparenchymal injection or infusion, or intravenous injection or infusion. In one embodiment, a pharmaceutical composition or formulation of the invention for use in protecting neurons from amyloid damage is given prophylactically.

In some embodiments, the patient is positive for a biomarker associated with a protein misfolding and/or aggregation disease. In one embodiment, the biomarker is florbetapir (AV45, Eli Lilly).

In some embodiments, the patient is exhibiting symptoms of a neurodegenerative disease that is associated with the presence of amyloid. In various embodiments, the amyloid is any of fAβ42, fαsyn or ftau.

In certain embodiments, the neurodegenerative disease is Parkinson's disease, Alzheimer's disease, or Huntington's disease. In one embodiment, the neurodegenerative disease is Alzheimer's disease. In one embodiment, the neurodegenerative disease is Alzheimer's disease and the patient exhibits β-amyloid as detected by the imaging agent florbetapir (AV-45, Eli Lilly).

In some embodiments, the patient is exhibiting symptoms of a prion-mediated disease.

In certain embodiments, the prion-mediated disease is chosen from Creutzfeldt-Jakob disease, kuru, fatal familial insomnia, or Gerstmann-Sträussler-Scheinker syndrome.

In some embodiments, the patient is exhibiting symptoms of a neurodegenerative tauopathy other than Alzheimer's disease. In certain embodiments, the disease to be treated is selected from Argyrophilic grain dementia, Corticobasal degeneration, Dementia pugilistica, diffuse neurofibrillary tangles with calcification, Down's syndrome, Frontotemporal dementias including frontotemporal dementia with parkinsonism linked to chromosome 17, Hallervorden-Spatz disease, Myotonic dystrophy, Niemann-Pick disease type C, Non-Guamanian motor neuron disease with neurofibrillary tangles, Pick's disease, Postencephalitic parkinsonism, Progressive subcortical gliosis, Progressive supranuclear palsy, Subacute sclerosing panencephalitis, and Tangle only dementia.

In another embodiment, any of the disease conditions described above may be treated by administration of a nucleic acid molecule of the invention (i.e., one that encodes a variant g3p that exhibits reduced immunogenicity and possessing the ability to bind to amyloid, disaggregate amyloid plaques, and/or prevent aggregation of amyloid) alone or associated with a suitable carrier, such as, e.g., a lipid nanoparticle, a polymeric carrier, or a vector, such as a viral vector directly to a patient by any suitable route, such as, e.g., inhalation and intravenous infusion. The nucleic acid molecule encoding the variant g3p of the invention suitable for this treatment may be DNA or RNA.

Diagnostics

In another aspect of the invention, the polypeptides and compositions described herein, are used in diagnostic applications associated with the various diseases described herein. For example, binding of a composition of the invention when used as an imaging agent either in vivo or in vitro may be part of a diagnosis of one of the protein misfolding diseases described. When used as diagnostic agents, the polypeptides of the invention may further comprise a detectable label, or may be otherwise detected in vivo. Various labels can be attached to the amyloid binding component of the diagnostic composition using standard techniques for labeling, proteins. Examples of labels include fluorescent labels and radiolabels. There are a wide variety of radiolabels that can be used, but in general the label is often selected from radiolabels including, but not limited to, $^{18}F$, $^{11}C$, and $^{123}O$. These and other radioisotopes can be attached to the protein using well known chemistry. In one embodiment, the label is detected using positron emission tomography (PET). However, any other suitable technique for detection of radioisotopes may also be used to detect the radiotracer.

The polypeptides and compositions of the invention may be used as diagnostic imaging agents in combination with an imaging agent that is specific for β-amyloid such as, for example, F18-AV-45, Eli Lilly. Since there are currently no known imaging agents for non-β-amyloid aggregates, the use of a diagnostic composition of the invention together with a β-amyloid-specific imaging agent will result in the detection of non-β-amyloid aggregates based on differential detection. Thus, in one embodiment, a diagnostic composition of the invention is used as an imaging agent in combination with a β-amyloid imaging, agent to detect non-β-amyloid aggregates.

In another embodiment, the polypeptides or compositions of the invention is used as a diagnostic imaging, agent to detect β-amyloid in the CNS, including the brain.

Diagnostic compositions of the invention may be administered using the same routes described for therapeutic compositions. In one embodiment, the route of administration is selected from intrathecal injection or infusion, direct intraventricular injection or infusion, intraparenchymal injection or infusion, or intravenous injection or infusion.

EXAMPLES

Example 1: Mapping of CD4+ T Cell Epitopes in g3p 87 overlapping peptides spanning the sequence of amino acids 1-240 of SEQ ID NO:1 (15 amino acids long with 12 amino acid overlaps) were synthesized and tested in a T cell epitope mapping assay for responses from human CD4+ T cells. Individual peptides were tested in sextuplicate PBMC cultures and T cell responses were assessed in order to identify the location of epitopes as well as their relative potency.

PBMC (peripheral blood mononuclear cells) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee by Lymphoprep (Axis-shield, Dundee, UK) density centrifugation. $CD8^+$ T cells were depleted using $CD8^+$ RosetteSep™ (StemCell Technologies Inc, London, UK). Donors were characterized by identifying HLA-DR haplotypes using an HLA SSP-PCR based tissue-typing kit (Biotest, Solihull, UK). T cell responses to a control neoantigen protein (KLH protein (Pierce (Perbio), Cramlington, UK) and peptides derived from IFV and EBV) were also determined. PBMC were then frozen and stored in liquid nitrogen until required.

A cohort of 55 donors was selected for the assay to best represent the number and frequency of HLA-DR allotypes expressed in the world population, Analysis of the allotypes expressed in the cohort against those expressed in the world population revealed that coverage of >80% was achieved and that all major HLA-DR alleles (individual allotypes with a frequency >5% expressed in the world population) were well represented. Details of individual donor haplotypes and a comparison of the frequency of MHC class II haplotypes expressed in the world population and the sample population are shown in Table 8 and FIG. 3, respectively.

TABLE 8

Donor details and haplotypes

| Donor No. | Haplotype |
|---|---|
| 1 | DRB1*04:01, DRB1*16:01; DRB4*01:03; DQB1*03:02; DQB1*05:02 |
| 2 | DRB1*01:01, DRB1*13:02; DRB3*03:01; DQB1*05:01; DQB1*06:04 |
| 3 | DRB1*03:01, DRB1*07:01; DRB3*01:01; DRB4*01:03; DQB1*02:01; DQB1*03:03 |

TABLE 8-continued Donor details and haplotypes

| Donor No. | Haplotype |
|---|---|
| 4 | DRB1*09:01, DRB1*13:01; DRB3*02:02; DRB4*01:03; DQB1*03:03; DQB1*06:03 |
| 5 | DRB1*13:01, DRB1*13:02; DRB3*01:01; DRB3*03:01; DQB1*06:03; DQB1*06:04 |
| 6 | DRB1*04:01, DRB1*04:07; DRB4*01:03; DQB1*03:01 |
| 7 | DRB1*13:01; DRB3*01:01; DQB1*06:03 |
| 8 | DRB1*13:01, DRB1*15:01; DRB3*02:02; DRB5*01:01; DQB1*06:02; DQB1*06:03 |
| 9 | DRB1*04:01, DRB1*11:01; DRB3*02:02; DRB4*01:03; DQB1*03:01; DQB1*03:02 |
| 10 | DRB1*04:04, DRB1*12:01; DRB3*02:02; DRB4*01:03; DQB1*03:01; DQB1*03:02 |
| 11 | DRB1*13:02, DRB1*15:01; DRB3*01:01; DRB5*01:01; DQB1*06:02; DQB1*06:04 |
| 12 | DRB1*04:01, DRB1*15:01; DRB4*01:03; DRB5*01:01; DQB1*03:02; DQB1*06:02 |
| 13 | DRB1*04:02, DRB1*07:01; DRB4*01:01; DRB4*01:03; DQB1*02:01 |
| 14 | DRB1*03:01, DRB1*16:01; DRB3*01:01; DRB5*02:02; DQB1*02:01; DQB1*05:02 |
| 15 | DRB1*03:01, DRB1*13:01; DRB3*02:02; DQB1*02:01; DQB1*06:03 |
| 16 | DRB1*01:01, DRB1*15:01; DRB5*01:01; DQB1*05:01; DQB1*06:02 |
| 17 | DRB1*01:01, DRB1*07:01; DRB4*01:03; DQB1*03:03; DQB1*05:01 |
| 18 | DRB1*01:01, DRB1*09:01; DRB4*01:03; DQB1*03:03; DQB1*05:01 |
| 19 | DRB1*03:01, DRB1*11:02; DRB3*01:01; DRB3*02:02; DQB1*02:01; DQB1*03:01 |
| 20 | DRB1*13:01; DRB3*01:01; DRB3*02:02; DQB1*06:03 |
| 21 | DRB1*01:01, DRB1*13:02; DRB3*03:01; DQB1*05:01; DQB1*06:04 |
| 22 | DRB1*04:01, DRB1*04:03; DRB4*01:03; DQB1*03:02 |
| 23 | DRB1*08:01, DRB1*13:01; DRB3*01:01; DQB1*04:02; DQB1*06:03 |
| 24 | DRB1*03:01, DRB1*15:01; DRB3*01:01; DRB5*01:01; DQB1*02:01; DQB1*06:02 |
| 25 | DRB1*03:01, DRB4*01:01; DRB3*01:01; DRB4*01:03; DQB1*02:01; DQB1*03:01 |
| 26 | DRB1*01:01, DRB1*15:01; DRB5*01:01; DQB1*05:01; DQB1*06:02 |
| 27 | DRB1*04:04, DRB1*07:01; DRB4*01:01; DRB4*01:03; DQB1*02:02; DQB1*03:02 |
| 28 | DRB1*11:01, DRB1*15:01; DRB3*02:01; DRB5*01:01; DQB1*03:01; DQB1*06:01 |
| 29 | DRB1*08:01, DRB1*15:01; DRB5*01:01; DQB1*04:02; DQB1*06:02 |
| 30 | DRB1*13:02, DRB1*15:01; DRB3*01:01; DRB5*01:01; DQB1*06:02; DQB1*06:09 |
| 31 | DRB1*04:01, DRB1*16:01; DRB4*01:03; DRB5*02:02; DQB1*03:02; DQB1*06:03 |
| 32 | DRB1*13:02, DRB1*15:01; DRB3*03:01; DRB5*01:01; DQB1*06:02; DQB1*06:04 |
| 33 | DRB1*07:01, DRB1*11:04; DRB3*02:02; DRB4*01:01; DQB1*02:02; DQB1*03:01 |
| 34 | DRB1*01:03, DRB1*15:01; DRB5*01:01; DQB1*03:01; DQB1*06:02 |
| 35 | DRB1*03:01, DRB1*14:01; DRB3*01:01; DRB3*02:02; DQB1*02:01; DQB1*05:03 |
| 36 | DRB1*03:01, DRB1*08:01; DRB3*01:01; DQB1*02:01; DQB1*04:02 |
| 37 | DRB1*03:01, DRB1*11:01; DRB3*01:01; DRB3*02:02; DQB1*02:01; DQB1*03:01 |
| 38 | DRB1*07:01, DRB1*15:01; DRB4*01:03; DRB5*01:01; DQB1*02:02; DQB1*06:02 |
| 39 | DRB1*03:01, DRB1*13:02; DRB3*02:02; DRB3*03:01; DQB1*02:01; DQB1*06:09 |
| 40 | DRB1*01:01, DRB1*13:02; DRB3*01:01; DQB1*05:01; DQB1*06:04 |
| 41 | DRB1*04:07, DRB1*15:01; DRB4*01:03; DRB5*01:01; DQB1*03:01; DQB1*06:02 |
| 42 | DRB1*07:01; DRB4*01:03; DQB1*02:02; DQB1*03:03 |
| 43 | DRB1*03:01, DRB1*15:01; DRB3*01:05; DRB5*01:01; DQB1*02:01; DQB1*06:02 |
| 44 | DRB1*07:01, DRB1*11:04; DRB3*02:02; DRB4*01:01; DQB1*02:02; DQB1*03:01 |
| 45 | DRB1*03:01, DRB1*04:04; DRB3*01:01; DRB4*01:03; DQB1*02:01; DQB1*03:02 |
| 46 | DRB1*04:04, DRB1*13:01; DRB3*02:02; DRB4*01:03; DQB1*03:02; DQB1*06:03 |
| 47 | DRB1*04:01, DRB1*11:01; DRB3*02:02; DRB4*01:03; DQB1*03:01 |
| 48 | DRB1*03:01, DRB1*04:01; DRB3*01:06; DRB4*01:03; DQB1*02:01; DQB1*03:02 |
| 49 | DRB1*01:02, DRB1*13:03; DRB3*01:01; DQB1*03:01; DQB1*05:01 |
| 50 | DRB1*04:07, DRB1*15:01; DRB4*01:03; DRB5*01:01; DQB1*03:01; DQB1*06:02 |
| 51 | DRB1*04:07, DRB1*13:02; DRB3*01:01; DRB4*01:03; DQB1*03:01; DQB1*06:04 |
| 52 | DRB1*03:01; DRB3*01:05; DQB1*02:01 |
| 53 | DRB1*03:01, DRB1*07:01; DRB3*01:01; DRB4*01:01; DQB1*02:01; DQB1*02:02 |
| 54 | DRB1*04:04, DRB1*15:01; DRB4*01:03; DQB1*03:02; DQB1*06:02 |
| 55 | DRB1*03:01, DRB1*04:01; DRB3*01:01; DRB4*01:03; DQB1*02:01; DQB1*03:01 |

PBMC from each donor were thawed, counted and viability was assessed. Cells were revived in room temperature AIM-V® culture medium (Invitrogen, Paisley, UK) before adjusting the cell density to 2-3×10$^6$ PBMC/ml (proliferation cell stock). The 15 amino acid long peptides were synthesized on a 1-3 mg scale with free N-terminal amine and C-terminal carboxylic acid. Peptides were dissolved in DMSO to a concentration of 10 mM and peptide culture stocks prepared by diluting into AIM-V® culture medium to a final concentration of 5 μM in the well. For each peptide and each donor, sextuplicate cultures were established in a flat bottomed 96 well plate. Both positive and negative control cultures were also tested in sextuplicate. For each donor, three controls (KLH protein and peptides derived from IFV and EBV) were also included. For a positive control, PHA (Sigma, Dorset, UK) was used at a final concentration of 2.5 μg/ml.

Cultures were incubated for a total of 6 days before adding 0.75 μCi $^3$[H]-thymidine (Perkin Elmer®, Beaconsfield, UK) to each well. Cultures were incubated for a further 18 hours before harvesting onto filter mats using a TomTec Mach III cell harvester. Cpm for each well were determined by Meltilex™ (Perkin Elmer®, Beaconsfield, UK) scintillation counting on a Microplate Beta Counter (Perkin Elmer®, Beaconsfield, UK) in paralux, low background counting mode.

For analysis of the data, a threshold of a stimulation index (SI) equal to or greater SI≥2.00 was used (with consideration of borderline SI≥1.90-1.99 responses). Positive responses were defined by the following statistical and empirical thresholds:

1. Significance ($p<0.05$) of the response by comparing cpm of test wells against medium control wells using unpaired two sample Student's t-test;

2. Stimulation index greater than 2.00 (SI≥2.00), where SI=mean cpm of test wells/mean cpm medium control wells. Data presented in this way is indicated as SI≥2.00, p<0.05.

In addition, intra-assay variation was assessed by calculating the CV and SD of the raw data from replicate cultures. Proliferation assays were set up in sextuplicate cultures ("non-adjusted data"). To ensure that intra-assay variability was low, the data were also analysed after removing the maximum and minimum cpm values ("adjusted data") and the SI of donor responses was compared using both data sets. T cell epitopes were identified by calculating the average frequency of positive responses (defined above) to all peptides in the study plus SD to give a background response rate. Any peptide that induced proliferative responses above the background response rate in both the adjusted and non-adjusted data was considered to contain a T cell epitope. When two overlapping peptides induced a proliferative response rate the T-cell epitope was considered to be in the overlap region. Based upon this the following T-cell epitopes were identified in the tested polypeptide:

(amino acids 46-57 of SEQ ID NO: 1)
Epitope 1: C T G D E T Q C Y G T W (amino acids 133-144 of SEQ ID NO: 1)
Epitope 2: T F M F Q N N R F R N R (amino acids of 172-183 of SEQ ID NO: 1)
Epitope 3: S S K A M Y D A Y W N G (amino acids 214-225 of SEQ ID NO: 1)
Epitope 4: P V N A G G G S G G G S (amino acids 253-267 of SEQ ID NO: 1)
Epitope 5: S G S G A M V R S D K T H T C

Example 2: Design of Substitutions in T Cell Epitopes 4 and 5 by In Silico Analysis The sequences of peptides that were positive in the T cell assay were analysed using overlapping 9-mers from the epitope region using iTope™ and TCED™ in silico technologies. [Perry et al., *Drugs R D* 9(6):385-96 (2008).] Each 9-mer was tested against a database of MHC class II alleles (34 in total) and scored based on the fit and interactions with the MHC class II molecules. In addition, each 9-mer was BLAST searched against a database of known CD4+ cell epitopes in order to identify any high sequence homology between that of the 9-mer and of database peptides from unrelated proteins that stimulated T cell responses in previous T cell assays. On the basis of information from the in silico analysis, substitutions were identified for potential removal of CD4+ T cell epitope activity from the identified epitopes.

Epitope 5 spans the C-terminus of the native N2-CT fly-rich linker, the amino acids coded for by the multiple cloning site ("MCS") of the pFUSE vector used to produce the N1-N2-human Ig Fc fusion protein of SEQ ID NO:1, and the N-terminus of the human Ig Fc region. In silico analysis implicated M258 and V259 of SEQ ID NO:1 as the P1 anchors responsible T-cell activity. Based on their location outside of the N1-N2 coding region, removal of these two amino acids was not expected to cause a loss of function. These two amino acids were encoded by the MCS. Therefore, a double-stranded DNA molecule that modified the MCS and eliminated the nucleotides encoding M258 and V259 of SEQ ID NO:1 was produced by site-directed mutagenesis using appropriate oligonucleotide primers. This was followed by recloning the resulting mutagenized DNA sequence back into the pFUSE vector using the using EcoRI and BglII restriction sites in the MCS. The resulting mature (lacking the signal sequence) fusion protein omitted M258 and V259. That fusion protein retained the same ability to bind Abeta in the assay described below as the SEQ ID NO:1 fusion protein.

Epitope 4 overlaps the N2 domain and the native Gly-rich linker. Crystal structure of the g3p protein (not shown) suggested that Epitope 4 is located away from amyloid binding region and therefore would be tolerant to amino acid substitutions without affecting activity. V215 (SEQ ID NO:1), which was identified as a P1 anchor, is surface exposed with slight orientation of side chain towards the protein core. From structural analysis, any of the substitutions for V215 set forth in Tables 6 and 7 should remove the epitope. In addition any of the substitutions of other amino acids within this epitope as set forth in Tables 6 and 7 should also be accommodated. A nucleic acid sequence encoding an N1-N2-Ig Fc comprising a V215A substitution (SEQ ID NO:4) and omitting M258 and V259 was derived from the above-described nucleotide sequence by site-directed mutagenesis using appropriate oligonucleotide primers. The resulting mature fusion protein (SEQ ID NO:2) demonstrated increased binding to Abeta in the binding assay as compared to a fusion protein having the amino acid sequence of either SEQ ID NO:1 or the mature fusion protein lacking M258 and V239, described above. The nucleic acid sequence of SEQ ID NO:4 was used as the parent sequence to create genes incorporating all modifications in epitopes 1, 2 and 3.

Example 3: Design of Substitutions in T Cell Epitopes 1, 2 and 3 by In Silico Analysis Epitope 1 lies just C-terminal to a putative Abeta binding portion of N1-N2. In silico analysis of Epitope 1 highlighted amino acids 48-56 of SEQ ID NO:1 as an area for amino acid substitution and removal of the T-cell epitope. Amino acids within this 9-mer were targeted for substitution based upon the nature of the existing amino acid, surface exposure, and interaction with the amyloid binding region of g3p, as interpreted from the X-ray crystal structure of g3p. In particular, G48, T51 Y54 and T56 were targeted for substitution with the changes indicated in Table 1. Other potential amino acid substitutions in this region are set forth in Table 2.

iTope™ analysis of Epitope 2 pointed to amino acids 35-143 of SEQ ID NO:1 as a target for reducing or eliminating that epitope. Based on the X-ray crystal structure, amino acids 136-139 of SEQ ID NO:1 form a loop region that forms bonds with the hinge region of N1-N2 and thus may be important for amyloid binding activity. Changes to these amino acids are less preferred and are only presented in Table 2. The more preferred changes are to M135, R140, F141 and N143 and are set forth in Table 1. Other potential changes to this nine amino acid region are set forth in Table 2.

Amino acids 173-182 of SEQ ID NO:1 were identified within Epitope 3 as targets for substitution by in silico analysis. Epitope 3 is located in an alpha helical portion of the N2 domain, thus the strategy was to avoid introduction of hydrophobic residues and small polar uncharged residues. In addition, we wanted to avoid introducing polar residues acidic residues towards the C-terminus of this epitope. Based on X-ray crystallographic data, we targeted S173, D174, M176, D178 and W182 for substitution with the changes indicated in Table 1. Other potential amino acid substitutions in this region are set forth in Table 2.

Example 4: Generation of N1-N2-Human IgG Fc Polypeptides Raving Reduced T-Cell Epitopes Fifty-eight different nucleic acid molecules, each encoding N1-N2-human IgG Fc fusion proteins containing a different single amino acid substitution set forth in Table 3 were prepared. This was achieved by site-directed mutagenesis of SEQ ID NO:4 using appropriate oligonucleotide primers to introduce the desired substitution, followed by recloning of the PCR-amplified mutagenized sequence into the pFUSE-hIgG1-Fc2 vector (Invivogen®, Toulouse, France, Catalogue No. pfuse-hg1fc2).

Genes encoding these "deimmunized" Fc fusion polypeptides were transiently expressed in individual pFUSE-hIgG1-Fc2 vectors in FreeStyle 293-F cells (Invitrogen, Paisley, Scotland, Catalogue #R790-07). On the day of transfection, cells were diluted to $1\times10^6$/mL in FreeStyle 293 Media (Invitrogen, Catalogue #12338) ensuring a viability of >90%. Plasmid DNA and polyethyleneimine (PEI) were diluted separately in Optimem (Invitrogen, Catalogue #31985) and incubated for 5 minutes following which the PEI was added slowly to the DNA, and the DNA/PEI mixtures were incubated for 5 minutes at room temperature. After incubation, the DNA/PEI mixtures were added dropwise to the 293-F cells whilst swirling the flask. Transfected cultures were incubated at 37° C., 8% $CO_2$ on an orbital shaker platform rotating at 135 rpm for 6-7 clays, following which they were harvested.

Culture medium containing the polypeptide was harvested by centrifugation and pH adjusted using 10×PBS. Proteins were bound to Protein A Sepharose beads (Sigma, Dorset, UK) by rotating overnight at 4° C. The beads were washed twice with 1×PBS and transferred to SigmaPrep spin columns (Sigma). Samples were eluted by centrifugation using 0.1M Glycine piI3.0 and neutralized in the collection tube using 1/10$^{th}$ volume 1M Tris-HCl pH8.0. Eluates were buffer exchanged into 1×PBS using 2 ml ZebaSpin columns (Pierce, Cramlington, UK, Catalogue #89890). Samples were filter-sterilized and the absorbance at 280 nm was measured for each sample.

Example 5: ABeta Binding Analysis of Deimmunized Polypeptides

A. ABeta (Aβ) Fiber Preparation.

Aβ42 (1 mg, rPeptide A-1002-2) was dissolved in hexafluoroisopropanol (HFIP, 1 ml), vortexed thoroughly and incubated at room temperature for 2-18 hours until a clear solution appears. Aliquots (100 μl, 100 μg) were placed in 1.5 mL Eppendorf tubes and dry under vacuum (speed Vac, Eppendorf, Concentrator 5301) for 2-3 hr. The resulting monomers were resuspended in 20 μL DMSO, pipetted and vortexed thoroughly until completely dissolved. The solution was diluted with 260 μL of 10 mM HCl solution (final Aβ42 concentration is 80 μM) and vortexed for 20 seconds. The clear solution is incubated (without shaking) for 3 days at 37° C. to allow for aggregation.

For use in the assay Aβ42 fibers from the resulting stock solution were diluted 50-fold to 1.6 μM final concentration in PBS.

B. ELISA Plate Preparation.

To each well of a 96-well plate (F96 MAXISORP NUNC-IMMUNO PLATE; Catalog number: 442404, Lot 125436 and 128158; Denmark) was added 200 μL of a 1% BSA solution. The plates were sealed and incubated at 7° C. for 3 hr. Plates were then washed with PBS (250 μL/well)×3. We added 50 μL of the diluted Aβ42 fiber solution (1.6 μM) to each well and incubated uncovered at 37° C. overnight to complete dryness. PBS (50 μl/well) is added to control wells (without Aβ42 fibers). Plates were then washed 2× with water and 1× with PBS (250 μL/well for each washing).

C. ELSA Assay.

Varying concentrations of each polypeptide (as well as the polypeptide of SEQ ID NO:2) in 50 μL were added to each well, as well as to non-Aβ42 fiber coated wells and incubated for 1 h at 37° C. Plates were then washed 3× with PBS-T (0.05% Tween 20 in PBS) and 3× with PBS (250 μL/well for each washing). We then added 50 μl of HRP-conjugated Goat anti-Human anti Fey (Jackson Labs, Catalog number. 109-035-008, Lot number: 106617) diluted 1:2500 (0.32 μg/mL final) in PBS-T+1% Milk (Difco™ Skim Milk, Becton, Dickinson and Company. USA, Catalog number: 232100, Lot number: 7320448) to each well and incubated for 40 min at 37° C. Plates were then washed 6× with PBS-T and 2× with PBS (250 μL/well for each washing). We then added 50 μl/well OPD solution (15 mg/7.5 ml 0.05 M Citrate buffer pH-5.5/3 μl $H_2O_2$) and let color to develop for 3-6 min. We next added 25 μl/well of 4N HCl solution to stop reaction. Plates were read for absorbance at 492 nm and 405 nm. The 405 nm absorbance was subtracted from the 492 nm absorbance and the results plotted as a function of polypeptide concentrations. An $IC_{50}$ for binding for each deimmunized polypeptide was then calculated and compared to the $IC_{50}$ calculated for the polypeptide of SEQ ID NO:2. The results are shown in Table 9, below.

TABLE 9

Relative Change in ABeta Binding $IC_{50}$ for Polypeptides with a Single Additional Amino Acid Substitution in Epitope 1, 2 or 3 as Compared to Polypeptide of SEQ ID NO: 2

| Amino Acid Substitution | $IC_{50}$ Relative to SEQ ID NO: 2* |
|---|---|
| Epitope 1 G48H | 1.8 |
| Epitope 1 G48K | 1.1 |
| Epitope 1 G48R | 1.9 |
| Epitope 1 G48S | 1.2 |
| Epitope 1 G48T | 1.0 |
| Epitope 1 T51G | 0.8 |
| Epitope 1 T51H | 1.5 |
| Epitope 1 T51K | 2.5 |
| Epitope 1 T51P | 0.2 |
| Epitope 1 T51R | 2.0 |
| Epitope 1 T51Q | 0.8 |
| Epitope 1 T51N | 0.5 |
| Epitope 1 Y54G | 0.02/0.2 |
| Epitope 1 Y54H | 0.3 |
| Epitope 1 Y54K | 0.13/0.32 |
| Epitope 1 Y54P | 0.07 |
| Epitope 1 Y54R | 0.15/0.25 |
| Epitope 1 T56G | 0.1 |
| Epitope 1 T56H | 0.47/0.77 |
| Epitope 1 T56K | 0.5/0.66 |
| Epitope 1 T56P | 0.1/0.09 |
| Epitope 1 T56R | 0.8 |
| Epitope 2 M135A | 0.4 |
| Epitope 2 M135D | 0.5 |
| Epitope 2 M135G | 0.2 |
| Epitope 2 M135H | 0.1 |
| Epitope 2 M135K | 0.4/0.2 |
| Epitope 2 M135N | 0.3 |
| Epitope 2 M135R | 0.1 |
| Epitope 2 M135T | 0.14/0.3 |
| Epitope 2 R140A | 0.2 |
| Epitope 2 R140D | 0.3 |

TABLE 9-continued
Relative Change in ABeta Binding $IC_{50}$ for Polypeptides with a Single Additional Amino Acid Substitution in Epitope 1, 2 or 3 as Compared to Polypeptide of SEQ ID NO: 2

| Amino Acid Substitution | $IC_{50}$ Relative to SEQ ID NO: 2* |
|---|---|
| Epitope 2 R340E | 0.3 |
| Epitope 2 R140G | 0.2 |
| Epitope 2 R140H | 0.2 |
| Epitope 2 R140Q | 0.28/0.22 |
| Epitope 2 F141D | 0.2 |
| Epitope 2 F141E | 0.2 |
| Epitope 2 N143A | 1.9/1.1 |
| Epitope 2 N143G | 0.19/0.08 |
| Epitope 3 S173G | 0.2 |
| Epitope 3 S173P | 0.4 |
| Epitope 3 M176G | 0.3 |
| Epitope 3 M176H | 0.4 |
| Epitope 3 M176K | 0.2 |
| Epitope 3 M176N | 0.5 |
| Epitope 3 D178G | 0.2 |
| Epitope 3 D178N | 0.5/0.4 |
| Epitope 3 D178Q | 0.6 |
| Epitope 3 D178S | 0.3 |
| Epitope 3 W181G | 0.5 |
| Epitope 3 W181H | 0.47/0.87 |
| Epitope 3 W181K | 0.3 |
| Epitope 3 W181R | 0.5/0.8 |
| Epitope 3 S173K | 0.17/0.07 |
| Epitope 3 K174R | 1.2/1.0 |
| Epitope 3 M176R | 0.2 |
| Epitope 3 D178T | 0.4 |

*Numbers reflect $IC_{50}$ (substituted polypeptide)/$IC_{50}$ (polypeptide of SEQ ID NO: 2). Multiple values reflect duplicate testing in the binding assay.

Example 6: Analysis of Whole Protein CD4+ T Cell Responses

In order to analyze CD4+ T cell responses from any of the polypeptides of the invention in comparison to SEQ ID NO:1, a whole protein T cell assay was performed. PBMCs were isolated from 20 healthy human donor buffy coats prepared as in Example 1. PBMCs were revived from frozen in AIM-V® culture medium and $CD14^+$ cells were isolated using Miltenyi CD14 Microbeads and LS columns (Miltenyi Biotech, Oxford, UK). Monocytes were resuspended in AIM-V® supplemented with 1000 U/ml IL-4 and 1000 U/ml GM-CSF ("DC culture medium") to 4-6×$10^6$ PBMC/ml and then distributed in 24 well plates (2 ml final culture volume). Cells were fed on day 2 by replacement of a half volume DC culture medium. By day 3, monocytes had differentiated to semi-mature dendritic cells (DC) which were pre-incubated with antigens comprising either 40 μg/ml of test polypeptide or 40 μg/ml of the polypeptide of SEQ ID NO:1 and 1.00 μg/ml KLH or medium only. Semi-mature DC were incubated with antigen for 24 hours after which excess antigen was removed by washing the cells twice and resuspending in DC culture medium supplemented with 50 ng/ml. TNF-α (Peprotech, London, UK). DC were fed on day 7 by replacement of a half volume DC culture medium supplemented with 50 ng/ml TNFα and mature DC were harvested on day 8. The harvested mature DC were counted and viability assessed using trypan blue dye exclusion. The DC were then γ-irradiated (4000 rads) and resuspended at 2×$10^5$ cells per ml in AIM-V medium before use analysis in T cell proliferation and ELISpot assays as below. Additionally, on day 8, fresh CD4+ T cells were also prepared. To purify CD4+ T cells, PBMCs were revived in AIM-V® culture medium and $CD4^+$ cells isolated using Miltenyi CD4 Microbeads and LS columns (Miltenyi Biotech, Oxford, UK) and resuspended in AIM-V® medium at 2×$10^6$ cells/ml.

On day 8, T cell proliferation assays were established whereby 1×$10^5$ autologous $CD4^+$ T cells were added to 1×$10^4$ antigen-loaded DC (ratio of 10:1) in 96 well U-bottomed plates, with AIM-V® medium added to a final volume 200 μl/well. On day 14, assay plates were pulsed with 1 uCi [$^3$H] (Perkin Elmer, Beaconsfield, UK) per well in 25 μl AIM-V® for 6 hours before harvesting onto filter mats (Perkin Elmer) using a TonfTec Mach III (Hamden Conn., USA) cell harvester. All polypeptides were tested in sextuplet cultures. Counts per minute (cpm) for each well were determined by Meltilex™ (Perkin Elmer) scintillation counting on a 1450 Microbeta Wallac Trilux Liquid Scintillation Counter (Perkin Elmer) in paralux, low background counting. Counts per minute for each antigen were normalised to the AIM-V® medium only control.

For ELISpot assays, ELISpot plates (Millipore, Watford, UK) were coated with 100 ul/well IL-2 capture antibody (R&D Systems, Abingdon, UK) in PBS. Plates were then washed twice in PBS, incubated overnight in block buffer (1% BSA (Sigma) in PBS) and washed in AIM-V® medium. On day 8, 1×$10^5$ autologous $CD4^+$ T cells were added to 1×$10^4$ antigen loaded DC (ratio of 10:1) in 96 well ELISpot plates. All polypeptide preparations were tested in sextuplet cultures. For each donor PBMC, a negative control (AIM-V® medium alone), no cells control and a PHA (10 ug/ml) positive control were also included.

After a further 7 day incubation period, ELISpot plates were developed by three sequential washes in $dH_2O$ and PBS prior to the addition of 100 ul filtered biotinylated detection antibody (R&D Systems, Abingdon, UK) in PBS/1% BSA. Following incubation at 37° C. for 1.5 hour, plates were further washed three times in PBS and 100 ul filtered streptavidin-AP (R&D Systems) in PBS/1% BSA was added for 1 hour (incubation at room temperature). Streptavidin-AP was discarded and plates were washed four times in PBS. BCIP/NBT (R&D Systems) was added to each well and incubated for 30 minutes at room temperature. Spot development was stopped by washing the wells and the backs of the wells three times with $dH_2O$. Dried plates were scanned on an Immunoscan™ Analyser and spots per well (spw) were determined using Immunoscan™ Version 4 software.

For both proliferation and IL-2 ELISpot assays, results were expressed as a Stimulation Index (SI) defined as the ratio of cpm (proliferation assay) or spots (ELISpot assay) for the test polypeptide against a medium-only control using a threshold of SI equal to or greater than 2 (SI≥2.0) for positive T cell responses.

Example 7: Design of Double and Triple Substitutions in Two or More of T Cell Epitopes 1, 2 and 3

Based on the results of the binding assay, the following substitutions were chosen at epitopes 1, 2 and 3 to be present in polypeptides that contain two amino acid substitutions as compared to SEQ NO:2, each substitution in a different epitope.

TABLE 10

Amino Acid Substitutions for Variants Comprising Two Epitope and Three Eptiope Modifications.

| Epitope | Amino Acid | Original Amino Acid in SEQ ID N ily adapted from Chang, E. and Kuret, J., Anal Biochem 373, 330-6, (2008) and Wanker, E. E. et al., Methods Enzymol 309, 375-86, (1999). Specifically, 2.5 µM preparations of fAβ amyloid fibers were pre-incubated with different concentrations of the variant fusion polypeptides of the invention (1 nM to 2 µM) at 37° C. for 3 days. After incubation, fibers with and without fusion polypeptide were diluted and spotted on cellulose acetate membranes on vacuum blots. The membranes were extensively washed with PBS and probed with an antibody specific for the N-terminal of Aβ for 1 hr. HRP-conjugated secondary Ab was used to quantitate the fibrillar aggregates retained on the membrane. Spot color was analyzed and digitized using a densitometric scanner. An $EC_{50}$ (half maximal effective concentration) was calculated based upon the intensities of the signal of each spot versus the concentration of fusion polypeptide added to each spot.

As can be seen from the above Examples, the variant polypeptides of the invention all exhibited binding to Aβ as determined by the ELISA assay. Most of the variant polypeptides tested also exhibited disaggregation of Aβ, as determined by the dot blot assay.

Example 9: Construction and Analysis of Polypeptides with a Modified Glycosylation Signal We constructed polypeptides lacking a glycosylation signal at amino acids 39-41 of SEQ ID NO:1 or SEQ ID NO:2 using the nucleotides sequence of either SEQ ID NO:3 or a modified version of nucleotide sequence SEQ ID NO:4 that encoded Polypeptide No. 86 as starting material for site-direct mutagenesis.

A plasmid vector derived from pFUSE-hIgG1-Fc2 vector (InVivogen) and encoding Polypeptide 86 fused to a mammalian signal sequence, was mutagenized using the QuickChange Site-Directed Mutagenesis Kit (Agilent) and the following printers:

```
Forward primer:
                              (SEQ ID NO: 8)
GCTGTCTGTGGAATGCTGGAGGCGTTGTAGTTTG Reverse primer:
                              (SEQ ID NO: 9)
CAAACTACAACGCCTCCAGCATTCCACAGACAGC
``` following manufacturer's directions to create a T41G substitution. The resulting vector (SEQ ID NO:7) was used to transform NEB 5-alpha competent *E. coli* cells in order to isolate and sequence the desired plasmid using standard techniques.

The purified vector was then used to transform Expi293 cells using the commercially available Expi293™ Expression System (Life Technologies). One day before transfection, Expi293 cells were seeded at a density of $2 \times 10^6$ viable cells/ml. On the day of transfection, 500 µg of the filter-sterilized plasmid was diluted into Opti-MEM I to a total volume of 25 ml. In a separate tube, 1.333 ml ExpiFectamine™ 293 Reagent was diluted in 25 ml Opti-MEM I and mixed by inverting. After five minutes incubation at room temperature the diluted DNA was added to the diluted ExpiFectamine™ 293 Reagent and incubated for an additional 20-30 minutes. The DNA-ExpiFectamine™ 293 Reagent complex was slowly added to 500 ml cells (>$3 \times 10^6$ cells/ml) while gently swirling the flask. ExpiFectamine™ 293 Transfection Enhancers I and II, 2.5 ml and 25 ml respectively, were added to the transfected cells after approximately 18 hours and cells are incubated for another 5 days at 37° C., 8% $CO_2$, 135 rpm on an orbital shaker. The expressed fusion protein (termed "Polypeptide 86-T41G")-containing media was harvested by centrifugation at 10,000 rpm at 4° C. for 20 minutes. The supernatant was purified on a 5 ml HiTrap rProtein A FF column (GE Healthcare), with all steps being performed at 4° C. The column was regenerated with 5 volumes of elution buffer (0.1M glycine, pH 3), and washed in 5-10 volumes 20 mM sodium phosphate buffer before applying the cell media using a flow rate of 5 ml/min. The column was washed with 5-10 volumes 20 mM sodium phosphate buffer before eluting off bound Polypeptide 86-T41G with 0.1 M glycine pH 3. One to three ml fractions were collected in tubes with 1M Tris-HCl pH 9 to adjust pH. Yield was determined by absorbance at 280 nm on a Nanodrop 2000C. Five µl of each protein-containing fraction was separated on a SDS-PAGE TGX gel (BioRad) and Coomassie stained for 2 hours. Fractions containing Polypeptide 86-T41G were pooled and dialyzed in D-PBS overnight at 4° C. The final Polypeptide 86-T41G sample was sterilized on Ultrafree spin filters and the concentration was measured on the Nanodrop 2000C.

Figure 9:
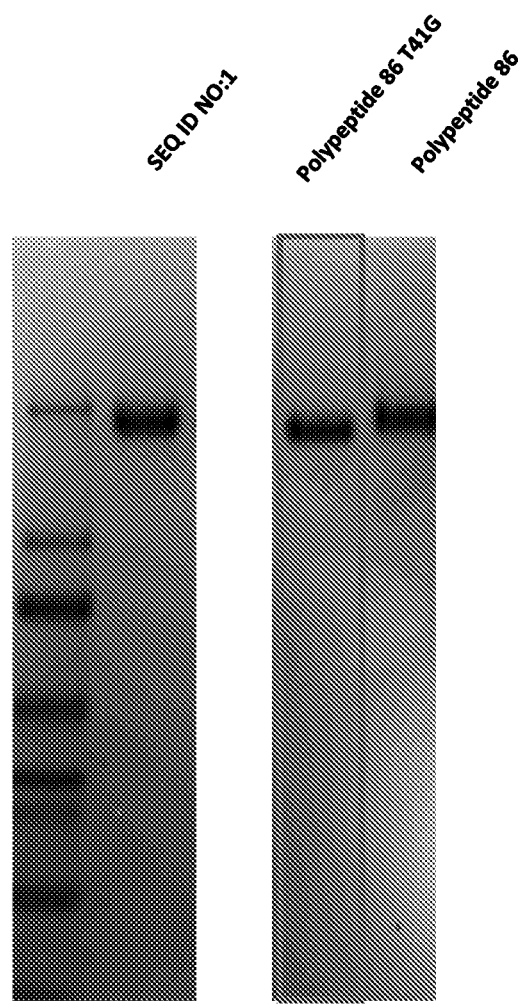

Purified Polypeptide 86-T41G (SEQ ID NO:6) was analyzed by SDS-PAGE and migrated as a single band with slightly lower molecular weight (apparent 500 dalton less) than Polypeptide 86 (FIG. 9). We believe this lower molecular weight is due to both the T to G change at amino acid 41, as well as the loss of glycosylation on N39.

Purified Polypeptide 86-T41G was also analyzed by size exclusion chromatography on a Superdex200 increase 10/300 column. The column was washed and equilibrated with 100 ml of phosphate buffered saline ("PBS"). One hundred micrograms (100 µg) of Polypeptide 86-T41G was diluted in PBS to a final volume of 200 µL and loaded onto the column. The column was then eluted with 1.5 column volumes of PBS at a rate of 0.75 mL/minute. Protein in fractions was monitored by spectrophotometrically at 214 nm and 280 nm and demonstrated a sharp peak indicating homogeneity (data not shown).

Purified Polypeptide 86-T41G was analyzed for Abeta binding using the ELISA described in Example 5. The $EC_{50}$ for Abeta binding in this assay was calculated to be 13.15 nM, compared to 20.6-27.01 nM for the polypeptide of SEQ ID NO:1 and 34.5 nM for Polypeptide 86.

Figure 10:
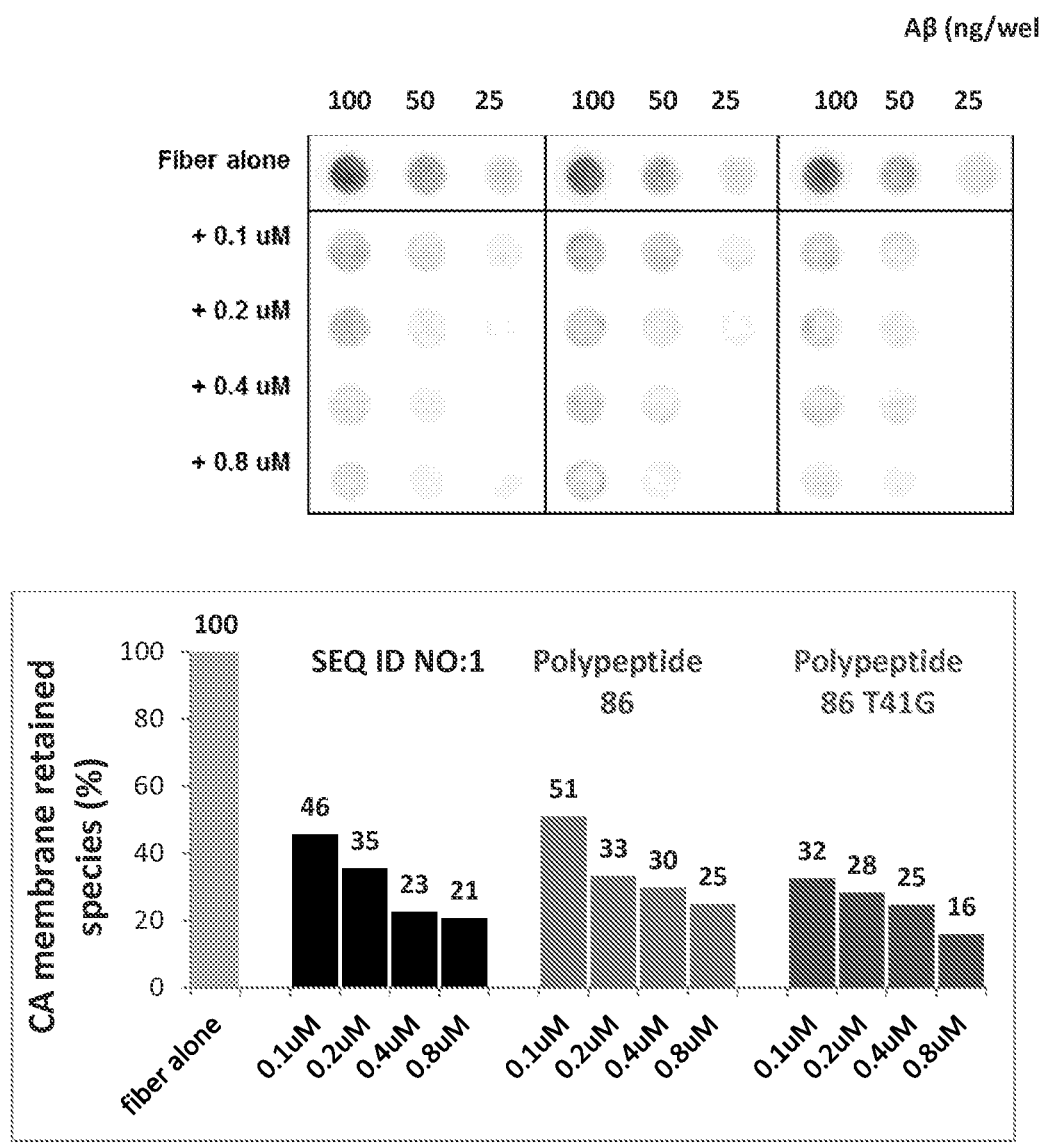

Purified Polypeptide 86-T41G was also compared to the polypeptide of SEQ ID NO:1 and Polypeptide 86 for Abeta binding using the cellulose acetate filter retardation assay described in Example 8. The results of this assay are shown in FIG. 10.

Purified Polypeptide 86-T41G was then compared to Polypeptide 86 and the polypeptide of SEQ ID NO:1 (as well as humanized A33 antibody and keyhole limpet hemocyanin as positive controls) in the whole protein CD4+ T cell Response assay using 50 different PBMC donors representing 95% of the human HLA haplotypes; and in the ELISpot cytokine (IL-2) assays described in Example 6. The results are shown in Tables 13 and 14, below.

TABLE 13

| PBMC T-cell Proliferative Response Assay Results. | | | |
|---|---|---|---|
| Sample | Mean SI | SD | % Response |
| SEQ ID NO: 1 | 2.21 | 0.32 | 12 |
| Polypeptide 86 | 2.66 | 1.02 | 4 |
| Polypeptide 86 T41G | 2.11 | 0.15 | 4 |

TABLE 13-continued

PBMC T-cell Proliferative Response Assay Results.

| Sample | Mean SI | SD | % Response |
|---|---|---|---|
| Humanized A33 | 3.29 | 1.83 | 12 |
| KLH | 4.74 | 3.28 | 84 |

TABLE 14

ELISpot IL-2 Assay Results.

| Sample | Mean SI | SD | % Response |
|---|---|---|---|
| SEQ ID NO: 1 | 2.51 | 0.64 | 14 |
| Polypeptide 86 | 2.83 | 1.03 | 4 |
| Polypeptide 86 T41G | 2.33 | 0.22 | 4 |
| Humanized A33 | 2.46 | 0.33 | 20 |
| KLH | 4.57 | 4.32 | 86 |

As can be seen from the above Tables the polypeptide of SEQ ID NO:1 (no amino acid changes in either the putative glycosylation site at amino acids 39-41 or any putative T-cell epitopes) elicited proliferative responses ("SI") >2 times background for 12% of the donors (6/50). Polypeptide 86 and Polypeptide 86 T41G elicited proliferative responses from significantly fewer donor PBMCs (4%; 2/50) with responders having proliferative response also slightly higher than 2 times background. This indicates lower projected immunogenicity of Polypeptide 86 T41G for human subjects. The IL-2 assay confirms the T-cell response assay results.

Polypeptide 86 T41G was also compared to the polypeptide of SEQ ID NO:1 for binding to Abeta42 fibers, NAC fibers and tau-mtbr fibers.

Fiber and ELISA Plate Preparation.

Aβ42 peptide (rPeptide A-1002-2) was dissolved in hexafluoroisopropanol by vortexing and incubation at room temperature for 18 hours. Aliquots were dried under vacuum and stored at −20° C. 100 ug of Aβ42 monomers were dissolved in 20 µl DMSO, dissolved by vortex and diluted to 80 µM in 10 mM HCl solution. The Aβ42 peptide solution was incubated for 3 days at 37° C. and fiber formation verified with ThT fluorescence assay.

The non-amyloid beta component (NAC) of senile plaque is an aggregated fragment of alpha-synuclein, the aggregate that is the hallmark of Parkinson's disease. NAC peptide ((Bachem H2598) was dissolved in 20 mM NaHCO$_3$ at 600 uM and centrifuged for 1 hour, 100,000×g at 4° C. Supernatant was neutralized with 2N HCl and mixed 1:1 with 10 mM HCl. The peptide was incubated for 4 days at 37° C. and fiber formation confirmed by ThT fluorescence assay.

Fibers comprising the microtubule binding portion of Tau (Tau-mtbr fibers) were made according to Frost et al. J Biol Chem. 2009 May 8; 284(19):12845-52. Briefly, 40 uM of tau-mtbr protein was incubated with 40 uM low-molecular weight heparin (Fisher Scientific, BP2524) and 2 mM DTT for 3 days at 37° C. Fibril formation was confirmed by ThT fluorescence assay.

Fibers were diluted to 1 µM in PBSA-0.02% and dry-coated on Maxisorp Nunc Immunoplate ELISA plates (ThermaFisher Cat no. 442404) by incubation over night at 37° C. Wells were blocked, 200 µl/well, in Superblock (Thermofisher Cat no. 37515) for 1 hour at room temperature and washed in PBST-0.05%.

Binding Assay and Results.

The polypeptide of SEQ ID NO:1 and Polypeptide 86 T41G were separately added to the fiber ELISA at 50 and 200 nM and incubated for 1 hour at 37° C. Wells were washed in PBST-0.05% 6×200 µl before incubation with goat anti-human IgG Fc fragment specific-HRP (Jackson labs Cat no. 109-035-008), 1:2500 in TBST-0.05%; 1% milk block (LabScientific Cat no. 732-291-1940), for 45 minutes in room temperature. Plates were washed in 4×200 ul TBST-0.05%, 2×200 ul PBS before adding 50 ul TMB solution (Sigma T0440) per well. The reaction was left to develop for 8 minutes and stopped by adding 50 µl 2N HCl per well. The absorbance at 450 nm was recorded in a Tecan plate reader (Infinite M1000Pro).

Data points were taken from the average of triplicate wells with standard deviation calculated with GraphPad Prism. The values were corrected for background by subtracting the mean absorbance in wells incubated without either polypeptide for each substrate.

Figure 11:
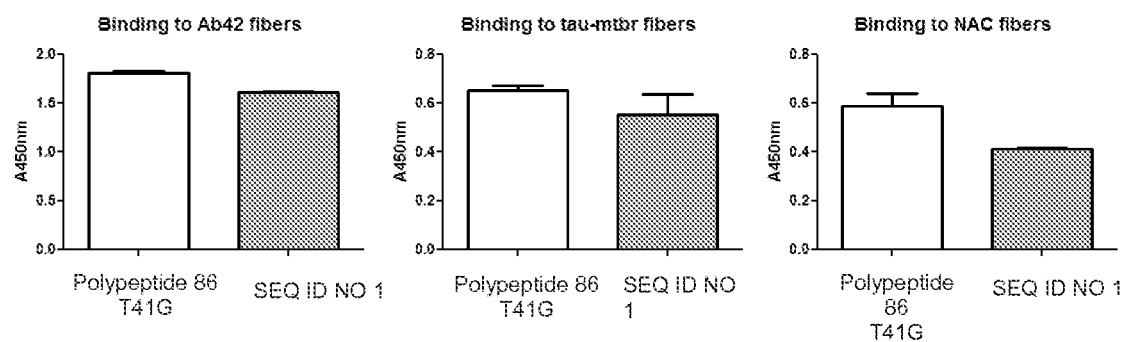

As shown in FIG. 11, Polypeptide 86 T41G bind Aβ42m NAC and tau-mtbr fibers with the same or higher affinity compared to the polypeptide of SEQ ID NO:1.

We also constructed by similar protocols the following variants of SEQ ID NO:1 modified only to eliminate the putative glycosylation site (substitution indicated in parentheses):

| |
|---|
| Polypeptide 200 (N39A) |
| Polypeptide 201 (N39Q) |
| Polypeptide 202 (T41M) |
| Polypeptide 203 (T41W) |
| Polypeptide 204 (T41H) |
| Polypeptide 205 (T41V) |
| Polypeptide 206 (T41I) |
| Polypeptide 207 (T41L) |
| Polypeptide 208 (T41R) |
| Polypeptide 209 (T41K) |
| Polypeptide 210 (T41Y) |
| Polypeptide 211 (T41F) |
| Polypeptide 212 (T41D) |
| Polypeptide 213 (T41E) |
| Polypeptide 214 (T41Q) |
| Polypeptide 215 (T41N) |
| Polypeptide 216 (T41A) |
| Polypeptide 217 (T41G). |

Example 10: Pharmacokinetic (PK) Studies of Polypeptide 217 and SEQ ID NO:1

Animal Treatment and Sample Collection.

C57B16 mice (8-12 wks; Hilltop Lab Animals) were administered a single 20 mg/kg intraperitoneal dose of the polypeptide of SEQ ID NO:1 (n=22) or Polypeptide 217 (n=22) used. The polypeptide of SEQ ID NO:1 was administered once (20 mg/kg, i.p.) to 22 mice. Polypeptide 217 was administered once (20 mg/kg, i.p.) to a separate set of 22 mice. Blood was collected once each animal at different times (0 h, 6 h, 9 h, 12 h, 1 d, 3 d, 7 d and 14 d post-dosing). Plasma was isolated from the blood samples, stored in 100 µL aliquots, and used for all subsequent analyses. After collection of the blood, mice were euthanized, transcardially perfused with PBS and their brains harvested. The brains were hemisected and each hemisphere further sectioned into a rostral, caudal, hippocampus and cerebellum portion. Plasma was shipped to Intertek (San Diego, Calif.) for pharmacokinetic analysis, while left frontal cortex was shipped to Cambridge Biomedical (Boston, Mass.) for PK analysis.

Plasma ELISA Analysis.

All standards and samples that were analyzed were exposed to 217 mM acetic acid for 30 min at room temperature ("RT"), and then neutralized in (1:1.5 v/v 1M Tris pH 9.5:sample). The acid dissociation step solubilized polypeptide present in an insoluble fraction.

A sandwich ELISA assay was used to measure polypeptide levels in plasma. Maxi Sorp™ plates were coated with rabbit anti-M13 (Abcam: ab6188) at 1:1,000 dilution from stock (3.7 µg/mL, 0.37 µg/well) overnight in carbonate buffer (pH 9.6) at 4° C. Plates were washed three times with PBS containing 0.1% Tween-20 ("PBST") and blocked with 1% milk in PBS for 2 h at 37° C. followed by 1 h at RT. Plates were again washed three times with PBST and then samples or standards were added to wells and incubated for 1 h at 37° C. Wells were then washed 3× with PBST, and incubated with HRP-labeled goat anti-Human IgG (heavy & light chains, Bethel: A80-219P; 1:10,000) for 30 min at RT. Welts were washed 3× with PBST, and the plates were then developed at RT with TMB substrate. Reactions were stopped after the $A_{450}$ of the highest standards was between 0.6-0.8. Levels of polypeptide were quantified from the absorbance read at 450 nm, minus the reference absorbance at 650 nm. Plasma was analyzed at dilutions of 1:20, 1:300 and 1:3,000; no matrix interference was observed at these dilutions. The results are shown below in Table 15.

TABLE 15

Plasma Pharmacokinetic Parameters.

| Parameter | SEQ ID NO: 1 | Polypeptide 217 |
|---|---|---|
| $C_{max}$ | 140 µg/mL | 179 µg/mL |
| $T_{max}$ | 6 h | 6 h |
| Beta-phase ½ life | 5 days | 10 days |
| Clearance | 24.5 mL/day/kg | 8.3 mL/day/kg |
| AUC | 816.33 day*µg/ml | 2396.1 day*µg/ml |

Brain ELISA Analysis.

Brain tissue (left frontal cortex) was homogenized in cold PBS using trip Pure M-Bio Grade beaded tubes and a Precellys024 Lysis Homogenizer (5,000 RPM twice for 20 sec, with a 5 sec interval between homogenization cycles). Homogenate was centrifuged at 14,000 rpm for 5 min at 4° C. Supernatant was removed to a new tube and used for all subsequent analyses. Protein content of brain lysate was determined using a Pierce BCA protein assay kit. Lysate was used at a 1:2 dilution.

A sandwich ELISA assay was used to measure polypeptide levels in brain. MaxiSorp™ plates were coated with rabbit anti-M13 (Abeam: ab6188) at 1:1,000 (3.7 µg/mL, 0.37 µg/well) overnight in carbonate buffer at 4° C. Plates were washed 3× with PBST and blocked with 1% milk in PBS for 2 h at 37° C., followed by 1 h at RT. Plates were then washed 3× with PBST, and samples or standards were added to wells and incubated for 1 h at 37° C. Plates were again washed 3× with PBST, and then wells were incubated with HRP-labeled donkey anti-Human IgG (heavy & light chains, Jackson ImmunoResearch: 709-035-149; 1:10,000) for 30 min at RT. After 3× washes with PBST, plates were developed for 15 min at RT with TMB substrate. Reactions were stopped and absorbance read at 450 nm. Levels of polypeptide in brain were expressed relative to protein content of lysates. The results are shown below in Table 16.

TABLE 16

Brain Pharmacokinetic Parameters

| Parameter | SEQ ID NO: 1 | Polypeptide 217 |
|---|---|---|
| $C_{max}$ | 2.5 ng/mg | 2.7 ng/mg |
| $T_{max}$ | 3 d | 3 d |
| Beta-phase ½ life | 3 days | 7 days |
| AUC | 14.44 day*ng/mg | 32.90 day*ng/mg |

The invention claimed is:

1. A polypeptide comprising SEQ ID NO: 5, optionally further comprising an N-terminal methionine.

2. A pharmaceutical composition comprising the polypeptide of claim 1 and a pharmaceutically acceptable carrier.

3. The pharmaceutical composition of claim 2, wherein the composition is formulated for injection into the bloodstream of a patient, infusion into the bloodstream of a patient, direct administration to the brain, or direct administration to the CNS.

4. A method of reducing amyloid or tau protein aggregates in a patient in need thereof, comprising administering to the patient an effective amount of the polypeptide of claim 1.

5. The method of claim 4, wherein the patient is positive for florbetapir when florbetapir is used as an imaging agent in positron emission tomography.

6. The method of claim 4, wherein the patient is suffering from and/or exhibits symptoms of a disease selected from Alzheimer's disease, early onset Alzheimer's disease, late onset Alzheimer's disease, presymptomatic Alzheimer's disease, Parkinson's disease, SAA amyloidosis, disease characterized by formation of amyloid protein by aggregation of cystatin C, disease characterized by formation of amyloid protein by aggregation of immunoglobulin light chain, familial amyloidotic polyneuropathy (FAP), familial amyloidotic cardiomyopathy (FAC), islet amyloid polypeptide (IAPP) amyloidosis, Finnish form of FAP (aggregation of gelsolin), senile systemic amyloidosis (SSA), hereditary Icelandic syndrome, senility, multiple myeloma, prion diseases, kuru, Creutzfeldt-Jakob disease (CJD), Gerstmann-Straussler-Scheinker disease (GSS), fatal familial insomnia (FFI), scrapie, bovine spongiform encephalitis (BSE), amyotrophic lateral sclerosis (ALS), spinocerebellar ataxia (SCA1, SCA3, SCA6, or SCA7), Huntington's disease, dentatorubral-pallidoluysian atrophy, spinal and bulbar muscular atrophy, hereditary cerebral amyloid angiopathy, familial amyloidosis, British/Danish dementia, familial encephalopathy, Amyotrophic lateral sclerosis/parkinsonism-dementia complex, Argyrophilic grain dementia, Corticobasal degeneration, Dementia pugilistica, diffuse neurofibrillary tangles with calcification, Down's syndrome, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, Tangle only dementia, frontotemporal lobar degenerations (FTLDs), and frontotemporal lobe dementia (FTD) including a patient having one or more of the following clinical syndromes: behavioral variant FTD (bvFTD), progressive non-fluent aphasia (PNFA), frontotemporal dementia with parkinsonism linked to chromosome 17, Progressive Supranuclear Palsy (PSP), and semantic dementia (SD).

7. A nucleic acid sequence encoding the polypeptide of claim 1, wherein the nucleic acid sequence optionally further encodes a mammalian signal sequence fused to and in frame with the polypeptide encoding sequence.

8. A vector comprising the nucleic acid sequence of claim 7, wherein the nucleic acid sequence is operatively linked to an expression control sequence in the vector.

9. A host cell comprising the vector of claim 8.

10. A method of making the polypeptide of claim 1, comprising expressing the protein encoded by the nucleic acid sequence of claim 7, and isolating the expressed polypeptide.

11. A method of making the polypeptide of claim 1, comprising culturing the host cell of claim 9 under conditions sufficient to allow expression of the polypeptide; and isolating the expressed polypeptide.

* * * * *